United States Patent
Lewis et al.

(10) Patent No.: US 9,213,163 B2
(45) Date of Patent: *Dec. 15, 2015

(54) ALIGNING INTER-PUPILLARY DISTANCE IN A NEAR-EYE DISPLAY SYSTEM

(75) Inventors: John R. Lewis, Bellevue, WA (US); Yichen Wei, Beijing (CN); Robert L. Crocco, Seattle, WA (US); Benjamin I. Vaught, Seattle, WA (US); Kathryn Stone Perez, Kirkland, WA (US); Alex Aben-Athar Kipman, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/221,662

(22) Filed: Aug. 30, 2011

(65) Prior Publication Data

US 2013/0050642 A1    Feb. 28, 2013

(51) Int. Cl.
*G02B 27/14* (2006.01)
*G03H 1/00* (2006.01)
(Continued)

(52) U.S. Cl.
CPC . *G02B 7/12* (2013.01); *A61B 3/113* (2013.01); *G02B 27/017* (2013.01); *G02B 2027/014* (2013.01); *G02B 2027/0127* (2013.01); *G02B 2027/0187* (2013.01)

(58) Field of Classification Search
CPC .......... G02B 27/0172; G02B 27/0149; G02B 27/145; G02B 27/0101; H02K 21/24; H02K 21/12; H02K 15/02; H02K 2201/12; G03B 21/00; G03B 21/14; G01C 21/22; G09F 19/18; G09G 3/003

USPC ....... 359/630–634, 13–14; 310/49 R, 156.32, 310/156.33, 156.34, 156.35, 266–268, 310/156.02; 353/11–12, 28, 119; 345/7, 9; 340/438, 980, 995.1, 815.47, 815.74; 351/200, 205–206, 210, 221

See application file for complete search history.

(56) References Cited

U.S. PATENT DOCUMENTS 5,539,422 A    7/1996  Heacock et al.
5,572,361 A    11/1996 Kamiya et al.
(Continued)

FOREIGN PATENT DOCUMENTS

CA      2685976 A1    11/2008
CN    101542584 A     9/2009
(Continued)

OTHER PUBLICATIONS

Canadian Office Action dated Nov. 7, 2011, Canadian Patent Application No. 2,750,287 filed Aug. 29, 2011, 3 pages.
(Continued)

*Primary Examiner* — Dawayne A Pinkney
(74) *Attorney, Agent, or Firm* — Dan Choi; Judy Yee; Micky Minhas

(57) ABSTRACT

The technology provides for automatic alignment of a see-through near-eye, mixed reality device with an inter-pupillary distance (IPD). A determination is made as to whether a see-through, near-eye, mixed reality display device is aligned with an IPD of a user. If the display device is not aligned with the IPD, the display device is automatically adjusted. In some examples, the alignment determination is based on determinations of whether an optical axis of each display optical system positioned to be seen through by a respective eye is aligned with a pupil of the respective eye in accordance with an alignment criteria. The pupil alignment may be determined based on an arrangement of gaze detection elements for each display optical system including at least one sensor for capturing data of the respective eye and the captured data. The captured data may be image data, image and glint data, and glint data only.

19 Claims, 26 Drawing Sheets

(51) Int. Cl.

| | | |
|---|---|---|
| G02F 1/1335 | (2006.01) | |
| G03B 21/26 | (2006.01) | |
| G09G 5/00 | (2006.01) | |
| A61B 3/14 | (2006.01) | |
| G02B 7/12 | (2006.01) | |
| A61B 3/113 | (2006.01) | |
| G02B 27/01 | (2006.01) | |

(56) References Cited

U.S. PATENT DOCUMENTS

| | | | | |
|---|---|---|---|---|
| 5,708,449 | A | * | 1/1998 | Heacock ............... G02B 23/10 345/7 |
| 5,815,126 | A | | 9/1998 | Fan et al. |
| 6,034,653 | A | | 3/2000 | Robertson |
| 6,069,608 | A | | 5/2000 | Izumi et al. |
| 6,151,061 | A | | 11/2000 | Tokuhashi |
| 6,396,461 | B1 | | 5/2002 | Lewis et al. |
| 6,433,760 | B1 | | 8/2002 | Vaissie et al. |
| 6,480,174 | B1 | | 11/2002 | Kaufmann et al. |
| 6,518,939 | B1 | | 2/2003 | Kikuchi |
| 6,545,650 | B1 | | 4/2003 | Yamada et al. |
| 6,864,910 | B1 | | 3/2005 | Ogino et al. |
| 6,943,754 | B2 | | 9/2005 | Aughey et al. |
| 7,193,584 | B2 | | 3/2007 | Lee |
| 7,193,585 | B2 | | 3/2007 | Takagi |
| 7,229,174 | B2 | | 6/2007 | Hakkinen |
| 7,401,920 | B1 | | 7/2008 | Kranz et al. |
| 7,538,744 | B1 | | 5/2009 | Liu et al. |
| 7,573,525 | B2 | | 8/2009 | Yamasaki |
| 7,804,507 | B2 | | 9/2010 | Yang et al. |
| 7,883,415 | B2 | | 2/2011 | Larsen et al. |
| 2002/0105482 | A1 | | 8/2002 | Lemelson et al. |
| 2002/0113755 | A1 | * | 8/2002 | Lee ............... G02B 7/12 345/7 |
| 2002/0163486 | A1 | * | 11/2002 | Ronzani et al. ........... 345/87 |
| 2002/0167462 | A1 | * | 11/2002 | Lewis et al. ............ 345/7 |
| 2004/0238732 | A1 | | 12/2004 | State et al. |
| 2005/0190180 | A1 | | 9/2005 | Jin et al. |
| 2005/0207614 | A1 | | 9/2005 | Schonberg |
| 2006/0072206 | A1 | | 4/2006 | Tsuyuki et al. |
| 2006/0077558 | A1 | | 4/2006 | Urakawa et al. |
| 2006/0119539 | A1 | | 6/2006 | Kato |
| 2006/0221266 | A1 | | 10/2006 | Kato |
| 2006/0250322 | A1 | * | 11/2006 | Hall et al. ............... 345/8 |
| 2007/0052672 | A1 | | 3/2007 | Ritter et al. |
| 2007/0097495 | A1 | | 5/2007 | Knoblich et al. |
| 2007/0132950 | A1 | | 6/2007 | Victor et al. |
| 2007/0273983 | A1 | | 11/2007 | Hebert |
| 2008/0048931 | A1 | | 2/2008 | Ben-Ari |
| 2008/0216171 | A1 | | 9/2008 | Sano et al. |
| 2009/0243967 | A1 | | 10/2009 | Kato |
| 2010/0079356 | A1 | | 4/2010 | Hoellwarth |
| 2010/0085462 | A1 | | 4/2010 | Sako et al. |
| 2010/0110368 | A1 | | 5/2010 | Chaum |
| 2010/0149073 | A1 | | 6/2010 | Chaum et al. |
| 2010/0186072 | A1 | | 7/2010 | Kumar |
| 2010/0289880 | A1 | * | 11/2010 | Moliton et al. ............ 348/47 |
| 2011/0109880 | A1 | | 5/2011 | Nummela |
| 2011/0194029 | A1 | | 8/2011 | Herrmann et al. |
| 2011/0214082 | A1 | | 9/2011 | Osterhout et al. |
| 2012/0021806 | A1 | | 1/2012 | Maltz |
| 2013/0038510 | A1 | | 2/2013 | Brin et al. |
| 2013/0044042 | A1 | | 2/2013 | Olsson et al. |

FOREIGN PATENT DOCUMENTS

| | | |
|---|---|---|
| EP | 2275856 | 1/2011 |
| KR | 20090078085 | 7/2009 |

OTHER PUBLICATIONS

Response to Canadian Office Action dated Jan. 31, 2012, Canadian Patent Application No. 2,750,287 filed Aug. 29, 2011, 12 pages.

Canadian Office Action dated Feb. 22, 2012, Canadian Patent Application No. 2,750,287 filed Aug. 29, 2011, 1 page.

Response to Canadian Office Action dated Feb. 28, 2012, Canadian Patent Application No. 2,750,287 filed Aug. 29, 2011, 2 pages.

Preliminary Amendment dated Apr. 20, 2012, U.S. Appl. No. 13/221,739, filed Aug. 30, 2011, 10 pages.

Li, et al., "An Efficient Method for Eye Tracking and Eye-Gazed FOV Estimation," Proceedings of the 16th IEEE international conference on Image processing (ICIP'09), pp. 2597-2600, Nov. 2009, Cairo, Egypt, 4 pages.

Lin et al., "A new data processing and calibration method for an eye-tracking device pronunciation system," Optics & Laser Technology, Apr. 2002, vol. 34, pp. 405-413. Elsevier Science Ltd. New York, NY, USA, 9 pages.

Bagnell, C. Robert, Jr. "Pathology 464—Light Microscopy, Chapter 1—Parts", Class Notes, University of North Carolina School of Medicine, Jan. 2001 [retrieved on Feb. 2, 2011] Chapel Hill, North Carolina, USA. Retrieved from the Internet, URL: <http://www.med.unc.edu/microscopy/files/courses/light-microscopy/Chapter%201%20-%20Parts>, 8 pages.

Ramu, G. et al., "A Flexure-based Deployable Stereo Vision Mechanism and Temperature and Force Sensors for Laparoscopic Tools", Proceedings of the 14th National Conference on Machines and Mechanisms (NaCoMM09), Dec. 17-18, 2009, NIT, Durgapur, India, 6 pages.

ZionEyez, A Social Media Company [online], Copyright ZionEyez 2011 [retrieved on Jun. 15, 2011], Retrieved from the Internet: <URL:http://www.zioneyez.com/#/home/>, 6 pages.

Brudder, et al., "Estimation of Virtual Interpupillary Distances for Immersive Head-Mounted Displays", Proceedings of the 7th Symposium on Applied Perception in Graphics and Visualization (APGV '10), Association for Computing Machinery, Jul. 24-25, 2010, Los Angeles, California, USA, 1 page.

Livingston et al., "Vertical Vergence Calibration for Augmented Reality Displays", Proceedings of the IEEE Conference on Virtual Reality, pp. 293-294, Mar. 25-29, 2006, Alexandria, Virginia, USA, 2 pages.

Owen, et al, "Display-Relative Calibration for Optical See-Through Head-Mounted Displays", Proceedings of the Third IEEE and ACM International Symposium on Mixed and Augmented Reality (ISMAR 2004), Nov. 2-5, 2004, Arlington, Virginia, USA, 9 pages.

Pansing, et al., "Optimization of illumination schemes in a head-mounted display integrated with eye tracking capabilities", Proceedings of the SPIE International Society for Optical Engineering, vol. 5875, Aug. 2005, San Diego, California, USA, 13 pages.

Piantanida, Tom, "Another Look at HMD Safety", CyberEdge Journal, Nov./Dec. issue, 1993 [retrieved on Feb. 1, 2011] Retrieved from the Internet: URL<http://www.cyberedge.com/info_r_a%2Bp05_hmd-again.html>, 2 pages.

"Interpupillary Distance", Wikipedia, the free encyclopedia [online], [retrieved on May 17, 2011], Retrieved from the Internet: URL<http://en.wikipedia.org/wiki/Interpupillary_distance>, 3 pages.

"Pupillary Distance", Wikipedia, the free encyclopedia [online], [retrieved on May 13, 2011], Retrieved from the Internet: URL<http://en.wikipedia.org/wiki/Pupillary_distance>, 2 pages.

Hong, et al., "Modeling of an eye-imaging system for optimizing illumination schemes in an eye-tracked head-mounted display," Applied Optics, Nov. 2007, vol. 46, No. 31, Optical Society of America: Washington, DC, USA, 14 pages.

Thalheim, et al., "Body Check: Biometric Access Protection Devices and their Programs Put to the Test," c't magazin für computer technik, Nov. 2002, Hannover, Germany, 19 pages.

Davis, Amanda, "Sunglasses Block the Brightest of Light," LCD lenses and sensor eliminate glare, The Institute [online], IEEE, Nov. 4, 2011 [retrieved on Nov. 8, 2011], Retrieved from the Internet: <URL:http://theinstitute.ieee.org/technology-focus/technology-topic/sunglasses-block-the-brightest-of-light>, 5 pages.

U.S. Appl. No. 13/221,739, filed Aug. 30, 2011.
U.S. Appl. No. 13/221,707, filed Aug. 30, 2011.
U.S. Appl. No. 13/221,669, filed Aug. 30, 2011.
Office Action dated Sep. 6, 2012, U.S. Appl. No. 13/221,739, filed Aug. 30, 2011, 61 pages.

(56) References Cited

OTHER PUBLICATIONS

Office Action dated Sep. 14, 2012, U.S. Appl. No. 13/221,707, filed Aug. 30, 2011, 35 pages.
Response to Office Action filed Oct. 16, 2012, U.S. Appl. No. 13/221,739, filed Aug. 30, 2011, 12 pages.
English Abstract for KR20090078085 published Jul. 17, 2009.
International Search Report and Written Opinion of the International Searching Authority dated Feb. 26, 2013 in International Patent Application No. PCT/US2012/052806, 11 pages.
U.S. Appl. No. 13/844,453, filed Mar. 15, 2013.
U.S. Appl. No. 13/689,542, filed Nov. 29, 2012.
Notice if Allowance and Fee(s) Due dated Dec. 12, 2012, U.S. Appl. No. 13/221,739, filed Aug. 30, 2011, 11 pages.
Response to Office Action filed Jan. 14, 2013, U.S. Appl. No. 13/221,707, filed Aug. 30, 2011, 9 pages.
Office Action dated May 1, 2013 in U.S. Appl. No. 13/221,707, 26 pages.
International Search Report and Written Opinion of the International Searching Authority dated Feb. 27, 2013 in International Patent Application No. PCT/US2012/052839, 9 pages.
Lee et al., "Iris Recognition in Wearable Computer", in Zhang et al., Biometric Authentication, First International Conference, ICBA 2004, Jul. 15-17, 2004, vol. 3072 of Lecture Notes in Computer Science, pp. 475-483.
Response to Office Action filed Sep. 3, 2013 in U.S. Appl. No. 13/221,707, 11 pages.
Final Office Action dated Oct. 1, 2013 in U.S. Appl. No. 13/221,707, 16 pages.
Response to Office Action filed Feb. 3, 2014 in U.S. Appl. No. 13/221,707, 12 pages.
Office Action dated Sep. 6, 2013 in U.S. Appl. No. 13/941,439, 13 pages.
Response to Office Action filed Nov. 14, 2013 in U.S. Appl. No. 13/941,439, 10 pages.
Final Office Action dated Dec. 23, 2013 in U.S. Appl. No. 13/941,439, 14 pages.
Office ACtion dated Jun. 5, 2014, in U.S. Appl. No. 13/221,707, 17 pages.
First Office Action dated Jun. 23, 2014 in Chinese Patent Application No. 201210313552.9, with English Summary, 16 pages.
English Abstract of Chinese Patent Application No. 101542584A, published Sep. 23, 2009, 2 pages.
Notice of Allowance dated Sep. 5, 2014 in U.S. Appl. No. 13/941,439, 10 pages.
Response to Office Action filed Sep. 5, 2014 in U.S. Appl. No. 13/221,707, 13 pages.
Office Action dated Sep. 19, 2014 in U.S. Appl. No. 13/689,542, 78 pages.
Response to Office Action filed Oct. 16, 2014 in Chinese Patent Application No. 201210312701, with English Summary and Translation of the Amended Claims, 14 pages.
Response to Office Action filed Oct. 27, 2014 in Chinese Patent Application No. 201210313552.9, with English Summary, 4 pages.
First Office Action dated Jun. 4, 2014 in Chinese Patent Application No. 201210312701.X, with English Summary, 14 pages.
Notice of Allowance dated Nov. 19, 2014 in U.S. Appl. No. 13/844,453, filed Mar. 15, 2013, 52 pages.
Notice of Allowance dated Jan. 7, 2015 in U.S. Appl. No. 13/221,707, filed Aug. 30, 2011, 47 pages.
Response to Office Action dated Jan. 6, 2015 in U.S. Appl. No. 13/689,542, filed Nov. 29, 2012, 34 pages.
Final Office Action dated Mar. 19, 2015 in U.S. Appl. No. 13/689,542, filed Nov. 29, 2012, 45 pages.
Notice of Allowance dated Apr. 15, 2015 in U.S. Appl. No. 13/844,453, filed Mar. 15, 2013, 19 pages.
Office Action with English translation dated May 25, 2015 in Chinese Patent Application No. 201210312701.X, 10 pages.
Response to Office Action with English translation dated Jun. 8, 2015 in Chinese Patent Application No. 201210312701.X, 9 pages.
Office Action dated May 15, 2015 in European Patent Application No. 12827964.3, 5 pages.
Response to Office Action dated Jun. 11, 2015 in U.S. Appl. No. 13/689,542, 15 pages.
Office Action dated Sep. 14, 2015 in Chinese Patent Application No. 20120312701.X, 6 pages.
Notice of Allowance dated Jul. 29, 2015 in U.S. Appl. No. 13/689,542, 15 pages.

\* cited by examiner

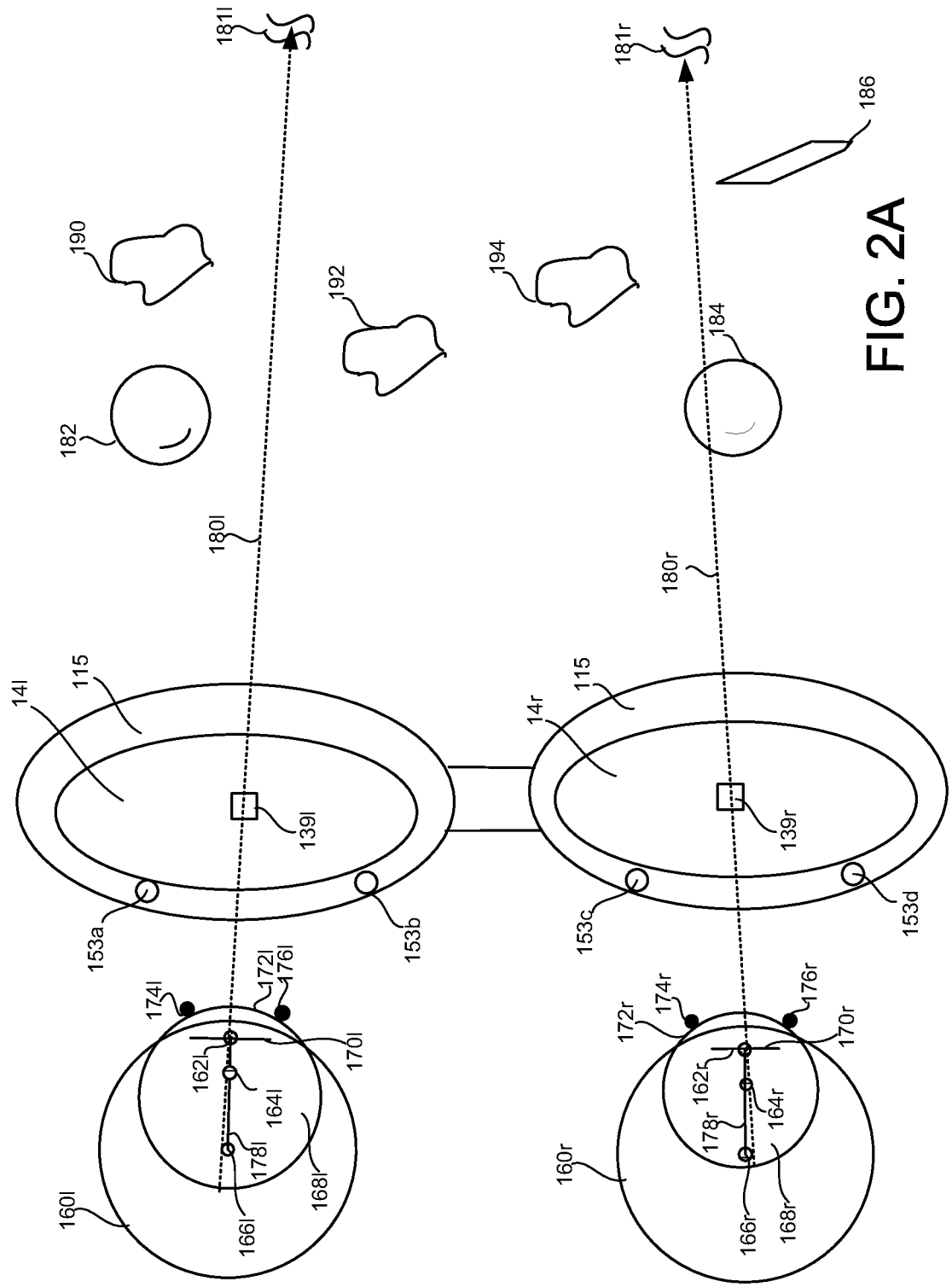

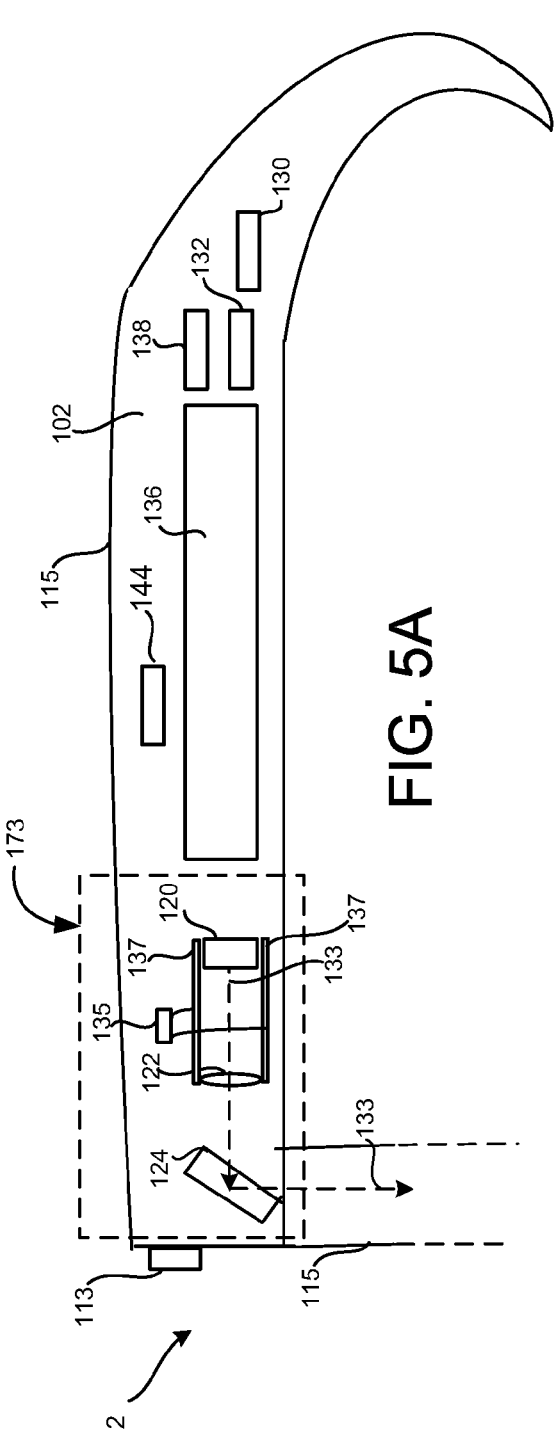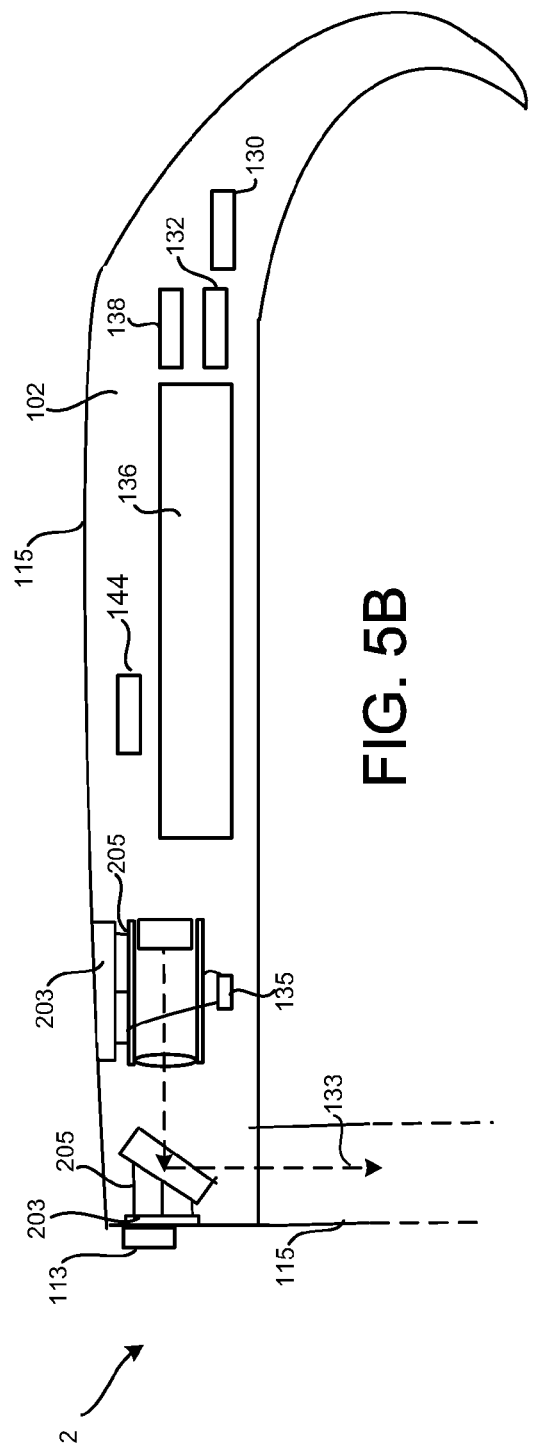

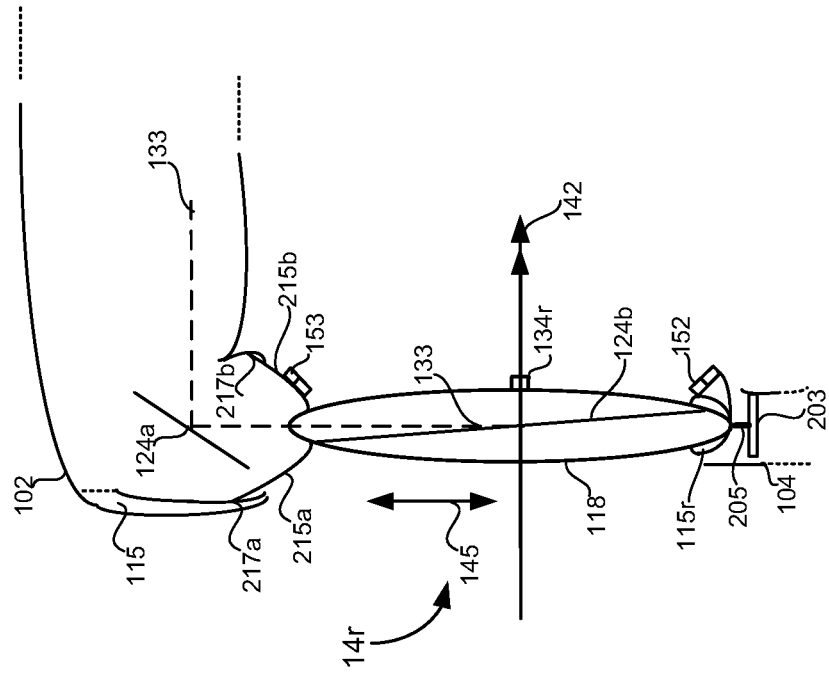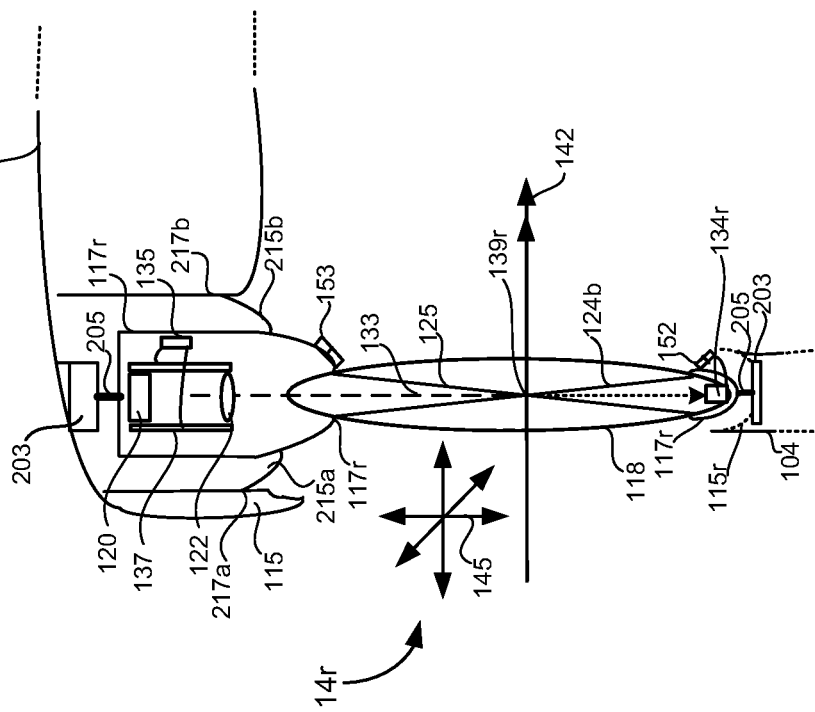

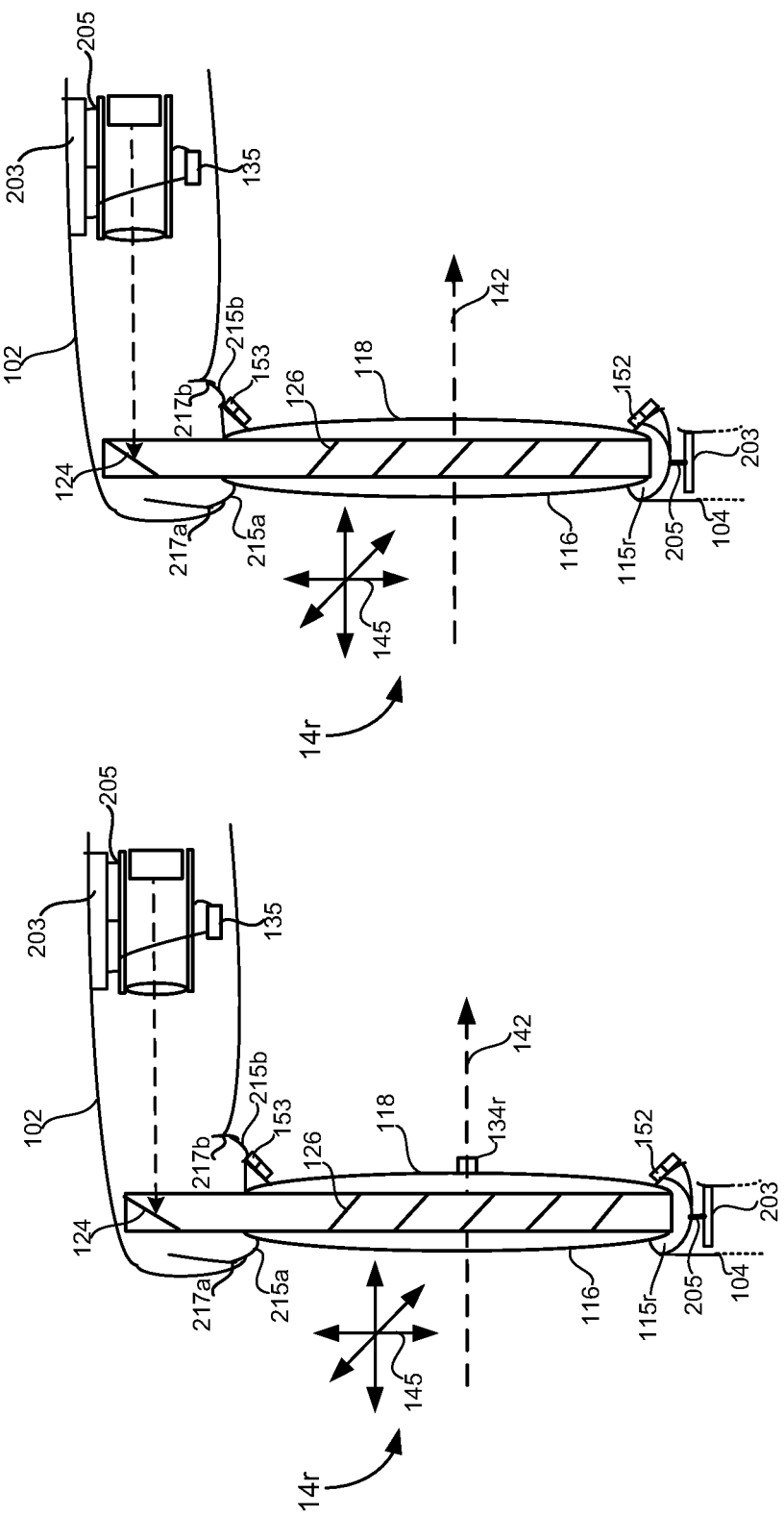

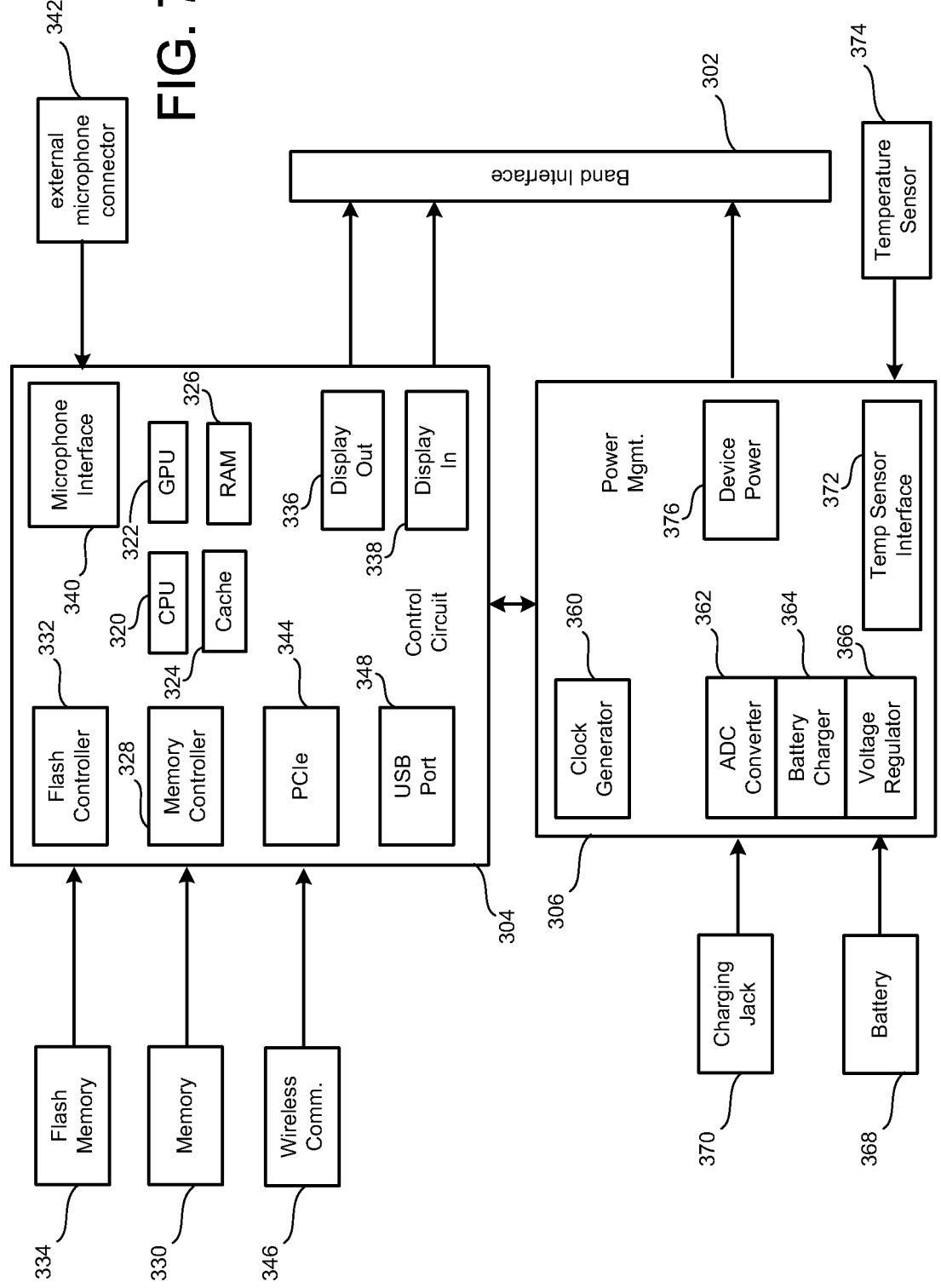

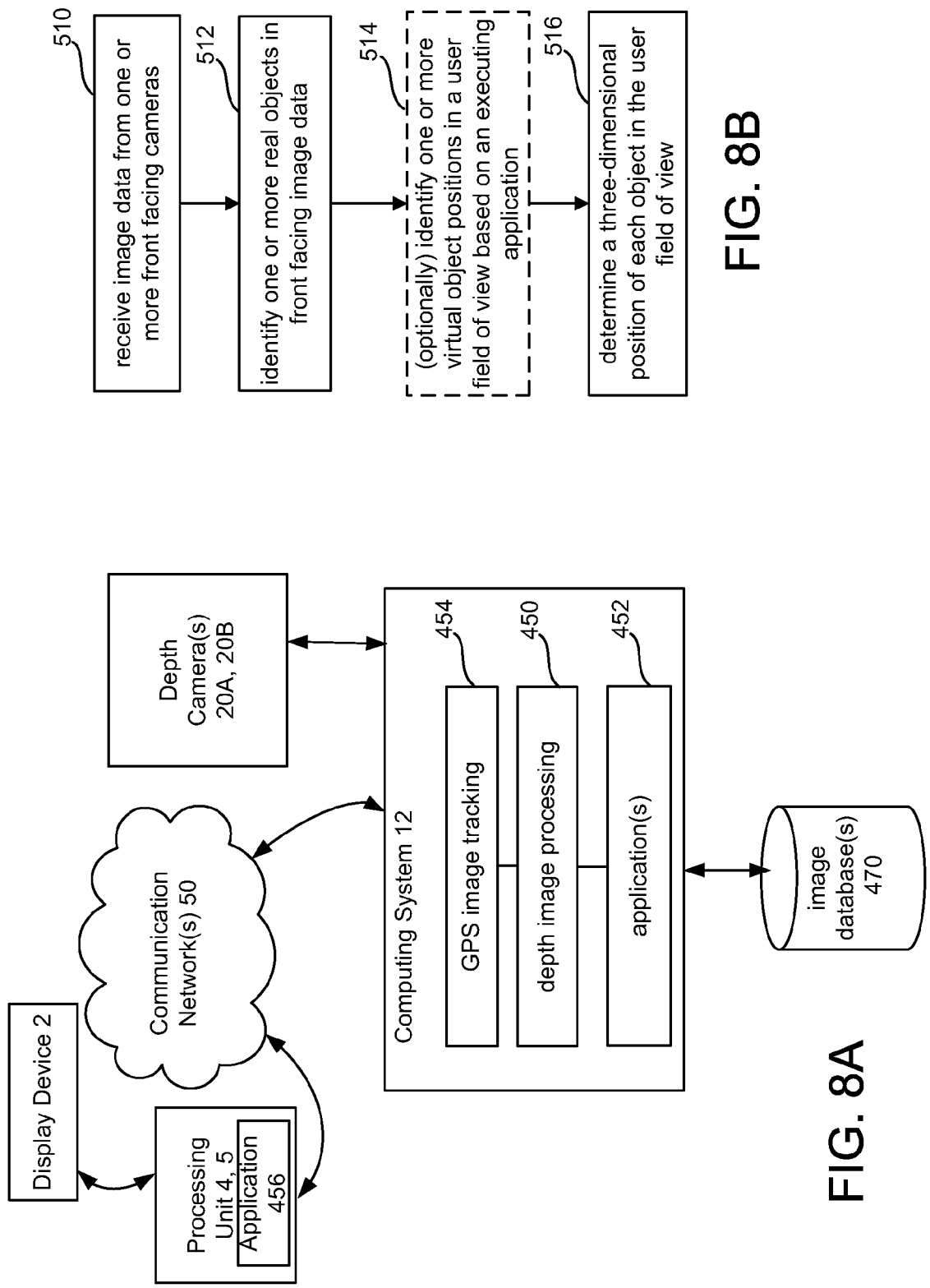

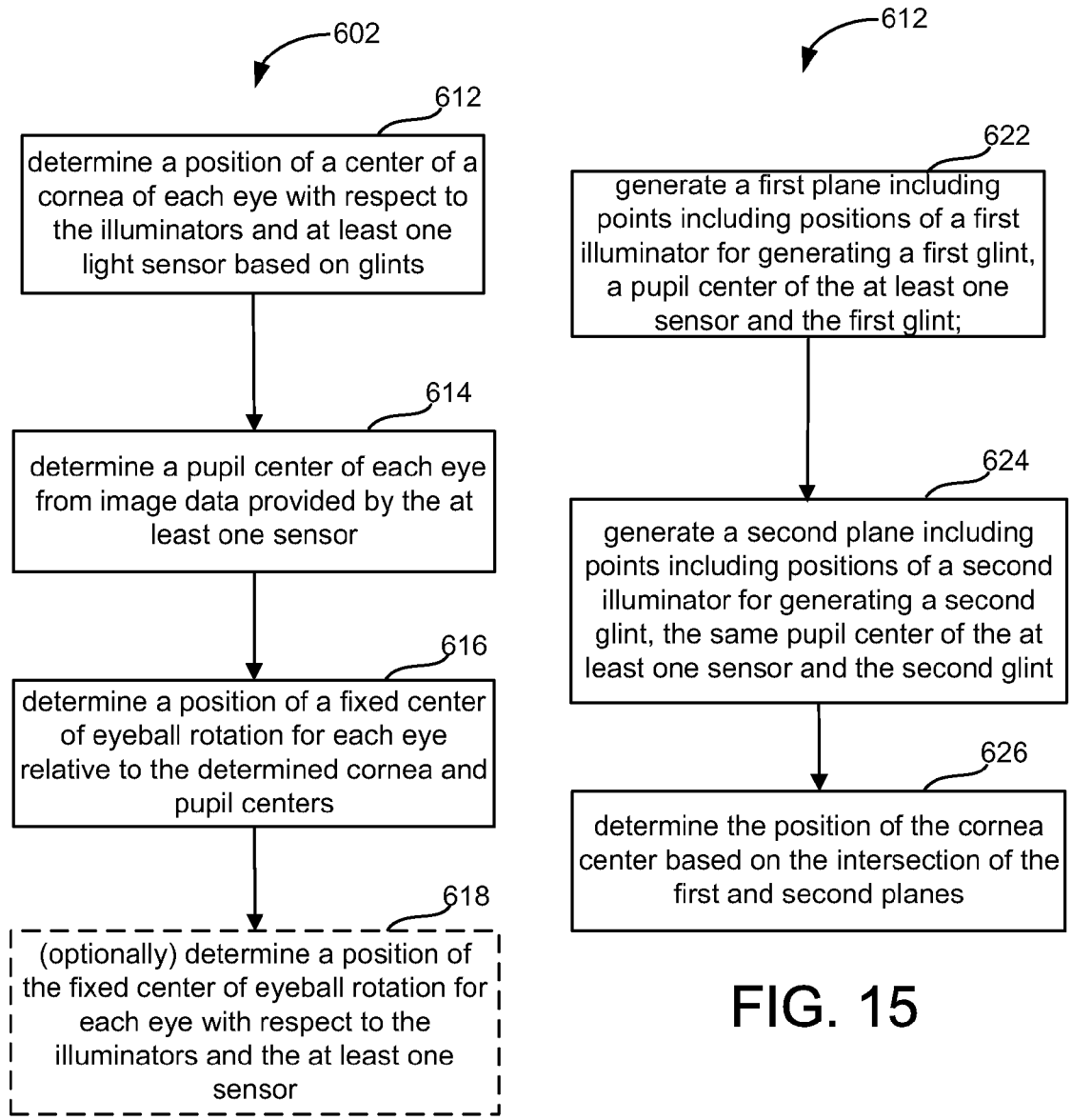

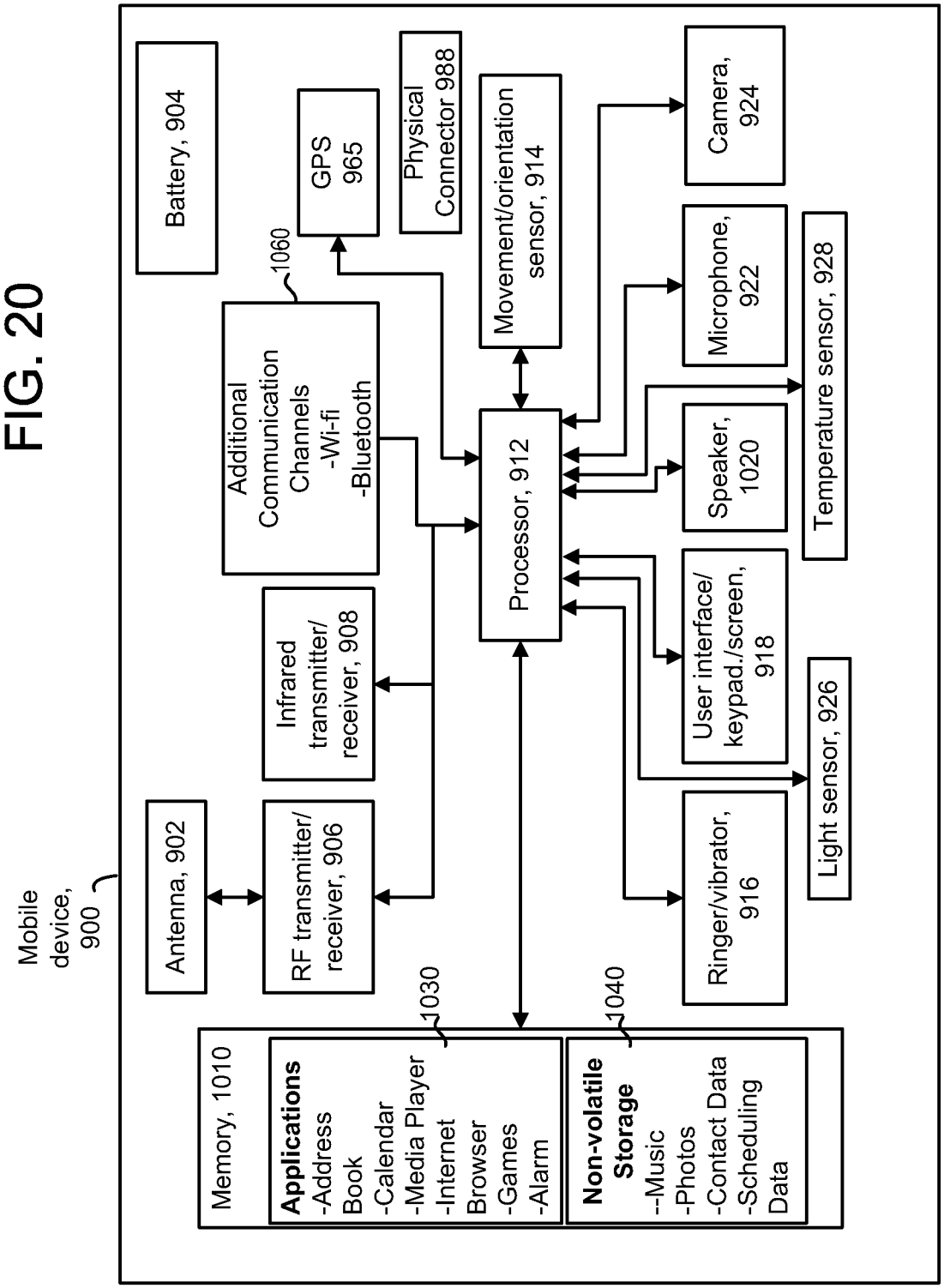

ALIGNING INTER-PUPILLARY DISTANCE IN A NEAR-EYE DISPLAY SYSTEM

BACKGROUND

Human vision is binocular, or involves two eyes, and near-eye viewing systems such as eyeglasses, binoculars and head mounted displays account for vision by two eyes wherein each line of sight originates from a different angle. Each eye is typically looking through its own lens or lens system. Ideally, every lens would provide perfectly collimated light providing a distortionless view no matter what portion of it the viewer looks through. However, that is not the case. Wearing a near-eye display device wherein the user's pupil is not aligned with a portion of the display providing collimated light causes visual discomfort because the eye muscles of the user's vergence system adapt to the display device optics.

Collimated light in a lens system is usually on its optical axis, and aligning each pupil with the respective optical axis relieves the visual discomfort. However, the distance between each person's pupils, his or her inter-pupillary distance (IPD), varies over about a 25 to 30 mm range in humans. A device with optical axes positioned at a distance suitable for one wearer will cause discomfort over time for another wearer having a different IPD.

SUMMARY

Technology provides various embodiments for automatically aligning a see-through, near-eye, mixed reality display device with an inter-pupillary distance (IPD) of one or more users. Alignment of an IPD for a user with respective display optical systems for each eye in the display device is automatically determined, and if the display device is not aligned with the user's IPD, the display device is automatically adjusted to bring it into alignment with the user IPD. The alignment determination as discussed further below in embodiments may be determined based on geometry of gaze detection elements on each display optical system and data captured by one or more sensors of the gaze detection elements. Furthermore, the alignment may be ascertained by determining whether the pupil of each eye is aligned with an optical axis of its respective display optical system as the inter-pupillary distance may be asymmetric with respect to a facial feature, for example, with respect to a nose of the user.

The technology provides an embodiment of a method for automatically aligning a see-through, near-eye, mixed reality display with an IPD. The method comprises automatically determining whether the see-through, near-eye, mixed reality display is aligned with a user IPD in accordance with an alignment critiera, and responsive to the display device not being aligned with the user IPD in accordance with the alignment criteria, automatically adjusting the display device for bringing the device into alignment with the user IPD.

The technology provides an embodiment of a system for automatically aligning a see-through, near-eye, mixed reality display with an IPD of a user. The system comprises a see-through, near-eye, mixed reality display device having a support structure including movable support structures. Attached to a respective movable support structure is a respective display optical system for each eye positioned to be seen through by the respective eye. Each display optical system has an optical axis. A display adjustment mechanism is also attached to at least one movable support structure for adjusting a position of the respective display optical system.

The system further comprises a respective arrangement of gaze detection elements. The gaze detection elements are positioned with respect to each display optical system on the respective movable support for forming a spatial relationship between the gaze detection elements and the respective eye. Each respective arrangement includes at least one respective sensor having a detection area for capturing data of the respective eye of the respective display optical system. A memory stores software and the captured data of each eye. One or more processors has access to the memory and is communicatively coupled to the display adjustment mechanism for automatically controlling adjustment of each display optical system for alignment with the inter-pupillary distance based on the captured data and the arrangement of gaze detection elements.

The technology provides an embodiment of a method for automatically aligning a see-through, near-eye, mixed reality display device with an inter-pupillary distance (IPD) of a user. The method embodiment comprises automatically determining whether the see-through, near-eye, mixed reality display is aligned with a user IPD in accordance with an alignment critiera, and responsive to the display device not being aligned with the user IPD in accordance with the alignment criteria, automatically adjusting the display device for bringing the device into alignment with the user IPD. The method embodiment further comprises detecting a change indicating an alignment with an IPD no longer satisfies an alignment criteria, and automatically re-adjusting at least one of the display optical systems for satisfying the alignment criteria.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 2A is a top view illustrating examples of gaze vectors extending to a point of gaze at a distance and a direction for aligning a far IPD.

FIG. 5A is a side view of an eyeglass temple in an eyeglasses embodiment of a mixed reality display device providing support for hardware and software components.

FIG. 5B is a side view of an eyeglass temple in an embodiment of a mixed reality display device providing support for hardware and software components and three dimensional adjustment of a microdisplay assembly.

FIG. 6A is a top view of an embodiment of a movable display optical system of a see-through, near-eye, mixed reality device including an arrangement of gaze detection elements.

FIG. 6B is a top view of another embodiment of a movable display optical system of a see-through, near-eye, mixed reality device including an arrangement of gaze detection elements.

FIG. 6C is a top view of a third embodiment of a movable display optical system of a see-through, near-eye, mixed reality device including an arrangement of gaze detection elements.

FIG. 6D is a top view of a fourth embodiment of a movable display optical system of a see-through, near-eye, mixed reality device including an arrangement of gaze detection elements.

FIG. 7B is a block diagram of one embodiment of the hardware and software components of a processing unit associated with a see-through, near-eye, mixed reality display unit.

FIG. 8A is a block diagram of a system embodiment for determining positions of objects within a user field of view of a see-through, near-eye, mixed reality display device.

FIG. 8B is a flowchart of a method embodiment for determining a three-dimensional user field of view of a see-through, near-eye, mixed reality display device.

FIG. 14 is a flowchart of a method embodiment which may be used to determine boundaries for a gaze detection coordinate system.

FIG. 15 is a flowchart illustrating a method embodiment for determining a position of a center of a cornea in the coordinate system with optical gaze detection elements of the see-through, near-eye, mixed reality display.

FIG. 20 is a block diagram of an exemplary mobile device which may operate in embodiments of the technology.

DETAILED DESCRIPTION

The inter-pupillary distance (IPD) typically refers to the horizontal distance between the user's pupils. The technology provides that the IPD may include a vertical or height dimension too. Many people have an IPD that is asymmetric with respect to their noses. For example, left eye is a little closer to the nose than the right eye.

A see-through, near-eye mixed reality display includes a display optical system for each eye which has an optical axis positioned to be seen through by the respective eye. The see-through, near-eye, mixed reality display device is aligned with the user's IPD, asymmetrical or not, when the optical axis of each display optical system is aligned with the respective pupil. If each pupil is not aligned within a criteria with the optical axis, the respective display optical system is automatically adjusted via a display adjustment mechanism until the alignment satisfies a criteria. An example of a criteria is a distance. When the pupils are satisfactorily aligned with the optical axes, the distance between the optical axes of the display optical systems represents the inter-pupillary distance (IPD), at least within a criteria, for example 1 mm.

For determining an IPD, one or more processors perform processing for drawing the user's focus to an object at a distance and direction for determining IPD. An example of such a direction is straight ahead in a user field of view. An example of such a distance is a distance of effective infinity at which a user's pupils have reached a separation horizontal distance used for viewing objects at infinity. For example, a distance at which most humans of the user's age and size appear to be looking straight ahead may be used. The IPD when a user is looking straight ahead is sometime referred to as the "far IPD." As discussed further below, some embodiments may determine both a near IPD and a far IPD. The near IPD is roughly 4 mm less than the far IPD and may be suitable when the user is viewing objects within a close distance, for example during reading.

In some of the embodiments below determining alignment with a user IPD, an arrangement of gaze detection elements positioned with respect to each display optical system provide a spatial relationship with respect to each eye and each other and includes one or more sensors for capturing data of each eye. Other gaze detection elements include illuminators, for example, IR illuminators for generating glints on a user's eyes. Based on the captured data and the spatial relationship to the eye and each other, an alignment of the optical axis of each display optical system with its respective pupil may be determined. One or more gaze vectors may form a basis for the alignment determination between pupil and optical axis in some examples. In others, a pupil position from image data or other sensor data in the context of the spatial relationship may form a basis for the alignment determination.

Figure 1A:
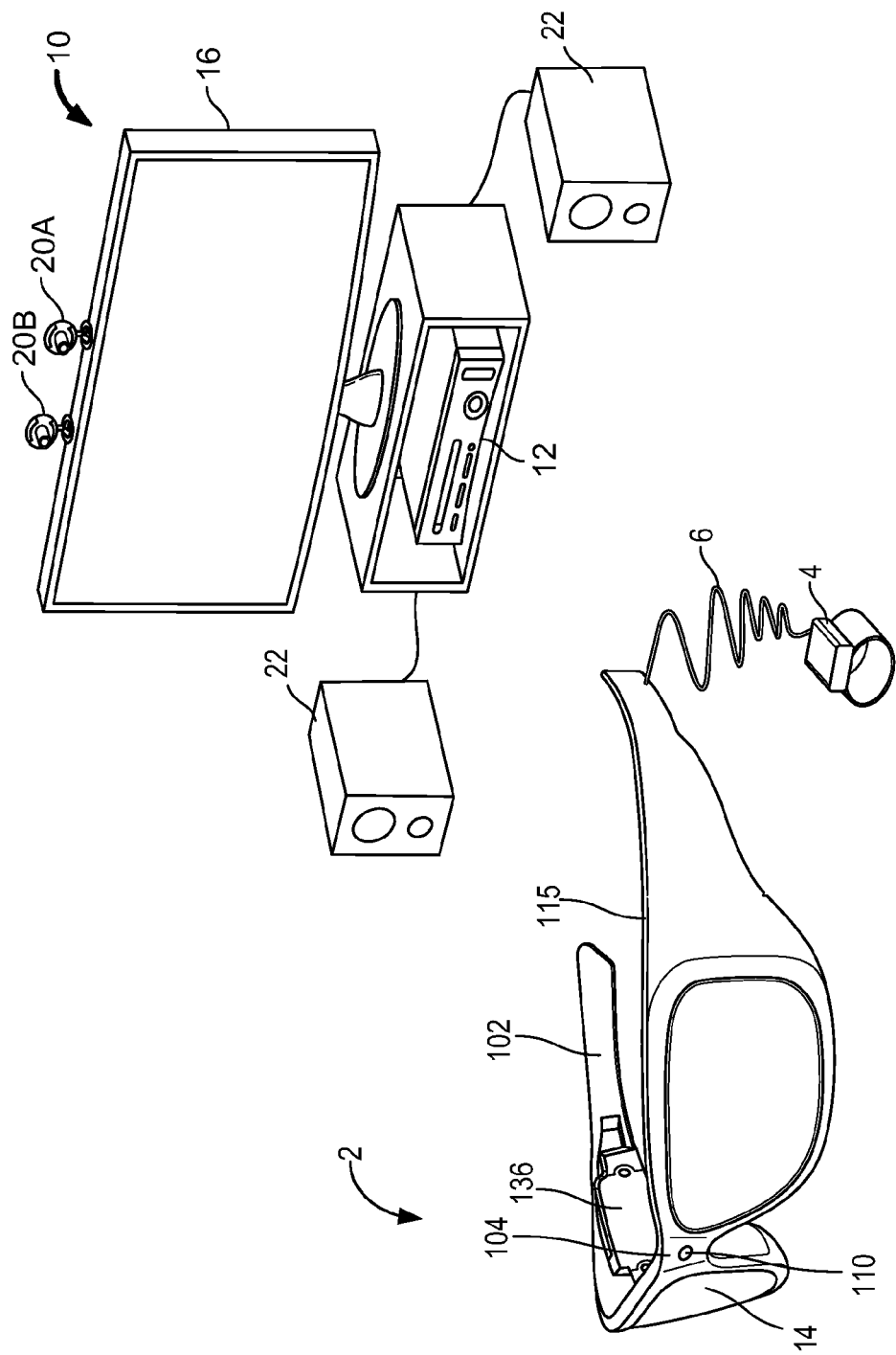
FIG. 1A is a block diagram depicting example components of one embodiment of a see-through, mixed reality display device with adjustable IPD in a system environment in which the device may operate.

FIG. 1A is a block diagram depicting example components of one embodiment of a see-through, mixed reality display device with adjustable IPD in a system environment in which the device may operate. System 10 includes a see-through display device as a near-eye, head mounted display device 2 in communication with processing unit 4 via wire 6. In other embodiments, head mounted display device 2 communicates with processing unit 4 via wireless communication. Processing unit 4 may take various embodiments. In some embodiments, processing unit 4 is a separate unit which may be worn on the user's body, e.g. the wrist in the illustrated example or in a pocket, and includes much of the computing power used to operate near-eye display device 2. Processing unit 4 may communicate wirelessly (e.g., WiFi, Bluetooth, infra-red, or other wireless communication means) to one or more hub computing systems 12. In other embodiments, the functionality of the processing unit 4 may be integrated in software and hardware components of the display device 2.

Head mounted display device 2, which in one embodiment is in the shape of eyeglasses in a frame 115, is worn on the head of a user so that the user can see through a display, embodied in this example as a display optical system 14 for each eye, and thereby have an actual direct view of the space in front of the user.

The use of the term "actual direct view" refers to the ability to see real world objects directly with the human eye, rather than seeing created image representations of the objects. For example, looking through glass at a room allows a user to have an actual direct view of the room, while viewing a video of a room on a television is not an actual direct view of the room. Based on the context of executing software, for example, a gaming application, the system can project images of virtual objects, sometimes referred to as virtual images, on the display that are viewable by the person wearing the see-through display device while that person is also viewing real world objects through the display.

Frame 115 provides a support for holding elements of the system in place as well as a conduit for electrical connections. In this embodiment, frame 115 provides a convenient eyeglass frame as support for the elements of the system discussed further below. In other embodiments, other support structures can be used. An example of such a structure is a visor or goggles. The frame 115 includes a temple or side arm for resting on each of a user's ears. Temple 102 is representative of an embodiment of the right temple and includes control circuitry 136 for the display device 2. Nose bridge 104 of the frame includes a microphone 110 for recording sounds and transmitting audio data to processing unit 4.

Hub computing system 12 may be a computer, a gaming system or console, or the like. According to an example embodiment, the hub computing system 12 may include hardware components and/or software components such that hub computing system 12 may be used to execute applications such as gaming applications, non-gaming applications, or the like. An application may be executing on hub computing system 12, the display device 2, as discussed below on a mobile device 5 or a combination of these.

Hub computing system 12 further includes one or more capture devices, such as capture devices 20A and 20B. In other embodiments, more or less than two capture devices can be used to capture the room or other physical environment of the user.

Capture devices 20A and 20B may be, for example, cameras that visually monitor one or more users and the surrounding space such that gestures and/or movements performed by the one or more users, as well as the structure of the surrounding space, may be captured, analyzed, and tracked to perform one or more controls or actions within an application and/or animate an avatar or on-screen character. Hub computing system 12 may be connected to an audiovisual device 16 such as a television, a monitor, a high-definition television (HDTV), or the like that may provide game or application visuals. In some instances, the audiovisual device 16 may be a three-dimensional display device. In one example, audiovisual device 16 includes internal speakers. In other embodiments, audiovisual device 16, a separate stereo or hub computing system 12 is connected to external speakers 22.

Figure 1B:
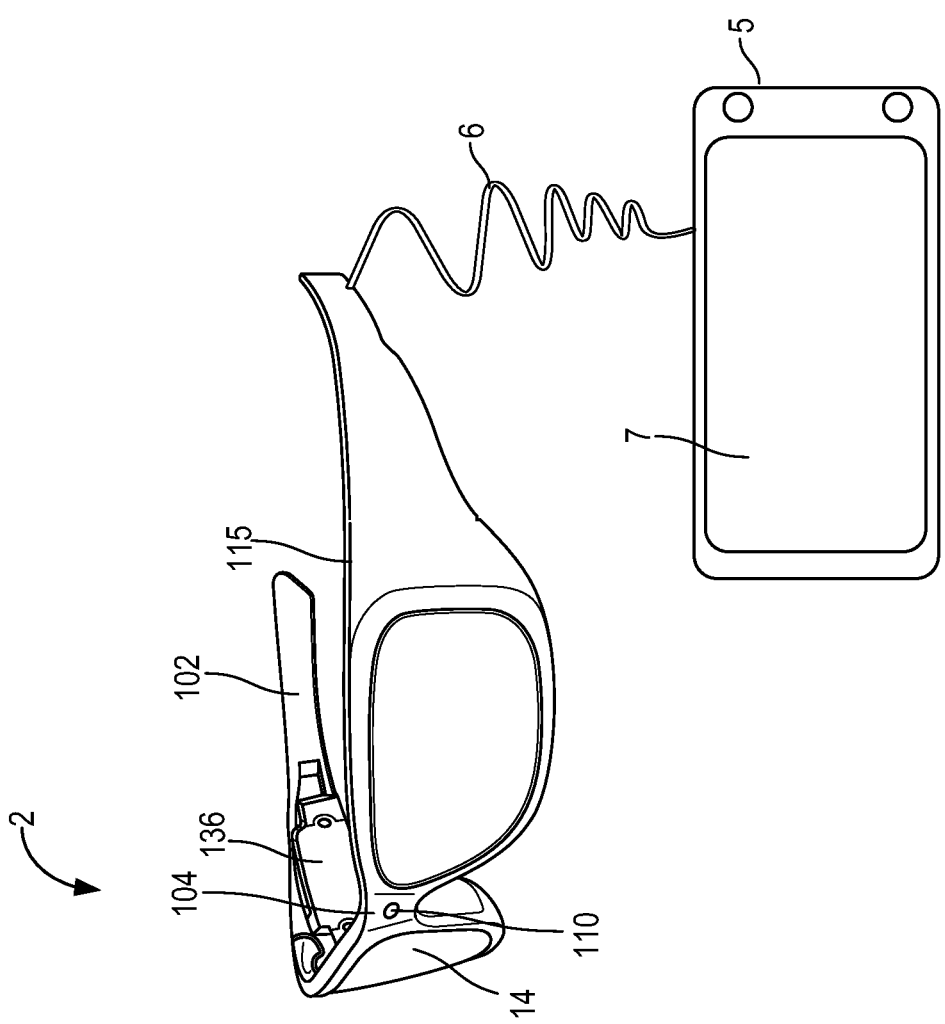
FIG. 1B is a block diagram depicting example components of another embodiment of a see-through, mixed reality display device with adjustable IPD.

FIG. 1B is a block diagram depicting example components of another embodiment of a see-through, mixed reality display device with adjustable IPD. In this embodiment, the near-eye display device 2 communicates with a mobile computing device 5 as an example embodiment of the processing unit 4. In the illustrated example, the mobile device 5 communicates via wire 6, but communication may also be wireless in other examples.

Furthermore, as in the hub computing system 12, gaming and non-gaming applications may execute on a processor of the mobile device 5 which user actions control or which user actions animate an avatar as may be displayed on a display 7 of the device 5. The mobile device 5 also provides a network interface for communicating with other computing devices like hub computing system 12 over the Internet or via another communication network via a wired or wireless communication medium using a wired or wireless communication protocol. A remote network accessible computer system like hub computing system 12 may be leveraged for processing power and remote data access by a processing unit 4 like mobile device 5. Examples of hardware and software components of a mobile device 5 such as may be embodied in a smartphone or tablet computing device are described in FIG. 20, and these components can embody the hardware and software components of a processing unit 4 such as those discussed in the embodiment of FIG. 7A. Some other examples of mobile devices 5 are a laptop or notebook computer and a netbook computer.

In some embodiments, gaze detection of each of a user's eyes is based on a three dimensional coordinate system of gaze detection elements on a near-eye, mixed reality display device like the eyeglasses 2 in relation to one or more human eye elements such as a cornea center, a center of eyeball rotation and a pupil center. Examples of gaze detection elements which may be part of the coordinate system including glint generating illuminators and at least one sensor for capturing data representing the generated glints. As discussed below (see FIG. 16 discussion), a center of the cornea can be determined based on two glints using planar geometry. The center of the cornea links the pupil center and the center of rotation of the eyeball, which may be treated as a fixed location for determining an optical axis of the user's eye at a certain gaze or viewing angle.

FIG. 2A is a top view illustrating examples of gaze vectors extending to a point of gaze at a distance and direction for aligning a far IPD. FIG. 2A illustrates examples of gaze vectors intersecting at a point of gaze where a user's eyes are focused effectively at infinity, for example beyond five (5) feet, or, in other words, examples of gaze vectors when the user is looking straight ahead. A model of the eyeball 160*l*, 160*r* is illustrated for each eye based on the Gullstrand schematic eye model. For each eye, an eyeball 160 is modeled as a sphere with a center of rotation 166 and includes a cornea 168 modeled as a sphere too and having a center 164. The cornea rotates with the eyeball, and the center 166 of rotation of the eyeball may be treated as a fixed point. The cornea covers an iris 170 with a pupil 162 at its center. In this example, on the surface 172 of the respective cornea are glints 174 and 176.

In the illustrated embodiment of FIG. 2A, a sensor detection area 139 is aligned with the optical axis of each display optical system 14 within an eyeglass frame 115. The sensor associated with the detection area is a camera in this example capable of capturing image data representing glints 174*l* and 176*l* generated respectively by illuminators 153*a* and 153*b* on the left side of the frame 115 and data representing glints 174*r* and 176*r* generated respectively by illuminators 153*c* and 153*d*. Through the display optical systems, 14*l* and 14*r* in the eyeglass frame 115, the user's field of view includes both real objects 190, 192 and 194 and virtual objects 182, 184, and 186.

The axis 178 formed from the center of rotation 166 through the cornea center 164 to the pupil 162 is the optical axis of the eye. A gaze vector 180 is sometimes referred to as the line of sight or visual axis which extends from the fovea through the center of the pupil 162. The fovea is a small area of about 1.2 degrees located in the retina. The angular offset between the optical axis computed in the embodiment of FIG. 14 and the visual axis has horizontal and vertical components. The horizontal component is up to 5 degrees from the optical axis, and the vertical component is between 2 and 3 degrees. In many embodiments, the optical axis is determined and a small correction is determined through user calibration to obtain the visual axis which is selected as the gaze vector. For each user, a virtual object may be displayed by the display device at each of a number of predetermined positions at different horizontal and vertical positions. An optical axis may be computed for each eye during display of the object at each position, and a ray modeled as extending from the position into the user eye. A gaze offset angle with horizontal and vertical components may be determined based on how the optical axis must be moved to align with the modeled ray. From the different positions, an average gaze offset angle with horizontal or vertical components can be selected as the small correction to be applied to each computed optical axis. In some embodiments, only a horizontal component is used for the gaze offset angle correction.

The visual axes 180*l* and 180*r* illustrate that the gaze vectors are not perfectly parallel as the vectors become closer together as they extend from the eyeball into the field of view at a point of gaze which is effectively at infinity as indicated by the symbols 181*l* and 181*r*. At each display optical system 14, the gaze vector 180 appears to intersect the optical axis upon which the sensor detection area 139 is centered. In this configuration, the optical axes are aligned with the interpupillary distance (IPD). When a user is looking straight ahead, the IPD measured is also referred to as the far IPD.

When identifying an object for a user to focus on for aligning IPD at a distance, the object may be aligned in a direction along each optical axis of each display optical system. Initially, the alignment between the optical axis and user's pupil is not known. For a far IPD, the direction may be straight ahead through the optical axis. When aligning near IPD, the identified object may be in a direction through the optical axis, however due to vergence of the eyes necessary for close distances, the direction is not straight ahead although it may be centered between the optical axes of the display optical systems.

Figure 2B:
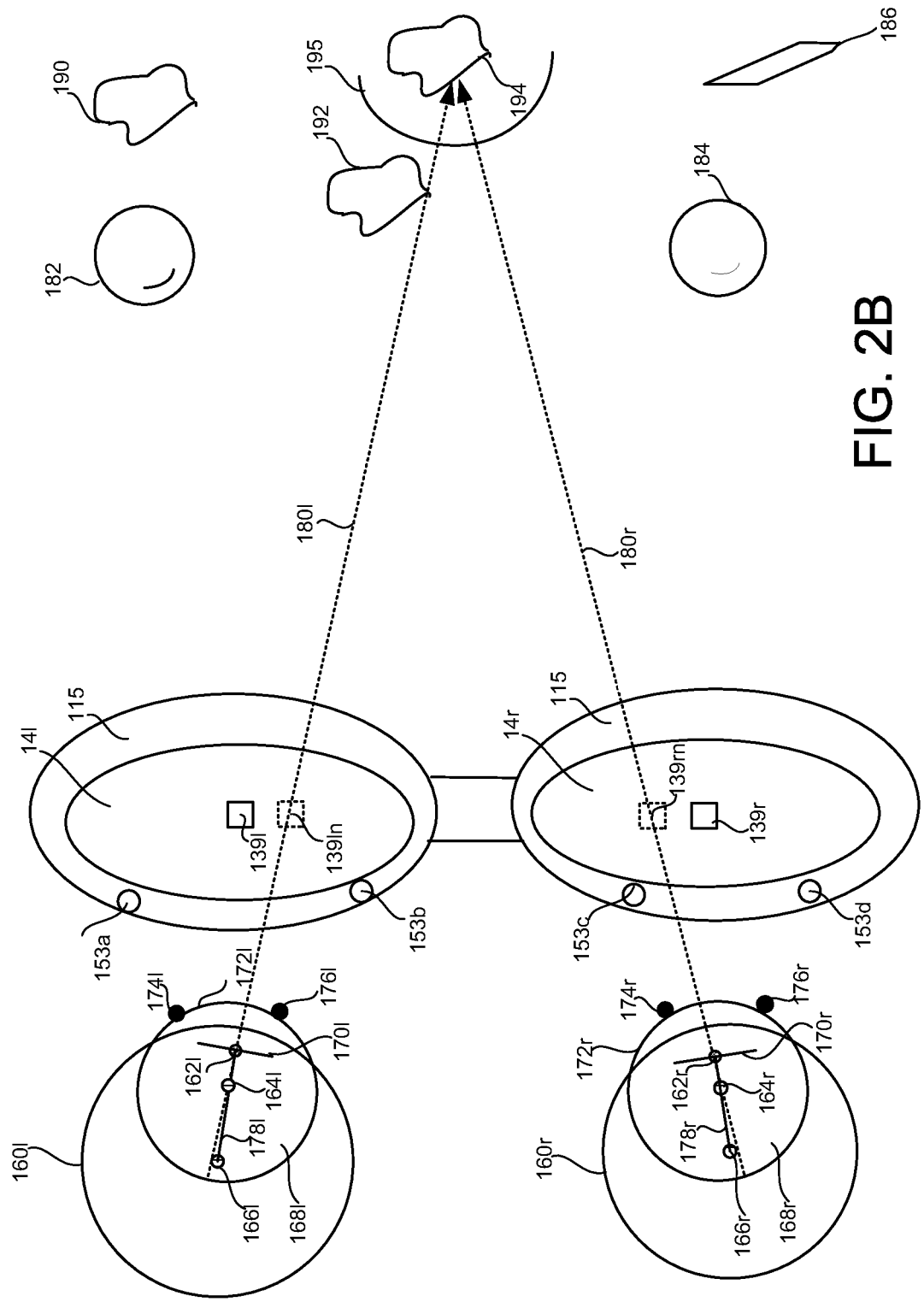
FIG. 2B is a top view illustrating examples of gaze vectors extending to a point of gaze at a distance and a direction for aligning a near IPD.

FIG. 2B is a top view illustrating examples of gaze vectors extending to a point of gaze at a distance and a direction for aligning a near IPD. In this example, the cornea 168*l* of the left eye is rotated to the right or towards the user's nose, and the cornea 168*r* of the right eye is rotated to the left or towards the user's nose. Both pupils are gazing at a real object 194 at a much closer distance, for example two (2) feet in front of the user. Gaze vectors 180*l* and 180*r* from each eye enter the Panum's fusional region 195 in which real object 194 is located. The Panum's fusional region is the area of single vision in a binocular viewing system like that of human vision. The intersection of the gaze vectors 180*l* and 180*r* indicates that the user is looking at real object 194. At such a distance, as the eyeballs rotate inward, the distance between their pupils decreases to a near IPD. The near IPD is typically about 4 mm less than the far IPD. A near IPD distance criteria, e.g. a point of gaze at less than four feet for example, may be used to switch or adjust the IPD alignment of the display optical systems 14 to that of the near IPD. For the near IPD, each display optical system 14 may be moved toward the user's nose so the optical axis, and detection area 139, moves toward the nose a few millimeters as represented by detections area 139*ln* and 139*rn*.

Users do not typically know their IPD data. The discussion below illustrates some embodiments of methods and systems for determining the IPD for the user, and adjusting the display optical systems accordingly.

Figure 3:
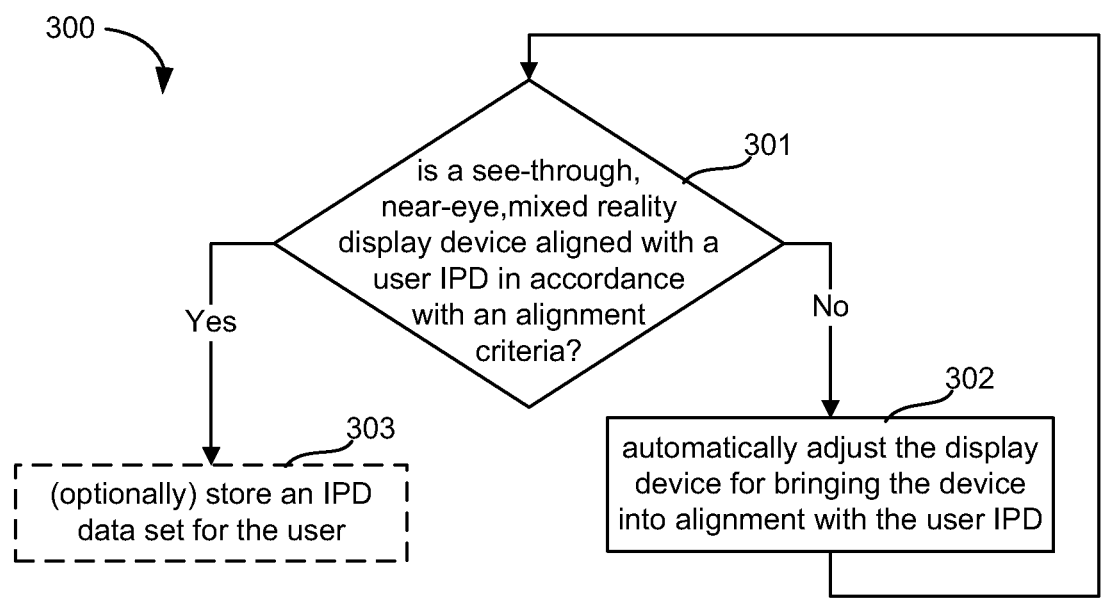
FIG. 3 is a flowchart of a method embodiment for automatically aligning a see-through, near-eye, mixed reality display with an IPD.

FIG. 3 is a flowchart of a method embodiment 300 for automatically aligning a see-through, near-eye, mixed reality display with an IPD. In step 301, one or more processors of the control circuitry 136, e.g. processor 210 in FIG. 7A below, the processing unit 4, 5, the hub computing system 12 or a combination of these automatically determines whether a see-through, near-eye, mixed reality display device is aligned with an IPD of a user in accordance with an alignment criteria. If not, in step 302, the one or more processors automatically cause adjustment of the display device by at least one display adjustment mechanism for bringing the device into alignment with the user IPD. If it is determined the see-through, near-eye, mixed reality display device is in alignment with a user IPD, optionally, in step 303 an IPD data set is stored for the user. In some embodiments, a display device 2 may automatically determine IPD every time anyone puts on the display device 2. However, as IPD data is generally fixed for adults, due to the confines of the human skull, an IPD data set may be determined typically once and stored for each user. The stored IPD data set may at least be used as an initial setting for a display device with which to begin an IPD alignment check.

A display device 2 has a display optical system for each eye, and in some embodiments, the one or more processors store the IPD as the distance between the optical axes of the display optical systems at positions which satisfy the alignment criteria. In some embodiments, the one or more processors store the position of each optical axis in the IPD data set. The IPD for a user may be asymmetrical, for example with respect to the user's nose. For instance, the left eye is a little closer to the nose than the right eye is. In one example, adjustment values of a display adjustment mechanism for each display optical system from an initial position may be saved in the IPD data set. The initial position of the display adjustment mechanism may have a fixed position with respect to a stationary frame portion, for example a point on the bridge 104. Based on this fixed position with respect to the stationary frame portion, and the adjustment values for one or more directions of movement, a position of each optical axis with respect to the stationary frame portion may be stored as a pupil alignment position for each display optical system. Additionally, in the case of the stationary frame portion being a point on the bridge, a position vector of the respective pupil to the user's nose may be estimated for each eye based on the fixed position to the point on the bridge and the adjustment values. The two position vectors for each eye provide at least horizontal distance components, and can include vertical distance components as well. An inter-pupillary distance IPD in one or more directions may be derived from these distance components.

Figure 4A:
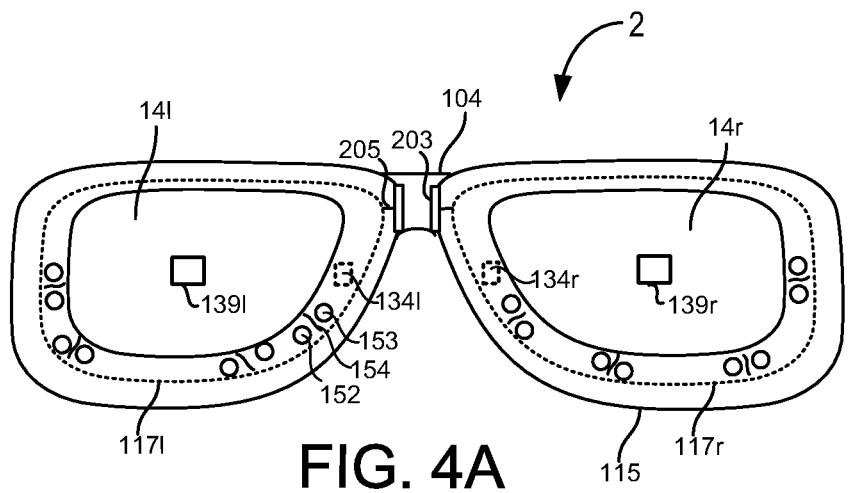
FIG. 4A illustrates an exemplary arrangement of a see through, near-eye, mixed reality display device embodied as eyeglasses with movable display optical systems including gaze detection elements.

FIG. 4A illustrates an exemplary arrangement of a see through, near-eye, mixed reality display device embodied as eyeglasses with movable display optical systems including gaze detection elements. What appears as a lens for each eye represents a display optical system 14 for each eye, e.g. 14r and 14l. A display optical system includes a see-through lens, e.g. 118 and 116 in FIGS. 6A-6D, as in an ordinary pair of glasses, but also contains optical elements (e.g. mirrors, filters) for seamlessly fusing virtual content with the actual direct real world view seen through the lenses 118, 116. A display optical system 14 has an optical axis which is generally in the center of the see-through lens 118, 116 in which light is generally collimated to provide a distortionless view. For example, when an eye care professional fits an ordinary pair of eyeglasses to a user's face, a goal is that the glasses sit on the user's nose at a position where each pupil is aligned with the center or optical axis of the respective lens resulting in generally collimated light reaching the user's eye for a clear or distortionless view.

In the example of FIG. 4A, a detection area 139r, 139l of at least one sensor is aligned with the optical axis of its respective display optical system 14r, 14l so that the center of the detection area 139r, 139l is capturing light along the optical axis. If the display optical system 14 is aligned with the user's pupil, each detection area 139 of the respective sensor 134 is aligned with the user's pupil. Reflected light of the detection area 139 is transferred via one or more optical elements to the actual image sensor 134 of the camera, in this example illustrated by dashed line as being inside the frame 115.

In one example, a visible light camera also commonly referred to as an RGB camera may be the sensor, and an example of an optical element or light directing element is a visible light reflecting mirror which is partially transmissive and partially reflective. The visible light camera provides image data of the pupil of the user's eye, while IR photodetectors 152 capture glints which are reflections in the IR portion of the spectrum. If a visible light camera is used, reflections of virtual images may appear in the eye data captured by the camera. An image filtering technique may be used to remove the virtual image reflections if desired. An IR camera is not sensitive to the virtual image reflections on the eye.

In other examples, the at least one sensor 134 is an IR camera or a position sensitive detector (PSD) to which the IR radiation may be directed. For example, a hot reflecting surface may transmit visible light but reflect IR radiation. The IR radiation reflected from the eye may be from incident radiation of the illuminators 153, other IR illuminators (not shown) or from ambient IR radiation reflected off the eye. In some examples, sensor 134 may be a combination of an RGB and an IR camera, and the light directing elements may include a visible light reflecting or diverting element and an IR radiation reflecting or diverting element. In some examples, a camera may be small, e.g. 2 millimeters (mm) by 2 mm. An example of such a camera sensor is the Omnivision OV7727. In other examples, the camera may be small enough, e.g. the Omnivision OV7727, e.g. that the image sensor or camera 134 may be centered on the optical axis or other location of the display optical system 14. For example, the camera 134 may be embedded within a lens of the system 14. Additionally, an image filtering technique may be applied to blend the camera into a user field of view to lessen any distraction to the user.

In the example of FIG. 4A, there are four sets of an illuminator 153 paired with a photodetector 152 and separated by a barrier 154 to avoid interference between the incident light generated by the illuminator 153 and the reflected light received at the photodetector 152. To avoid unnecessary clutter in the drawings, drawing numerals are shown with respect to a representative pair. Each illuminator may be an infra-red (IR) illuminator which generates a narrow beam of light at about a predetermined wavelength. Each of the photodetectors may be selected to capture light at about the predetermined wavelength. Infra-red may also include near-infrared. As there can be wavelength drift of an illuminator or photodetector or a small range about a wavelength may be acceptable, the illuminator and photodetector may have a tolerance range about a wavelength for generation and detection. In embodiments where the sensor is an IR camera or IR position sensitive detector (PSD), the photodetectors may be additional data capture devices and may also be used to monitor the operation of the illuminators, e.g. wavelength drift, beam width changes, etc. The photodetectors may also provide glint data with a visible light camera as the sensor 134.

As described below, in some embodiments which calculate a cornea center as part of determining a gaze vector, two glints, and therefore two illuminators will suffice. However, other embodiments may use additional glints in determining a pupil position and hence a gaze vector. As eye data representing the glints is repeatedly captured, for example at 30 frames a second or greater, data for one glint may be blocked by an eyelid or even an eyelash, but data may be gathered by a glint generated by another illuminator.

In FIG. 4A, each display optical system 14 and its arrangement of gaze detection elements facing each eye such as camera 134 and its detection area 139, optical alignment elements (not shown in this figure; see 6A-6D below), the illuminators 153 and photodetectors 152 are located on a movable inner frame portion 117l, 117r. In this example, a display adjustment mechanism comprises one or more motors 203 having a shaft 205 which attaches to an object for pushing and pulling the object in at least one of three dimensions. In this example, the object is the inner frame portion 117 which slides from left to right or vise versa within the frame 115 under the guidance and power of shafts 205 driven by motors 203. In other embodiments, one motor 203 may drive both inner frames. As discussed with reference to FIGS. 5A and 5B, a processor of control circuitry 136 of the display device 2 is able to connect to the one or more motors 203 via electrical connections within the frame 115 for controlling adjustments in different directions of the shafts 205 by the motors 203. Furthermore, the motors 203 access a power supply via the electrical connections of the frame 115 as well.

Figure 4B:
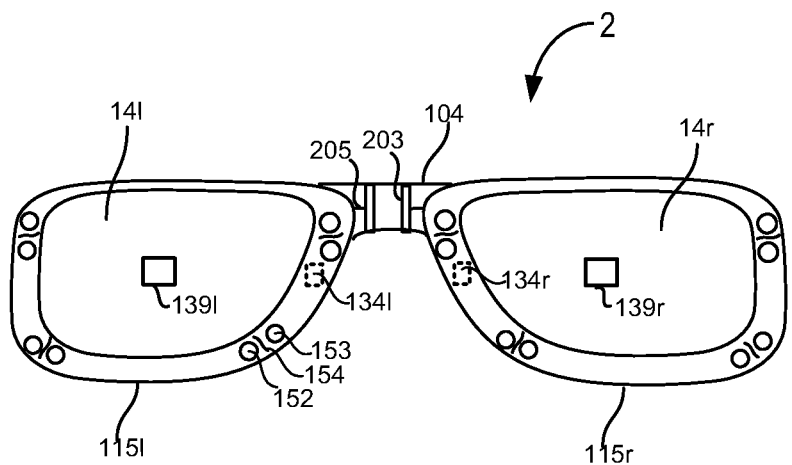
FIG. 4B illustrates another exemplary arrangement of a see through, near-eye, mixed reality display device embodied as eyeglasses with movable display optical systems including gaze detection elements.

FIG. 4B illustrates another exemplary arrangement of a see through, near-eye, mixed reality display device embodied as eyeglasses with movable display optical systems including gaze detection elements. In this embodiment, each display optical system 14 is enclosed in a separate frame portion 115*l*, 115*r*, e.g. a separate eyeglass framed section, which is movable individually by the motors 203. In some embodiments, the movement range in any dimension is less than 10 millimeters. In some embodiments, the movement range is less than 6 millimeters depending on the range of frame sizes offered for a product. For the horizontal direction, moving each frame a few millimeters left or right will not impact significantly the width between the eyeglass temples, e.g. 102, which attach the display optical systems 14 to the user's head. Additionally, in this embodiment, two sets of illuminator 153 and photodetector 152 pairs are positioned near the top of each frame portion 115*l*, 115*r* for illustrating another example of a geometrical relationship between illuminators and hence the glints they generate. This arrangement of glints may provide more information on a pupil position in the vertical direction. In other embodiments like that in FIG. 4A where the illuminators are closer to one side of the frame portions 115*l*, 115*r*, 117*l*, 117*r*, the illuminators 153 may be positioned at different angles with respect to the frame portion for directing light at different portions of the eye, for also obtaining more vertical and horizontal components for identifying a pupil position.

Figure 4C:
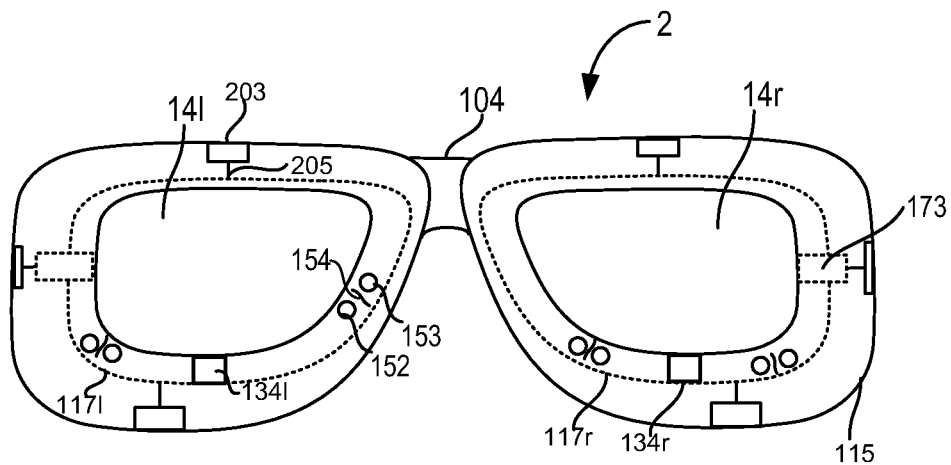
FIG. 4C illustrates yet another exemplary arrangement of a see through, near-eye, mixed reality display device embodied as eyeglasses with movable display optical systems including gaze detection elements.

FIG. 4C illustrates another exemplary arrangement of a see through, near-eye, mixed reality display device embodied as eyeglasses with movable display optical systems including gaze detection elements. In this example, the sensor 134*r*, 134*l* is in line or aligned with the optical axis at about the center of its respective display optical system 14*r*, 14*l* but located on the frame 115 below the system 14. Additionally, in some embodiments, the camera 134 may be a depth camera or include a depth sensor. In this example, there are two sets of illuminators 153 and photodetectors 152.

An inter-pupillary distance may describe the distance between a user's pupils in a horizontal direction, but vertical differences may also be determined. Additionally, moving a display optical system in a depth direction between the eye and the display device 2 may also assist in aligning the optical axis with the user's pupil. A user may actually have different depths of their eyeballs within the skull. Movement of the display device in the depth direction with respect to the head may also introduce misalignment between the optical axis of the display optical system 14 and its respective pupil.

In this example, the motors form an example of a XYZ transport mechanism for moving each display optical system 14 in three dimensions. The motors 203 in this example are located on the outer frame 115 and their shafts 205 are attached to the top and bottom of the respective inner frame portion 117. The operation of the motors 203 are synchronized for their shaft movements by the control circuitry 136 processor 210. Additionally, as this is a mixed reality device, each image generation unit like microdisplay assembly 173 for creating images of virtual objects or virtual images for display in the respective display optical system 14 is moved by a motor and shaft as well to maintain optical alignment with the display optical system. Examples of microdisplay assemblies 173 are described further below. In this example, the motors 203 are three axis motors or can move their shafts in three dimensions. For example, the shaft may be pushed and pulled in one axis of direction along a center of a crosshair guide and move in each of two perpendicular directions in the same plane within the perpendicular openings of the cross-hair guide.

FIG. 5A is a side view of an eyeglass temple 102 of the frame 115 in an eyeglasses embodiment of a see-through, mixed reality display device providing support for hardware and software components. At the front of frame 115 is physical environment facing video camera 113 that can capture video and still images. Particularly in embodiments where the display device 2 is not operating in conjunction with depth cameras like capture devices 20*a* and 20*b* of the hub system 12, the physical environment facing camera 113 may be a depth camera as well as a visible light sensitive camera. For example, the depth camera may include an IR illuminator transmitter and a hot reflecting surface like a hot mirror in front of the visible image sensor which lets the visible light pass and directs reflected IR radiation within a wavelength range or about a predetermined wavelength transmitted by the illuminator to a CCD or other type of depth sensor. The data from the sensors may be sent to a processor 210 of the control circuitry 136, or the processing unit 4,5 or both which may process them but which the unit 4,5 may also send to a computer system over a network or hub computing system 12 for processing. The processing identifies objects through image segmentation and edge detection techniques and maps depth to the objects in the user's real world field of view. Additionally, the physical environment facing camera 113 may also include a light meter for measuring ambient light.

Control circuits 136 provide various electronics that support the other components of head mounted display device 2. More details of control circuits 136 are provided below with respect to FIG. 7A. Inside, or mounted to temple 102, are ear phones 130, inertial sensors 132, GPS transceiver 144 and temperature sensor 138. In one embodiment inertial sensors 132 include a three axis magnetometer 132A, three axis gyro 132B and three axis accelerometer 132C (See FIG. 7A). The inertial sensors are for sensing position, orientation, and sudden accelerations of head mounted display device 2. From these movements, head position may also be determined.

The display device 2 provides an image generation unit which can create one or more images including one or more virtual objects. In some embodiments a microdisplay may be used as the image generation unit. A microdisplay assembly 173 in this example comprises light processing elements and a variable focus adjuster 135. An example of a light processing element is a microdisplay unit 120. Other examples include one or more optical elements such as one or more lenses of a lens system 122 and one or more reflecting elements such as surfaces 124*a* and 124*b* in FIGS. 6A and 6B or 124 in FIGS. 6C and 6D. Lens system 122 may comprise a single lens or a plurality of lenses.

Mounted to or inside temple 102, the microdisplay unit 120 includes an image source and generates an image of a virtual object. The microdisplay unit 120 is optically aligned with the lens system 122 and the reflecting surface 124 or reflecting surfaces 124*a* and 124*b* as illustrated in the following figures. The optical alignment may be along an optical axis 133 or an optical path 133 including one or more optical axes. The microdisplay unit 120 projects the image of the virtual object through lens system 122, which may direct the image light, onto reflecting element 124 which directs the light into lightguide optical element 112 as in FIGS. 6C and 6D or onto reflecting surface 124*a* (e.g. a mirror or other surface) which directs the light of the virtual image to a partially reflecting element 124*b* which combines the virtual image view along path 133 with the natural or actual direct view along the optical axis 142 as in FIGS. 6A-6D. The combination of views are directed into a user's eye.

The variable focus adjuster 135 changes the displacement between one or more light processing elements in the optical path of the microdisplay assembly or an optical power of an element in the microdisplay assembly. The optical power of a lens is defined as the reciprocal of its focal length, e.g. 1/focal length, so a change in one effects the other. The change in focal length results in a change in the region of the field of view, e.g. a region at a certain distance, which is in focus for an image generated by the microdisplay assembly 173.

In one example of the microdisplay assembly 173 making displacement changes, the displacement changes are guided within an armature 137 supporting at least one light processing element such as the lens system 122 and the microdisplay 120 in this example. The armature 137 helps stabilize the alignment along the optical path 133 during physical movement of the elements to achieve a selected displacement or optical power. In some examples, the adjuster 135 may move one or more optical elements such as a lens in lens system 122 within the armature 137. In other examples, the armature may have grooves or space in the area around a light processing element so it slides over the element, for example, microdisplay 120, without moving the light processing element. Another element in the armature such as the lens system 122 is attached so that the system 122 or a lens within slides or moves with the moving armature 137. The displacement range is typically on the order of a few millimeters (mm). In one example, the range is 1-2 mm. In other examples, the armature 137 may provide support to the lens system 122 for focal adjustment techniques involving adjustment of other physical parameters than displacement. An example of such a parameter is polarization.

For more information on adjusting a focal distance of a microdisplay assembly, see U.S. patent Ser. No. 12/941,825 entitled "Automatic Variable Virtual Focus for Augmented Reality Displays," filed Nov. 8, 2010, having inventors Avi Bar-Zeev and John Lewis and which is hereby incorporated by reference.

In one example, the adjuster 135 may be an actuator such as a piezoelectric motor. Other technologies for the actuator may also be used and some examples of such technologies are a voice coil formed of a coil and a permanent magnet, a magnetostriction element, and an electrostriction element.

There are different image generation technologies that can be used to implement microdisplay 120. For example, microdisplay 120 can be implemented using a transmissive projection technology where the light source is modulated by optically active material, backlit with white light. These technologies are usually implemented using LCD type displays with powerful backlights and high optical energy densities. Microdisplay 120 can also be implemented using a reflective technology for which external light is reflected and modulated by an optically active material. The illumination is forward lit by either a white source or RGB source, depending on the technology. Digital light processing (DLP), liquid crystal on silicon (LCOS) and Mirasol® display technology from Qualcomm, Inc. are all examples of reflective technologies which are efficient as most energy is reflected away from the modulated structure and may be used in the system described herein. Additionally, microdisplay 120 can be implemented using an emissive technology where light is generated by the display. For example, a PicoP™ engine from Microvision, Inc. emits a laser signal with a micro mirror steering either onto a tiny screen that acts as a transmissive element or beamed directly into the eye (e.g., laser).

As mentioned above, the configuration of the light processing elements of the microdisplay assembly 173 create a focal distance or focal region in which a virtual object appears in an image. Changing the configuration changes the focal region for the virtual object image. The focal region determined by the light processing elements can be determined and changed based on the equation $1/S1+1/S2=1/f$.

The symbol f represents the focal length of a lens such as lens system 122 in the microdisplay assembly 173. The lens system 122 has a front nodal point and a rear nodal point. If light rays are directed toward either nodal point at a given angle relative to the optical axis, the light rays will emerge from the other nodal point at an equivalent angle relative to the optical axis. In one example, the rear nodal point of lens system 122 would be between itself and the microdisplay 120. The distance from the rear nodal point to the microdisplay 120 may be denoted as S2. The front nodal point is typically within a few mm of lens system 122. The target location is the location of the virtual image to be generated by the microdisplay 120 in a three-dimensional physical space. The distance from the front nodal point to the target location of the virtual image may be denoted as S1. Since the image is to be a virtual image appearing on the same side of the lens as the microdisplay 120, sign conventions give that S1 has a negative value.

If the focal length of the lens is fixed, S1 and S2 are varied to focus virtual objects at different depths. For example, an initial position may have S1 set to infinity, and S2 equal to the focal length of lens system 122. Assuming lens system 122 has a focal length of 10 mm, consider an example in which the virtual object is to be placed about 1 foot or 300 mm into the user's field of view. S1 is now about −300 mm, f is 10 mm and S2 is set currently at the initial position of the focal length, 10 mm, meaning the rear nodal point of lens system 122 is 10 mm from the microdisplay 120. The new distance or new displacement between the lens 122 and microdisplay 120 is determined based on $1/(-300)+1/S2=1/10$ with all in units of mm. The result is about 9.67 mm for S2.

In one example, one or more processors such as in the control circuitry, the processing unit 4,5 or both can calculate the displacement values for S1 and S2, leaving the focal length f fixed and cause the control circuitry 136 to cause a variable adjuster driver 237 (see FIG. 7A) to send drive signals to have the variable virtual focus adjuster 135 move the lens system 122 along the optical path 133 for example. In other embodiments, the microdisplay unit 120 may be moved instead or in addition to moving the lens system 122. In other embodiments, the focal length of at least one lens in the lens system 122 may be changed instead or with changes in the displacement along the optical path 133 as well.

FIG. 5B is a side view of an eyeglass temple in another embodiment of a mixed reality display device providing support for hardware and software components and three dimensional adjustment of a microdisplay assembly. Some of the numerals illustrated in the FIG. 5A above have been removed to avoid clutter in the drawing. In embodiments where the display optical system 14 is moved in any of three dimensions, the optical elements represented by reflecting surface 124 and the other elements of the microdisplay assembly 173, e.g. 120, 122 may also be moved for maintaining the optical path 133 of the light of a virtual image to the display optical system. An XYZ transport mechanism in this example made up of one or more motors represented by motor block 203 and shafts 205 under control of the processor 210 of control circuitry 136 (see FIG. 7A) control movement of the elements of the microdisplay assembly 173. An example of motors which may be used are piezoelectric motors. In the illustrated example, one motor is attached to the armature 137 and moves the variable focus adjuster 135 as well, and another representative motor 203 controls the movement of the reflecting element 124.

FIG. 6A is a top view of an embodiment of a movable display optical system 14 of a see-through, near-eye, mixed reality device 2 including an arrangement of gaze detection elements. A portion of the frame 115 of the near-eye display device 2 will surround a display optical system 14 and provides support for elements of an embodiment of a microdisplay assembly 173 including microdisplay 120 and its accompanying elements as illustrated. In order to show the components of the display system 14, in this case 14r for the right eye system, a top portion of the frame 115 surrounding the display optical system is not depicted. Additionally, the microphone 110 in bridge 104 is not shown in this view to focus attention on the operation of the display adjustment mechanism 203. As in the example of FIG. 4C, the display optical system 14 in this embodiment is moved by moving an inner frame 117r, which in this example surrounds the microdisplay assembly 173 as well. The display adjustment mechanism is embodied in this embodiment as three axis motors 203 which attach their shafts 205 to inner frame 117r to translate the display optical system 14, which in this embodiment includes the microdisplay assembly 173, in any of three dimensions as denoted by symbol 144 indicating three (3) axes of movement.

The display optical system 14 in this embodiment has an optical axis 142 and includes a see-through lens 118 allowing the user an actual direct view of the real world. In this example, the see-through lens 118 is a standard lens used in eye glasses and can be made to any prescription (including no prescription). In another embodiment, see-through lens 118 can be replaced by a variable prescription lens. In some embodiments, see-through, near-eye display device 2 will include additional lenses.

The display optical system 14 further comprises reflecting surfaces 124a and 124b. In this embodiment, light from the microdisplay 120 is directed along optical path 133 via a reflecting element 124a to a partially reflective element 124b embedded in lens 118 which combines the virtual object image view traveling along optical path 133 with the natural or actual direct view along the optical axis 142 so that the combined views are directed into a user's eye, right one in this example, at the optical axis, the position with the most collimated light for a clearest view.

A detection area 139r of a light sensor is also part of the display optical system 14r. An optical element 125 embodies the detection area 139r by capturing reflected light from the user's eye received along the optical axis 142 and directs the captured light to the sensor 134r, in this example positioned in the lens 118 within the inner frame 117r. As shown, the arrangement allows the detection area 139 of the sensor 134r to have its center aligned with the center of the display optical system 14. For example, if sensor 134r is an image sensor, sensor 134r captures the detection area 139, so an image captured at the image sensor is centered on the optical axis because the detection area 139 is. In one example, sensor 134r is a visible light camera or a combination of RGB/IR camera, and the optical element 125 includes an optical element which reflects visible light reflected from the user's eye, for example a partially reflective mirror.

In other embodiments, the sensor 134r is an IR sensitive device such as an IR camera, and the element 125 includes a hot reflecting surface which lets visible light pass through it and reflects IR radiation to the sensor 134r. An IR camera may capture not only glints, but also an infra-red or near infra-red image of the user's eye including the pupil.

In other embodiments, the IR sensor device 134r is a position sensitive device (PSD), sometimes referred to as an optical position sensor. The position of detected light on the surface of the sensor is identified. A PSD can be selected which is sensitive to a wavelength range or about a predetermined wavelength of IR illuminators for the glints. When light within the wavelength range or about the predetermined wavelength of the position sensitive device is detected on the sensor or light sensitive portion of the device, an electrical signal is generated which identifies the location on the surface of the detector. In some embodiments, the surface of a PSD is divided into discrete sensors like pixels from which the location of the light can be determined. In other examples, a PSD isotropic sensor may be used in which a change in local resistance on the surface can be used to identify the location of the light spot on the PSD. Other embodiments of PSDs may also be used. By operating the illuminators 153 in a predetermined sequence, the location of the reflection of glints on the PSD can be identified and hence related back to their location on a cornea surface.

The depiction of the light directing elements, in this case reflecting elements, 125, 124, 124a and 124b in FIGS. 6A-6D are representative of their functions. The surfaces may take any number of forms and be implemented with one or more optical components in one or more arrangements for directing light to its intended destination such as a camera sensor or a user's eye. As shown, the arrangement allows the detection area 139 of the sensor to have its center aligned with the center of the display optical system 14. The image sensor 134r captures the detection area 139, so an image captured at the image sensor is centered on the optical axis because the detection area 139 is.

As discussed in FIGS. 2A and 2B above and in the figures below, when the user is looking straight ahead, and the center of the user's pupil is centered in an image captured of the user's eye when a detection area 139 or an image sensor 134r is effectively centered on the optical axis of the display, the display optical system 14r is aligned with the pupil. When both display optical systems 14 are aligned with their respective pupils, the distance between the optical centers matches or is aligned with the user's inter-pupillary distance. In the example of FIG. 6A, the inter-pupillary distance can be aligned with the display optical systems 14 in three dimensions.

In one embodiment, if the data captured by the sensor 134 indicates the pupil is not aligned with the optical axis, one or more processors in the processing unit 4,5 or the control circuitry 136 or both use a mapping criteria which correlates a distance or length measurement unit to a pixel or other discrete unit or area of the image for determining how far off the center of the pupil is from the optical axis 142. Based on the distance determined, the one or more processors determine adjustments of how much distance and in which direction the display optical system 14r is to be moved to align the optical axis 142 with the pupil. Control signals are applied by one or more display adjustment mechanism drivers 245 to each of the components, e.g. motors 203, making up one or more display adjustment mechanisms 203. In the case of motors in this example, the motors move their shafts 205 to move the inner frame 117r in at least one direction indicated by the control signals. On the temple side of the inner frame 117r are flexible sections 215a, 215b of the frame 115 which are attached to the inner frame 117r at one end and slide within grooves 217a and 217b within the interior of the temple frame 115 to anchor the inner frame 117 to the frame 115 as the display optical system 14 is move in any of three directions for width, height or depth changes with respect to the respective pupil.

In addition to the sensor, the display optical system 14 includes other gaze detection elements. In this embodiment, attached to frame 117r on the sides of lens 118, are at least two (2) but may be more, infra-red (IR) illuminating devices 153 which direct narrow infra-red light beams within a particular wavelength range or about a predetermined wavelength at the user's eye to each generate a respective glint on a surface of the respective cornea. In other embodiments, the illuminators and any photodiodes may be on the lenses, for example at the corners or edges. In this embodiment, in addition to the at least 2 infra-red (IR) illuminating devices 153 are IR photodetectors 152. Each photodetector 152 is sensitive to IR radiation within the particular wavelength range of its corresponding IR illuminator 153 across the lens 118 and is positioned to detect a respective glint. As shown in FIGS. 4A-4C, the illuminator and photodetector are separated by a barrier 154 so that incident IR light from the illuminator 153 does not interfere with reflected IR light being received at the photodetector 152. In the case where the sensor 134 is an IR sensor, the photodetectors 152 may not be needed or may be an additional glint data capture source. With a visible light camera, the photodetectors 152 capture light from glints and generate glint intensity values.

In FIGS. 6A-6D, the positions of the gaze detection elements, e.g. the detection area 139 and the illuminators 153 and photodetectors 152 are fixed with respect to the optical axis of the display optical system 14. These elements may move with the display optical system 14r, and hence its optical axis, on the inner frame, but their spatial relationship to the optical axis 142 does not change.

FIG. 6B is a top view of another embodiment of a movable display optical system of a see-through, near-eye, mixed reality device including an arrangement of gaze detection elements. In this embodiment, light sensor 134r may be embodied as a visible light camera, sometimes referred to as an RGB camera, or it may be embodied as an IR camera or a camera capable of processing light in both the visible and IR ranges, e.g. a depth camera. In this example, the image sensor 134r is the detection area 139r. The image sensor 134 of the camera is located vertically on the optical axis 142 of the display optical system. In some examples, the camera may be located on frame 115 either above or below see-through lens 118 or embedded in the lens 118. In some embodiments, the illuminators 153 provide light for the camera, and in other embodiments the camera captures images with ambient lighting or light from its own light source. Image data captured may be used to determine alignment of the pupil with the optical axis. Gaze determination techniques based on image data, glint data or both may be used based on the geometry of the gaze detection elements.

In this example, the motor 203 in bridge 104 moves the display optical system 14r in a horizontal direction with respect to the user's eye as indicated by directional symbol 145. The flexible frame portions 215a and 215b slide within grooves 217a and 217b as the system 14 is moved. In this example, reflecting element 124a of an microdisplay assembly 173 embodiment is stationery. As the IPD is typically determined once and stored, any adjustment of the focal length between the microdisplay 120 and the reflecting element 124a that may be done may be accomplished by the microdisplay assembly, for example via adjustment of the microdisplay elements within the armature 137.

FIG. 6C is a top view of a third embodiment of a movable display optical system of a see-through, near-eye, mixed reality device including an arrangement of gaze detection elements. The display optical system 14 has a similar arrangement of gaze detection elements including IR illuminators 153 and photodetectors 152, and a light sensor 134r located on the frame 115 or lens 118 below or above optical axis 142. In this example, the display optical system 14 includes a light guide optical element 112 as the reflective element for directing the images into the user's eye and is situated between an additional see-through lens 116 and see-through lens 118. As reflecting element 124 is within the lightguide optical element and moves with the element 112, an embodiment of a microdisplay assembly 173 is attached on the temple 102 in this example to a display adjustment mechanism 203 for the display optical system 14 embodied as a set of three axis motor 203 with shafts 205 include at least one for moving the microdisplay assembly. One or more motors 203 on the bridge 104 are representative of the other components of the display adjustment mechanism 203 which provides three axes of movement 145. In another embodiment, the motors may operate to only move the devices via their attached shafts 205 in the horizontal direction. The motor 203 for the microdisplay assembly 173 would also move it horizontally for maintaining alignment between the light coming out of the microdisplay 120 and the reflecting element 124. A processor 210 of the control circuitry (see FIG. 7A) coordinates their movement.

Lightguide optical element 112 transmits light from microdisplay 120 to the eye of the user wearing head mounted display device 2. Lightguide optical element 112 also allows light from in front of the head mounted display device 2 to be transmitted through lightguide optical element 112 to the user's eye thereby allowing the user to have an actual direct view of the space in front of head mounted display device 2 in addition to receiving a virtual image from microdisplay 120. Thus, the walls of lightguide optical element 112 are see-through. Lightguide optical element 112 includes a first reflecting surface 124 (e.g., a mirror or other surface). Light from microdisplay 120 passes through lens 122 and becomes incident on reflecting surface 124. The reflecting surface 124 reflects the incident light from the microdisplay 120 such that light is trapped inside a planar, substrate comprising lightguide optical element 112 by internal reflection.

After several reflections off the surfaces of the substrate, the trapped light waves reach an array of selectively reflecting surfaces 126. Note that only one of the five surfaces is labeled 126 to prevent over-crowding of the drawing. Reflecting surfaces 126 couple the light waves incident upon those reflecting surfaces out of the substrate into the eye of the user. More details of a lightguide optical element can be found in United States Patent Application Publication 2008/0285140, Ser. No. 12/214,366, published on Nov. 20, 2008, "Substrate-Guided Optical Devices" incorporated herein by reference in its entirety. In one embodiment, each eye will have its own lightguide optical element 112.

FIG. 6D is a top view of a fourth embodiment of a movable display optical system of a see-through, near-eye, mixed reality device including an arrangement of gaze detection elements. This embodiment is similar to FIG. 6C's embodiment including a light guide optical element 112. However, the only light detectors are the IR photodetectors 152, so this embodiment relies on glint detection only for gaze detection as discussed in the examples below.

In the embodiments of FIGS. 6A-6D, the positions of the gaze detection elements, e.g. the detection area 139 and the illuminators 153 and photodetectors 152 are fixed with respect to each other. In these examples, they are also fixed in relation to the optical axis of the display optical system 14.

In the embodiments above, the specific number of lenses shown are just examples. Other numbers and configurations of lenses operating on the same principles may be used. Additionally, in the examples above, only the right side of the see-through, near-eye display 2 are shown. A full near-eye, mixed reality display device would include as examples another set of lenses 116 and/or 118, another lightguide optical element 112 for the embodiments of FIGS. 6C and 6D, another micro display 120, another lens system 122, likely another environment facing camera 113, another eye tracking camera 134 for the embodiments of FIGS. 6A to 6C, earphones 130, and a temperature sensor 138.

Figure 7A:
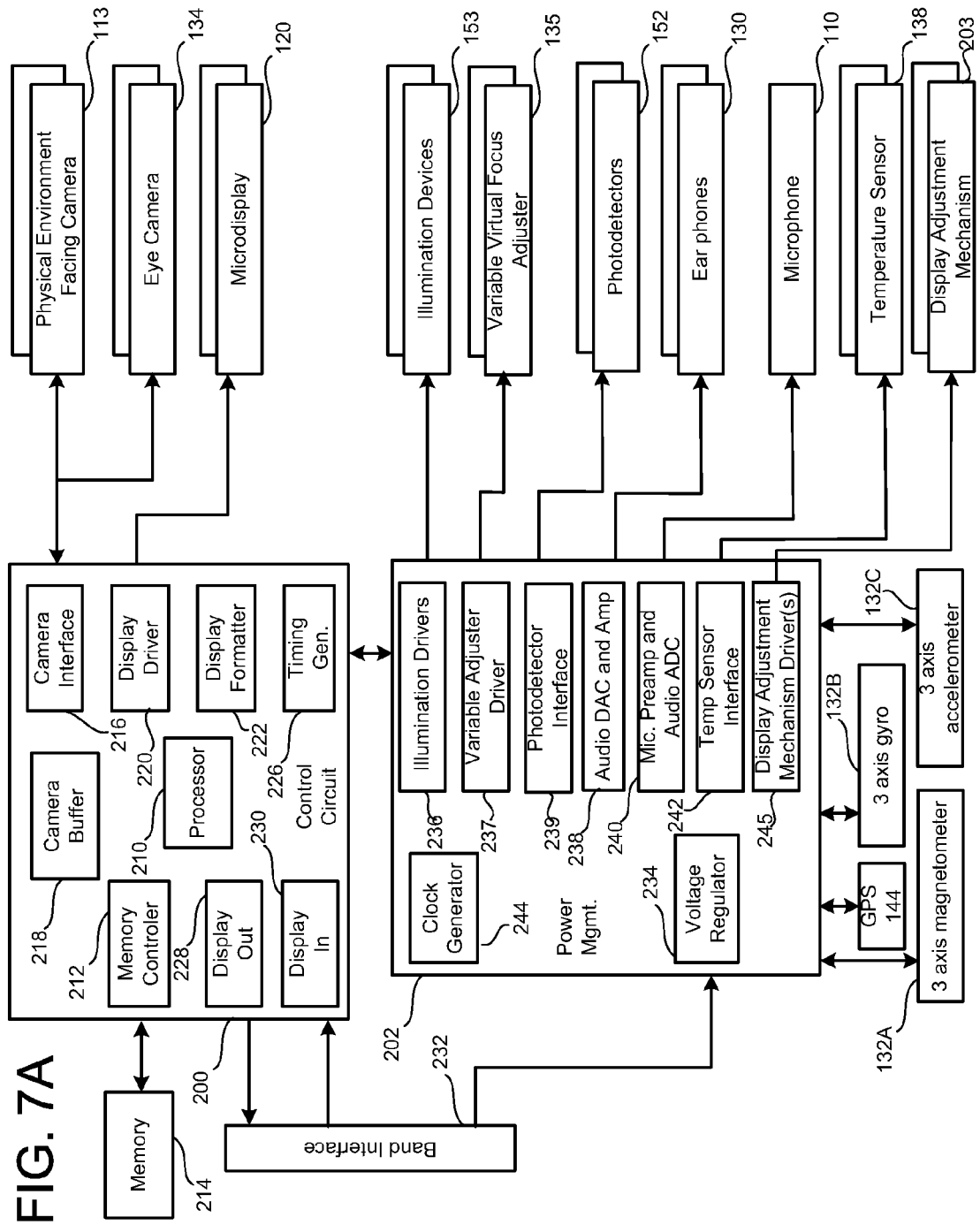
FIG. 7A is a block diagram of one embodiment of hardware and software components of a see-through, near-eye, mixed reality display unit as may be used with one or more embodiments.

FIG. 7A is a block diagram of one embodiment of hardware and software components of a see-through, near-eye, mixed reality display unit 2 as may be used with one or more embodiments. FIG. 7B is a block diagram describing the various components of a processing unit 4,5. In this embodiment, near-eye display device 2, receives instructions about a virtual image from processing unit 4,5 and provides the sensor information back to processing unit 4,5. Software and hardware components which may be embodied in a processing unit 4,5 are depicted in FIG. 7B, will receive the sensory information from the display device 2 and may also receive sensory information from hub computing device 12 (See FIG. 1A). Based on that information, processing unit 4, 5 will determine where and when to provide a virtual image to the user and send instructions accordingly to the control circuitry 136 of the display device 2.

Note that some of the components of FIG. 7A (e.g., physical environment facing camera 113, eye camera 134, variable virtual focus adjuster 135, photodetector interface 139, micro display 120, illumination device 153 or illuminators, earphones 130, temperature sensor 138, display adjustment mechanism 203) are shown in shadow to indicate that there are at least two of each of those devices, at least one for the left side and at least one for the right side of head mounted display device 2. FIG. 7A shows the control circuit 200 in communication with the power management circuit 202. Control circuit 200 includes processor 210, memory controller 212 in communication with memory 214 (e.g., D-RAM), camera interface 216, camera buffer 218, display driver 220, display formatter 222, timing generator 226, display out interface 228, and display in interface 230. In one embodiment, all of components of control circuit 220 are in communication with each other via dedicated lines of one or more buses. In another embodiment, each of the components of control circuit 200 are in communication with processor 210.

Camera interface 216 provides an interface to the two physical environment facing cameras 113 and each eye camera 134 and stores respective images received from the cameras 113, 134 in camera buffer 218. Display driver 220 will drive microdisplay 120. Display formatter 222 may provide information, about the virtual image being displayed on microdisplay 120 to one or more processors of one or more computer systems, e.g. 4, 5, 12, 210 performing processing for the augmented reality system. Timing generator 226 is used to provide timing data for the system. Display out 228 is a buffer for providing images from physical environment facing cameras 113 and the eye cameras 134 to the processing unit 4, 5. Display in 230 is a buffer for receiving images such as a virtual image to be displayed on microdisplay 120. Display out 228 and display in 230 communicate with band interface 232 which is an interface to processing unit 4, 5.

Power management circuit 202 includes voltage regulator 234, eye tracking illumination driver 236, variable adjuster driver 237, photodetector interface 239, audio DAC and amplifier 238, microphone preamplifier and audio ADC 240, temperature sensor interface 242, display adjustment mechanism driver(s) 245 and clock generator 244. Voltage regulator 234 receives power from processing unit 4,5 via band interface 232 and provides that power to the other components of head mounted display device 2. Illumination driver 236 controls, for example via a drive current or voltage, the illumination devices 153 to operate about a predetermined wavelength or within a wavelength range. Audio DAC and amplifier 238 receives the audio information from earphones 130. Microphone preamplifier and audio ADC 240 provides an interface for microphone 110. Temperature sensor interface 242 is an interface for temperature sensor 138. One or more display adjustment drivers 245 provide control signals to one or more motors or other devices making up each display adjustment mechanism 203 which represent adjustment amounts of movement in at least one of three directions. Power management unit 202 also provides power and receives data back from three axis magnetometer 132A, three axis gyro 132B and three axis accelerometer 132C. Power management unit 202 also provides power and receives data back from and sends data to GPS transceiver 144.

The variable adjuster driver 237 provides a control signal, for example a drive current or a drive voltage, to the adjuster 135 to move one or more elements of the microdisplay assembly 173 to achieve a displacement for a focal region calculated by software executing in a processor 210 of the control circuitry 13, or the processing unit 4,5 or the hub computer 12 or both. In embodiments of sweeping through a range of displacements and, hence, a range of focal regions, the variable adjuster driver 237 receives timing signals from the timing generator 226, or alternatively, the clock generator 244 to operate at a programmed rate or frequency.

The photodetector interface 239 receives performs any analog to digital conversion needed for voltage or current readings from each photodetector, stores the readings in a processor readable format in memory via the memory controller 212, and monitors the operation parameters of the photodetectors 152 such as temperature and wavelength accuracy.

FIG. 7B is a block diagram of one embodiment of the hardware and software components of a processing unit 4 associated with a see-through, near-eye, mixed reality display unit. The mobile device 5 may include this embodiment of hardware and software components as well as similar components which perform similar functions. FIG. 7B shows controls circuit 304 in communication with power management circuit 306. Control circuit 304 includes a central processing unit (CPU) 320, graphics processing unit (GPU) 322, cache 324, RAM 326, memory control 328 in communication with memory 330 (e.g., D-RAM), flash memory controller 332 in communication with flash memory 334 (or other type of non-volatile storage), display out buffer 336 in communication with see-through, near-eye display device 2 via band interface 302 and band interface 232, display in buffer 338 in communication with near-eye display device 2 via band interface 302 and band interface 232, microphone interface 340 in communication with an external microphone connector 342 for connecting to a microphone, PCI express interface for connecting to a wireless communication device 346, and USB port(s) 348.

In one embodiment, wireless communication component 346 can include a Wi-Fi enabled communication device, Bluetooth communication device, infrared communication device, etc. The USB port can be used to dock the processing unit 4, 5 to hub computing device 12 in order to load data or software onto processing unit 4, 5, as well as charge processing unit 4, 5. In one embodiment, CPU 320 and GPU 322 are the main workhorses for determining where, when and how to insert virtual images into the view of the user.

Power management circuit 306 includes clock generator 360, analog to digital converter 362, battery charger 364, voltage regulator 366, see-through, near-eye display power source 376, and temperature sensor interface 372 in communication with temperature sensor 374 (located on the wrist band of processing unit 4). An alternating current to direct current converter 362 is connected to a charging jack 370 for receiving an AC supply and creating a DC supply for the system. Voltage regulator 366 is in communication with battery 368 for supplying power to the system. Battery charger 364 is used to charge battery 368 (via voltage regulator 366) upon receiving power from charging jack 370. Device power interface 376 provides power to the display device 2.

The figures above provide examples of geometries of elements for a display optical system which provide a basis for different methods of aligning an IPD as discussed in the following figures. The method embodiments may refer to elements of the systems and structures above for illustrative context; however, the method embodiments may operate in system or structural embodiments other than those described above.

The method embodiments below identify or provide one or more objects of focus for aligning an IPD. FIGS. 8A and 8B discuss some embodiments for determining positions of objects within a field of view of a user wearing the display device.

FIG. 8A is a block diagram of a system embodiment for determining positions of objects within a user field of view of a see-through, near-eye, mixed reality display device. This embodiment illustrates how the various devices may leverage networked computers to map a three-dimensional model of a user field of view and the real and virtual objects within the model. An application 456 executing in a processing unit 4,5 communicatively coupled to a display device 2 can communicate over one or more communication networks 50 with a computing system 12 for processing of image data to determine and track a user field of view in three dimensions. The computing system 12 may be executing an application 452 remotely for the processing unit 4,5 for providing images of one or more virtual objects. As mentioned above, in some embodiments, the software and hardware components of the processing unit are integrated into the display device 2. Either or both of the applications 456 and 452 working together may map a 3D model of space around the user. A depth image processing application 450 detects objects, identifies objects and their locations in the model. The application 450 may perform its processing based on depth image data from depth camera like 20A and 20B, two-dimensional or depth image data from one or more front facing cameras 113, and GPS metadata associated with objects in the image data obtained from a GPS image tracking application 454.

The GPS image tracking application 454 identifies images of the user's location in one or more image database(s) 470 based on GPS data received from the processing unit 4,5 or other GPS units identified as being within a vicinity of the user, or both. Additionally, the image database(s) may provide accessible images of a location with metadata like GPS data and identifying data uploaded by users who wish to share their images. The GPS image tracking application provides distances between objects in an image based on GPS data to the depth image processing application 450. Additionally, the application 456 may perform processing for mapping and locating objects in a 3D user space locally and may interact with the GPS image tracking application 454 for receiving distances between objects. Many combinations of shared processing are possible between the applications by leveraging network connectivity.

FIG. 8B is a flowchart of a method embodiment for determining a three-dimensional user field of view of a see-through, near-eye, mixed reality display device. In step 510, one or more processors of the control circuitry 136, the processing unit 4,5, the hub computing system 12 or a combination of these receive image data from one or more front facing cameras 113, and in step 512 identify one or more real objects in front facing image data. Based on the position of the front facing camera 113 or a front facing camera 113 for each display optical system, the image data from the front facing camera approximates the user field of view. The data from two cameras 113 may be aligned and offsets for the positions of the front facing cameras 113 with respect to the display optical axes accounted for. Data from the orientation sensor 132, e.g. the three axis accelerometer 132C and the three axis magnetometer 132A, can also be used with the front facing camera 113 image data for mapping what is around the user, the position of the user's face and head in order to determine which objects, real or virtual, he or she is likely focusing on at the time. Optionally, based on an executing application, the one or more processors in step 514 identify virtual object positions in a user field of view which may be determined to be the field of view captured in the front facing image data. In step 516, a three-dimensional position is determined for each object in the user field of view. In other words, where each object is located with respect to the display device 2, for example with respect to the optical axis 142 of each display optical system 14.

In some examples for identifying one or more real objects in the front facing image data, GPS data via a GPS unit, e.g. GPS unit 965 in the mobile device 5 or GPS transceiver 144 on the display device 2 may identify the location of the user. This location may be communicated over a network from the device 2 or via the processing unit 4,5 to a computer system 12 having access to a database of images 470 which may be accessed based on the GPS data. Based on pattern recognition of objects in the front facing image data and images of the location, the one or more processors determines a relative position of one or more objects in the front facing image data to one or more GPS tracked objects in the location. A position of the user from the one or more real objects is determined based on the one or more relative positions.

In other examples, each front facing camera is a depth camera providing depth image data or has a depth sensor for providing depth data which can be combined with image data to provide depth image data. The one or more processors of the control circuitry, e.g. 210, and the processing unit 4,5 identify one or more real objects including their three-dimensional positions in a user field of view based on the depth image data from the front facing cameras. Additionally, orientation sensor 132 data may also be used to refine which image data currently represents the user field of view. Additionally, a remote computer system 12 may also provide additional processing power to the other processors for identifying the objects and mapping the user field of view based on depth image data from the front facing image data.

In other examples, a user wearing the display device may be in an environment in which a computer system with depth cameras, like the example of the hub computing system 12 with depth cameras 20A and 20B in system 10 in FIG. 1A, maps in three-dimensions the environment or space and tracks real and virtual objects in the space based on the depth image data from its cameras and an executing application. For example, when a user enters a store, a store computer system may map the three-dimensional space. Depth images from multiple perspectives, include depth images from one or more display devices in some examples, may be combined by a depth image processing application 450 based on a common coordinate system for the space. Objects are detected, e.g. edge detection, in the space, and identified by pattern recognition techniques including facial recognition techniques with reference images of things and people from image databases. Such a system can send data such as the position of the user within the space and positions of objects around the user which the one or more processors of the device 2 and the processing unit 4,5 may use in detecting and identifying which objects are in the user field of view. Furthermore, the one or more processors of the display device 2 or the processing unit 4,5 may send the front facing image data and orientation data to the computer system 12 which performs object detection, identification and object position tracking within the user field of view and sends updates to the processing unit 4,5.

Figure 9A:
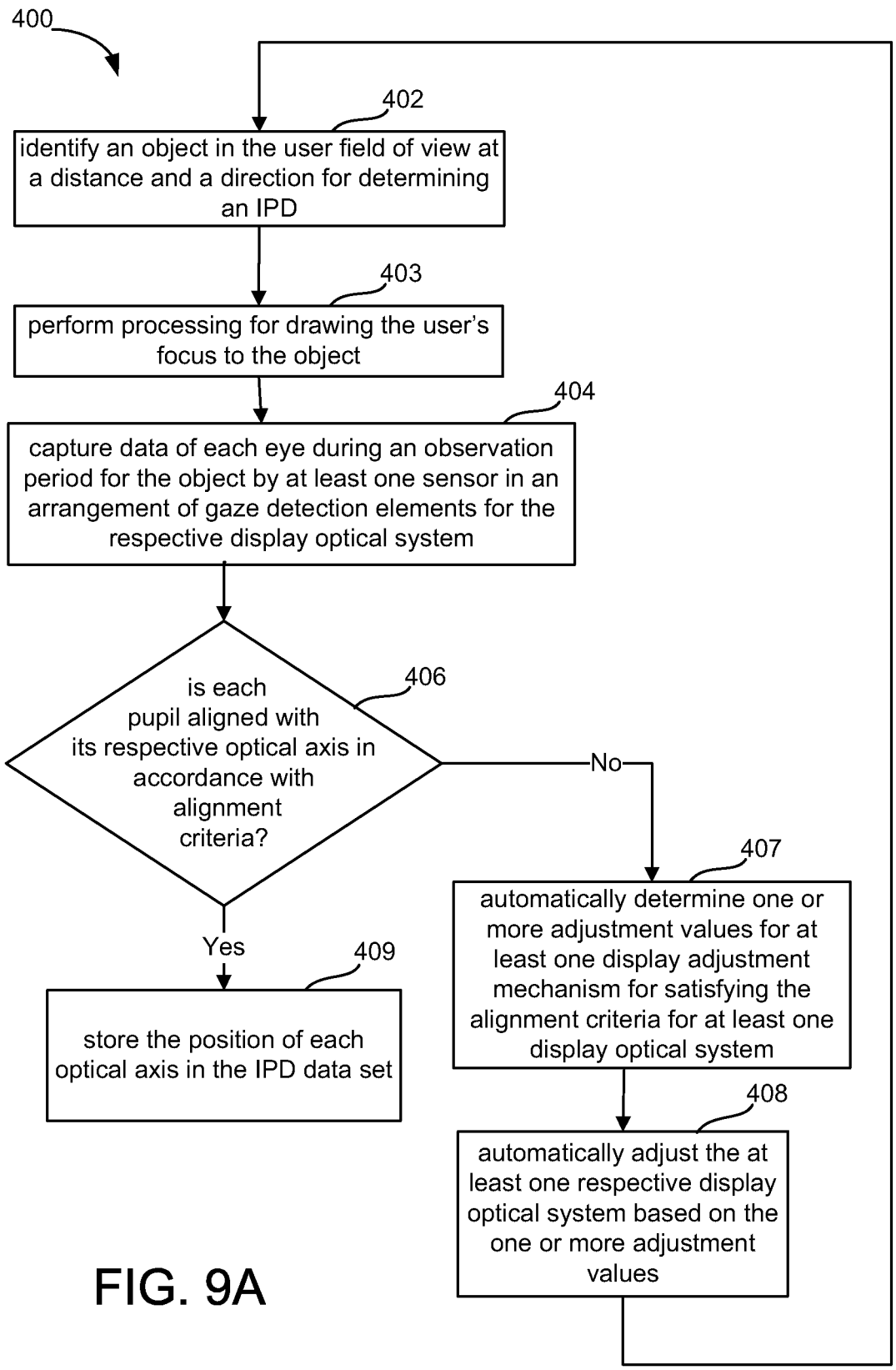
FIG. 9A is a flowchart of a method embodiment for automatically aligning a see-through, near-eye, mixed reality display with an IPD.

FIG. 9A is a flowchart of a method embodiment 400 for automatically aligning a see-through, near-eye, mixed reality display with an IPD. Steps 402 to 406 illustrate more details of an example of step 301 for automatically determining whether a see-through, near-eye, mixed reality display device is aligned with an IPD of a user in accordance with an alignment criteria. Steps 407 to 408 illustrate more detailed steps of an example for automatically adjusting the display device for bringing the device into alignment with the user IPD as in step 302.

In step 402, the one or more processors of the see-through, near-eye, mixed reality system such as processor 210 of the control circuitry, that in processing unit 4, the mobile device 5, or the hub computing system 12, alone or in combination, identify an object in the user field of view at a distance and a direction for determining an IPD. For the far IPD, the distance is at effective infinity, e.g. more than 5 feet, the direction is straight ahead with respect to the optical axis of each display optical system. In other words, the distance and direction are such that when each pupil is aligned with each optical axis, the user is looking straight ahead. In step 403, the one or more processors perform processing for drawing the user's focus to the object. In one example, the one or more processors electronically provide instructions requesting the user to look at the identified real object. In some instances, the user may be asked simply to look straight ahead. Some examples of electronically provided instructions are instructions displayed by the image generation unit 120, the mobile device 5 or on a display 16 by the hub computing system 12 or audio instructions through speakers 130 of the display device 2. In other examples, the object may have image enhancements applied to it for attracting the user's eyes to focus on it. For example, eye catching visual effects may be applied to the object during an observation period. Some examples of such visual effects are highlighting, blinking, and movement.

In step 404, the at least one sensor such as sensor 134r or the photodetectors 152 or both in an arrangement of gaze detection elements for the respective display optical system capture data for each eye during an observation period for the object. In one example, the captured data may be IR image data and glints reflecting from each eye captured by an IR camera. The glints are generated by IR illuminators 153. In other examples, the at least one sensor is an IR sensor like a position sensitive detector. The at least one sensor may also be the IR photodetectors 152. In some examples, the at least one sensor 134 may be a visible light camera. However, as previously mentioned, if an image of a virtual object is used in a process for determining IPD alignment, the reflections of the virtual object in the user's eye may be accounted for, for example, by filtering them out. If visible light illuminators generate glints, the user's eyes may react to the visible light of the illuminators.

In step 406, the one or more processors determine based on the captured data and the arrangement of the gaze detection elements whether each pupil is aligned with the optical axis of its respective display optical system in accordance with an alignment criteria. An alignment criteria may be a distance from the optical axis, e.g. 2 millimeters (mm). If so, the display device 2 has been aligned with each pupil and hence the IPD, and the one or more processors in step 409 store the position of each optical axis in the IPD data set.

If the alignment criteria is not satisfied, then in step 407, the one or more processors automatically determine one or more adjustment values for at least one display adjustment mechanism for satisfying the alignment criteria for at least one display optical system. By "automatically determines" means the one or more processors determine the values without a user identifying the adjustment values through mechanical manipulation. In many embodiments, based on stored device configuration data, the current position of the optical axis with respect to a fixed point of the support structure is tracked. In step 408, the processor causes the at least one display adjustment mechanism 203 via the one or more display adjustment mechanism drivers 245 to automatically adjust the at least one respective display optical system based on the one or more adjustment values. The steps of the method embodiment may be repeated a predetermined number of times or until the alignment criteria is satisfied.

Figure 9B:
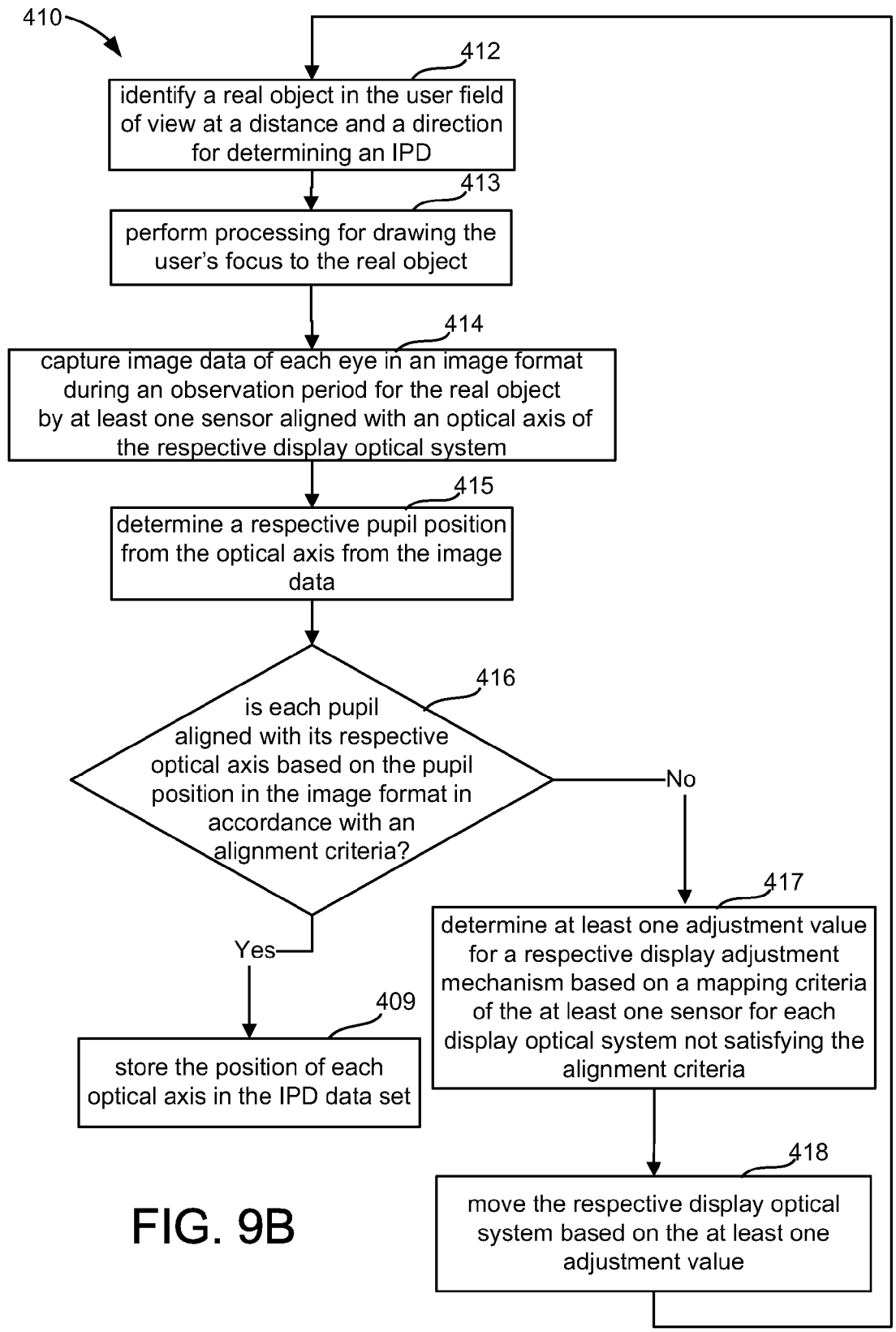
FIG. 9B is a flowchart of a method embodiment for automatically aligning a see-through, near-eye, mixed reality display with an IPD based on image data of a pupil in an image format.

FIG. 9B is a flowchart of a method embodiment 410 for an implementation example of automatically aligning a see-through, near-eye, mixed reality display device with an IPD of a user based on image data of a pupil for each eye in an image format. An image format has a predetermined size and shape, for example as may be set by an image sensor size and shape. An example of an image format is an image frame. The format is to provide a coordinate system, e.g. a center as an origin, for tracking a position within the image data. When the detection area 139 of an image sensor, e.g. an IR camera, or visible light camera if desired, is centered on the optical axis 142 of a display optical system 14, the image data in the image format is centered on the optical axis 142. How far off a pupil center is from the image center is a basis for determining whether the pupil is satisfactorily aligned with the optical axis. As in the examples of FIG. 4C, the image sensor 134 may be on the movable support 117 so as to be aligned along an axis passing though the optical axis 142. In processing the image data, the one or more processors factor in the offset vector of the image sensor 134 from the optical axis for determining whether the pupil is aligned with the optical axis.

Figures 17, 18, 19:
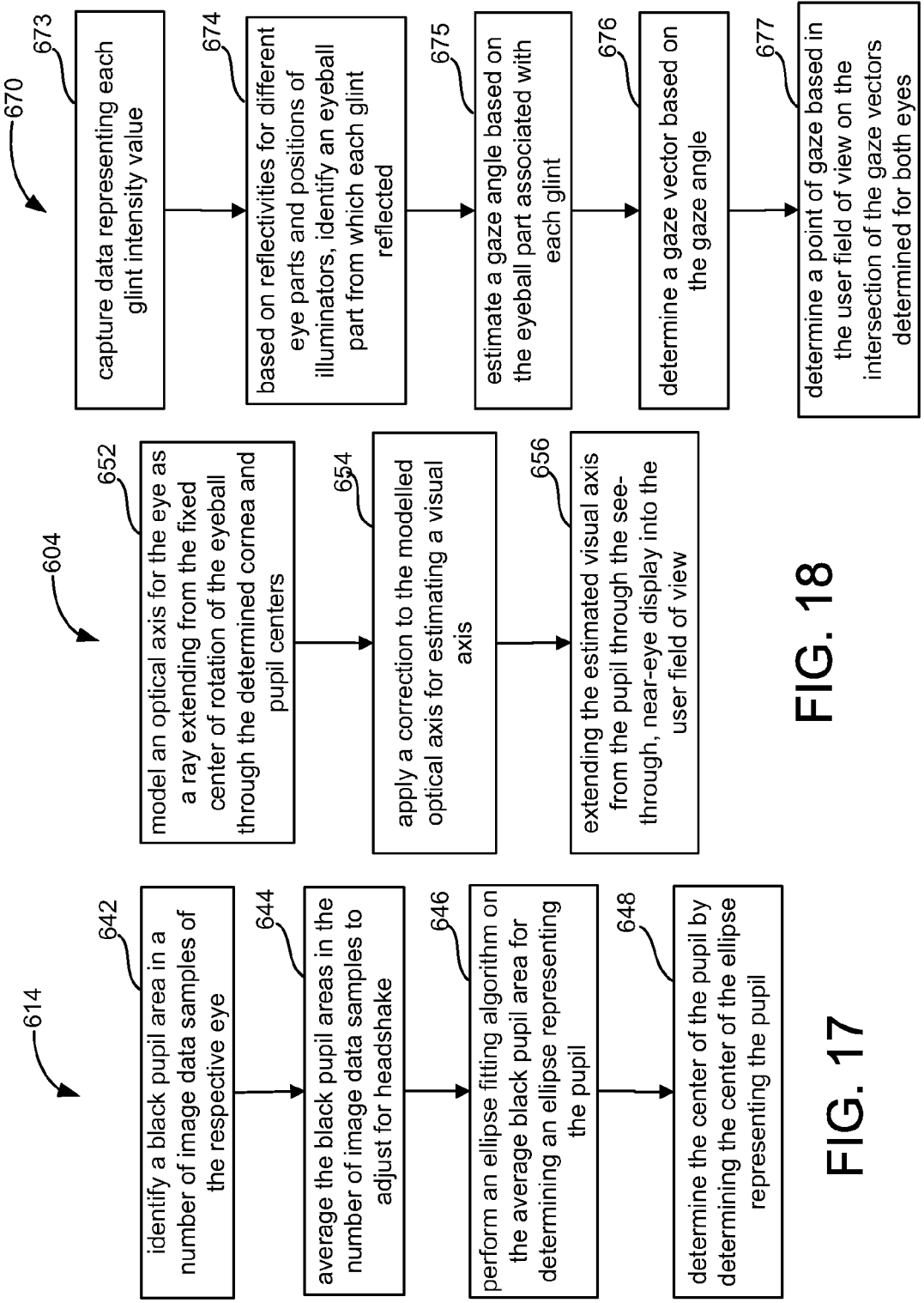
FIG. 17 is a flowchart illustrating a method embodiment for determining a pupil center from image data generated by a sensor.
FIG. 18 is a flowchart illustrating a method embodiment for determining a gaze vector based on the determined centers for the pupil, the cornea and a center of rotation of an eyeball.
FIG. 19 is a flowchart illustrating a method embodiment for determining gaze based on glint data.

In step 412, a real object is identified in the user field of view at a distance and a direction for determining an IPD, and in step 413, the one or more processors perform processing for drawing the user's focus to the real object. In step 414, image data of each eye is captured in an image format during an observation period for the real object by at least one sensor aligned with an optical axis of the respective display optical system. A respective pupil position with respect to the respective optical axis is determined from the image data in step 415. A pupil area in the image data may be identified by thresholding intensity values. An ellipse fitting algorithm may be applied for approximating the size and shape of the pupil, and a center of a resulting ellipse may be selected as the center of the pupil. Ideally, the center of the pupil is aligned with the optical axis of the display optical system. FIG. 17 discussed below provides an embodiment of a method for determining a pupil center from image data which may be used for implementing step 415 as well. In step 416, the one or more processors determine whether each pupil is aligned with the respective optical axis based on the pupil position in the image format, e.g. image frame, in accordance with an alignment criteria. In the case in which the detection area 139 is centered on the optical axis 142, the one or more processors determine whether the pupil position is centered in the image format, e.g. centered in the image frame, in accordance with an alignment criteria. The pupil position may be determined in horizontal and vertical directions for each eye with respect to the optical axis.

If the alignment criteria is satisfied, the one or more processors in step 409 store the position of each optical axis in the IPD data set. If not, in step 417, the one or more processors determine at least one adjustment value for a respective display adjustment mechanism based on a mapping criteria of the at least one sensor for each display optical system not satisfying the alignment criteria. In step 418, the one or more processors control the respective display adjustment mechanism to move the respective display optical system based on the at least one adjustment value. The steps of the method embodiment may be repeated a predetermined number of times or until the alignment criteria is satisfied.

Again, as illustrated in some of the figures above, the detection area of the camera may not be centered on the optical axis, e.g. 142 although aligned with it. For example, in FIGS. 4C, 6B and 6C, the camera image sensor 134 is in vertical alignment with the optical axis 142 as it is located above or below the optical axis 142, e.g. on frame 115.

Figure 9C:
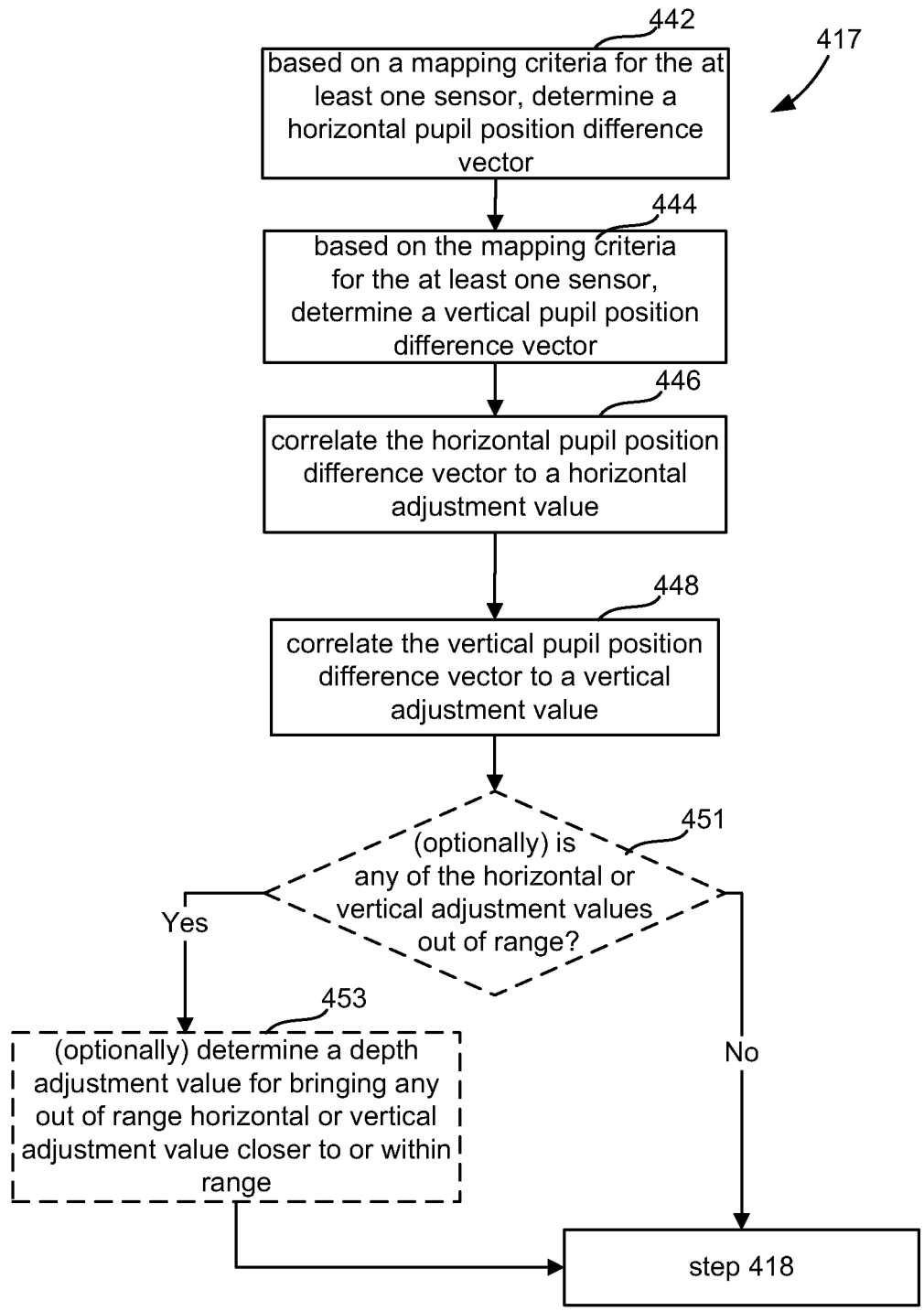
FIG. 9C is a flowchart of a method embodiment for determining at least one adjustment value for a display adjustment mechanism based on a mapping criteria of at least one sensor for each display optical system not satisfying an alignment criteria.

FIG. 9C is a flowchart of a method embodiment which may be used for implementing step 417 for determining at least one adjustment value for a display adjustment mechanism based on a mapping criteria of at least one sensor for a display optical system not satisfying an alignment criteria. In step 442, based on a mapping criteria for the at least one sensor, the one or more processors determine a horizontal pupil position difference vector. A pixel to distance mapping criteria may be used for each direction for which adjustment is provided. The mapping criteria may be different for vertical than for horizontal depending on the shape of the detection area of the image sensor. In step 444, based on the mapping criteria for the at least one sensor, a vertical pupil position difference vector is determined as well. In step 446, the one or more processors correlate the horizontal pupil position difference vector to a horizontal adjustment value, and in step 448, correlate the vertical pupil position difference vector to a vertical adjustment value.

As the horizontal IPD may have a range between 25 to 30 mm, a display adjustment mechanism typically has a range limit of distance to move a display optical system in any direction. A depth adjustment may assist with bringing an out of range adjustment value in the horizontal or vertical direction to being within range. Optional steps 451 and 453 may be performed. The one or more processors determine in optional step 451 whether any of the horizontal or vertical adjustment values are out of range. If not, alignment of the display optical system can be accomplished by movement in a two dimensional plane, and step 418 may be performed. If at least one adjustment value is out of range, the one or more processors determine in optional step 453 a depth adjustment value for bringing any out of range horizontal or vertical adjustment value closer to or within the range limit, and step 418 may be performed to adjust the display optical system.

As an illustrative example, if the optical axis is 12 mm to the right and the display adjustment mechanism can only move the display optical system 6 mm to the left, by increasing the depth between the display optical system and the pupil, the angle from the pupil when looking straight ahead to the position of the optical axis decreases, so a depth increase in combination with the 6 mm adjustment to the left brings the optical axis closer to aligning with the pupil in accordance with an alignment criteria. The effect of the depth change on the vertical dimension may also be taken into account so a vertical adjustment may also be necessary or the depth adjustment value modified.

The embodiments of FIGS. 9B and 9C may also be applied for glint data from each eye when the glints have a geometrical relationship to one another, and the sensor has a surface of discrete sensors such as pixels. For example, the glints for an eye generated by the illuminators form a box or other geometric shape aligned with the optical axis of the respective display optical system for the eye by the positions of the illuminators. If the sensor is a position sensitive detector (PSD) for detecting glints, a position on the sensor and the intensity value detected for a glint generated from a fixed illuminator are used to map a position of the pupil. Image data from an IR camera, or even a visible camera, provides greater accuracy for pupil position determination, but the glint data approach processes less data and is therefore computationally less intensive.

Figure 9D:
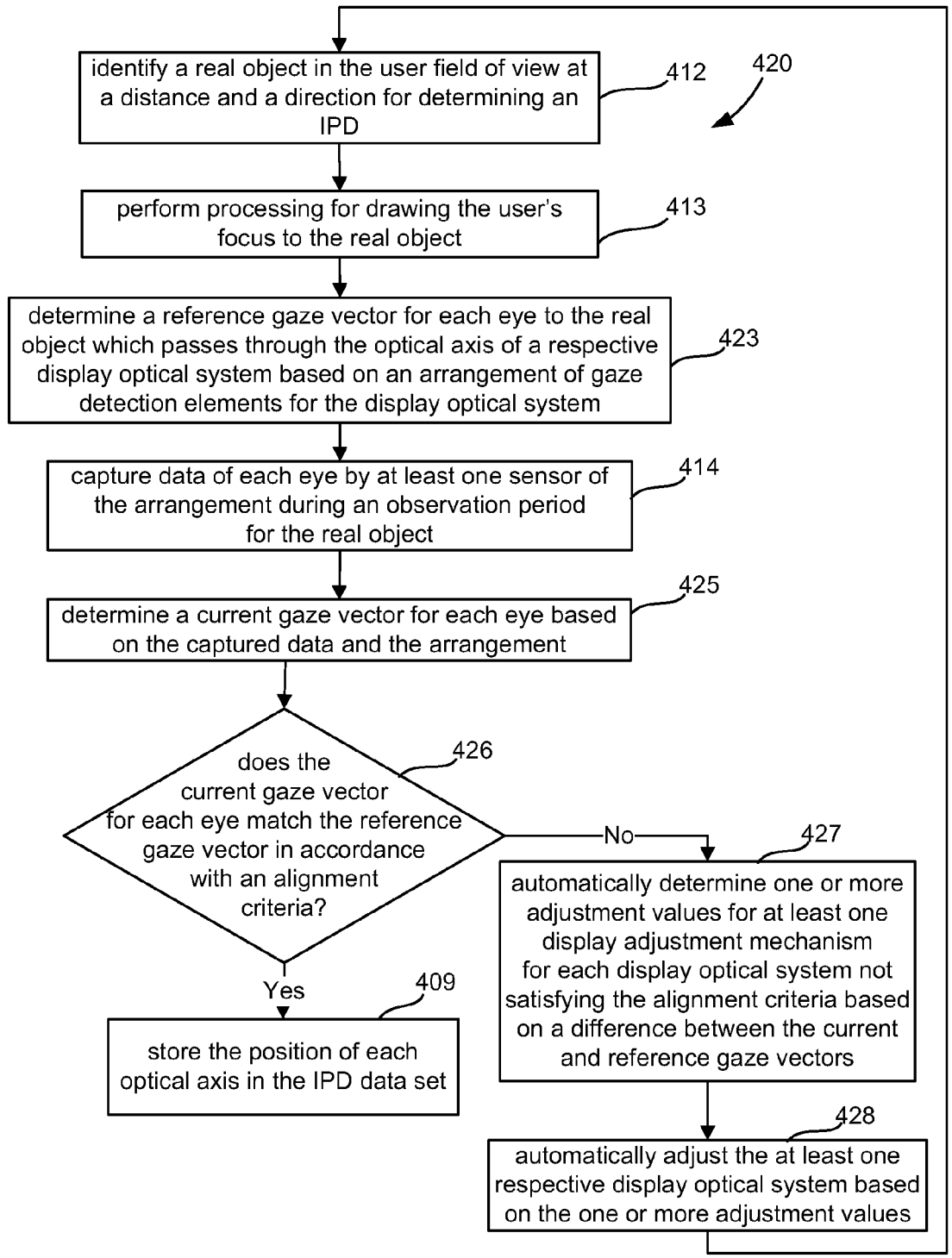
FIG. 9D is a flowchart of a method embodiment for automatically aligning a see-through, near-eye, mixed reality display with an IPD based on gaze data.

FIG. 9D is a flowchart of a method embodiment 420 for an implementation example for automatically aligning a see-through, near-eye, mixed reality display with an IPD based on gaze data. Steps 412 and 413 are performed as discussed above in FIG. 9B. In step 423, the one or more processors determine a reference gaze vector for each eye to the real object which passes through the optical axis of a respective display optical system based on an arrangement of gaze detection elements for the display optical system. Embodiments for gaze determination methods are discussed in FIGS. 12 through 19. Embodiments of arrangements or systems of gaze detection elements in which those methods may operate are illustrated in FIGS. 4A-4C and 6A-6D. As discussed with respect to the embodiments of FIGS. 8A and 8B, the position of the real object is tracked in the user field of view. In the case of a far IPD, a pupil position based on the user looking straight ahead is estimated, and a reference gaze vector is estimated by modeling a ray from the estimated pupil position through the optical axis to the real object.

In step 414, at least one sensor of the arrangement captures data of each eye during an observation period for the real object, and in step 425, the one or more processors determine a current gaze vector for each eye based on the captured data and the arrangement. In step 426, the one or more processors determine whether the current gaze vector matches the reference gaze vector in accordance with an alignment criteria. If so, the display device 2 has been aligned with each pupil and hence the IPD, and the one or more processors in step 409 store the position of each optical axis in the IPD data set.

If at least one of the current gaze vectors does not satisfy the alignment criteria, in step 427, the one or more processors automatically determine one or more adjustment values for at least one display adjustment mechanism for each display optical system not satisfying the alignment criteria based on a difference between the current and reference gaze vectors. The difference in the current and reference gaze vectors may be represented as a three-dimensional position difference vector, and at least one of a horizontal, a vertical and a depth adjustment value may be determined for bringing the three-dimensional position difference vector within the alignment criteria, e.g. a position difference tolerance in one or more directions.

In step 428, the one or more processors cause the at least one display adjustment mechanism to automatically adjust the at least one respective display optical system based on the one or more adjustment values.

The method embodiment of FIG. 9D may be performed with various methods for determining gaze vectors. For example, the gaze determination method embodiment of FIG. 19 may be used. Additionally, the gaze determination method of FIGS. 12 to 18 which determines a gaze vector based on image data and glint data from an inner eye part to an object may be used. In this method, the initial vector determined models an optical axis of the eye. However, as noted previously, a gaze vector in a human is the visual axis or line of sight from the fovea through the pupil center. Photoreceptors in the fovea region of the human retina are more densely packed than in the rest of the retina. This area provides the highest visual acuity or clearness of vision, and also provides stereoscopic vision of nearby objects. After determining the optical axis, a default gaze offset angle may be applied so that the optical axis approximates the visual axis and is selected as the gaze vector. In some instances, one may determine pupil alignment with the optical axis of a display optical system based on the optical axis vector determined from a center of eyeball rotation through the determined cornea and pupil centers without correcting to the visual axis. However, in other examples, the correction is applied to approximate a gaze vector from the fovea more accurately.

Figure 9E:
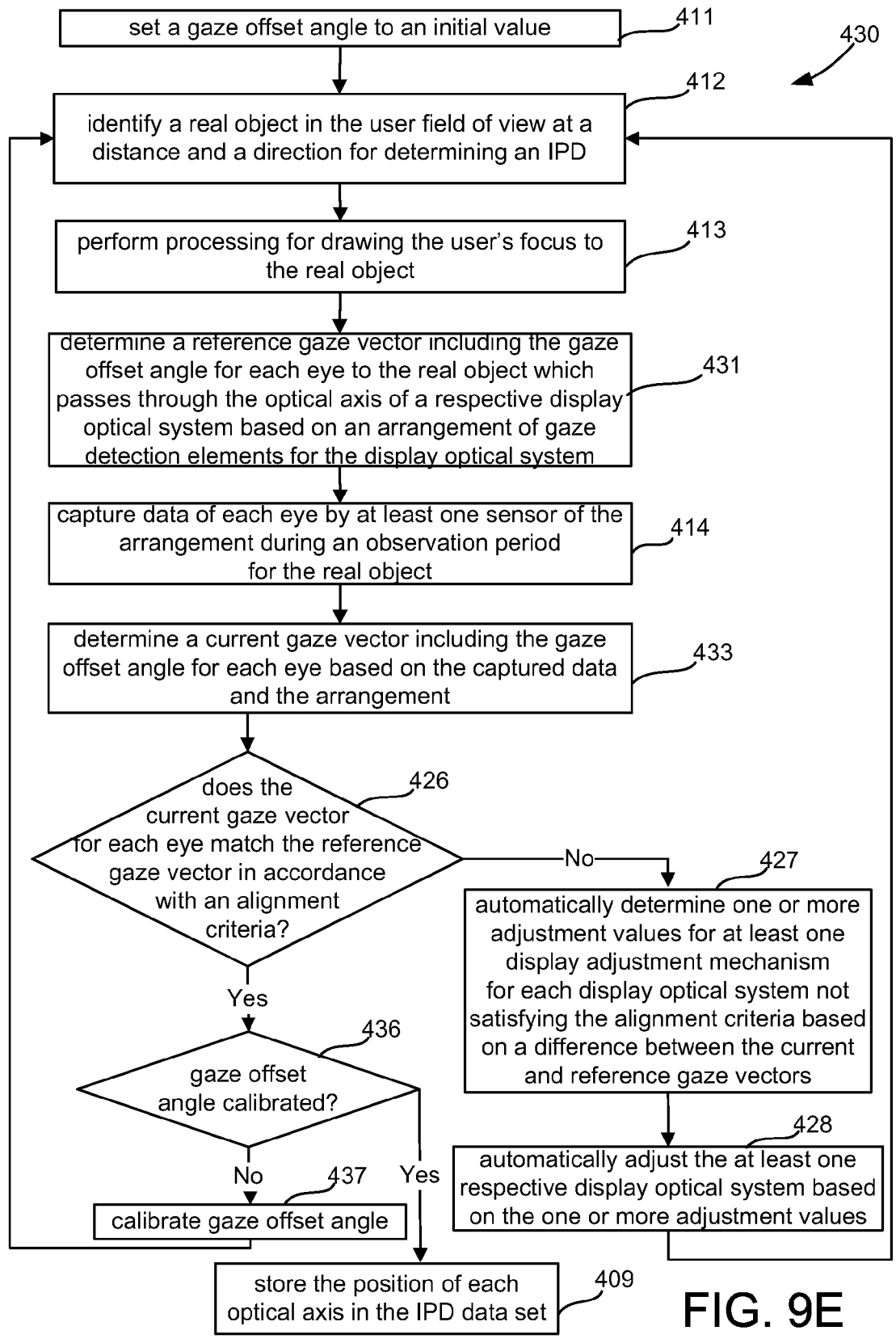
FIG. 9E is a flowchart of another version of the method embodiment of FIG. 9D.

FIG. 9E is a flowchart of a method embodiment 430 for an implementation example of the method 420 in FIG. 9D which applies the gaze offset angle. In this example, uncorrected current and reference gaze vectors are used for a coarse alignment of the pupils with their respective optical axes. Then the gaze offset angle is calibrated for the user, and the alignment check is performed again with the gaze offset angle applied to the vectors for a more fine tuned or accurate alignment with the respective optical axis. As discussed further below with respect to FIG. 18, calibration of the gaze offset angle is performed by displaying one or more images of virtual objects at different distances in the user field of view and determining the gaze offset vector based on distance vectors between the initial optical axis vectors and the positions of the one or more images in the user field of view. Virtual object images will appear clearer to a user when the IPD is properly aligned.

In step 411, a gaze offset angle is set to an initial value. Steps 412 and 413 are performed as discussed above in FIG. 9B. In step 431, the one or more processors determine a reference gaze vector to the real object which passes through the optical axis of a display optical system based on an arrangement of gaze detection elements like in step 423 except the reference gaze vector includes the gaze offset angle. Initially if the gaze offset angle is zero, the reference gaze vector is the vector extending from the optical axis of the eye. In step 414, data of each eye is captured during an observation period for the real object by at least one sensor of the arrangement. In step 433, like in step 425, a current gaze vector is determined except it includes the gaze offset angle. As in FIG. 9D, step 426 is performed. If the alignment determination fails for the optical axis of at least one display optical system, steps 427 and 428 are performed and the process beginning at step 426 is repeated.

If it is determined in step 426 that the current gaze vector matches the reference gaze vector in accordance with the alignment criteria, the one or more processors determine in step 436 whether the gaze offset angle has been calibrated. For example, the initial value may act as a flag indicating calibration has not been done or a flag otherwise stored in a memory of the display device may indicate calibration has been performed. If calibration has not been performed, the one or more processors cause the gaze offset angle to be calibrated in step 437, and the process repeats from step 412. From now on, however, the reference and gaze vectors more closely approximate the visual axis of line of sight from the user's eye. If the alignment determination in step 426 indicates satisfactory alignment, and now the gaze offset angle has been calibrated as determined in step 436, the position of each optical axis is stored in the IPD data set.

Figure 9F:
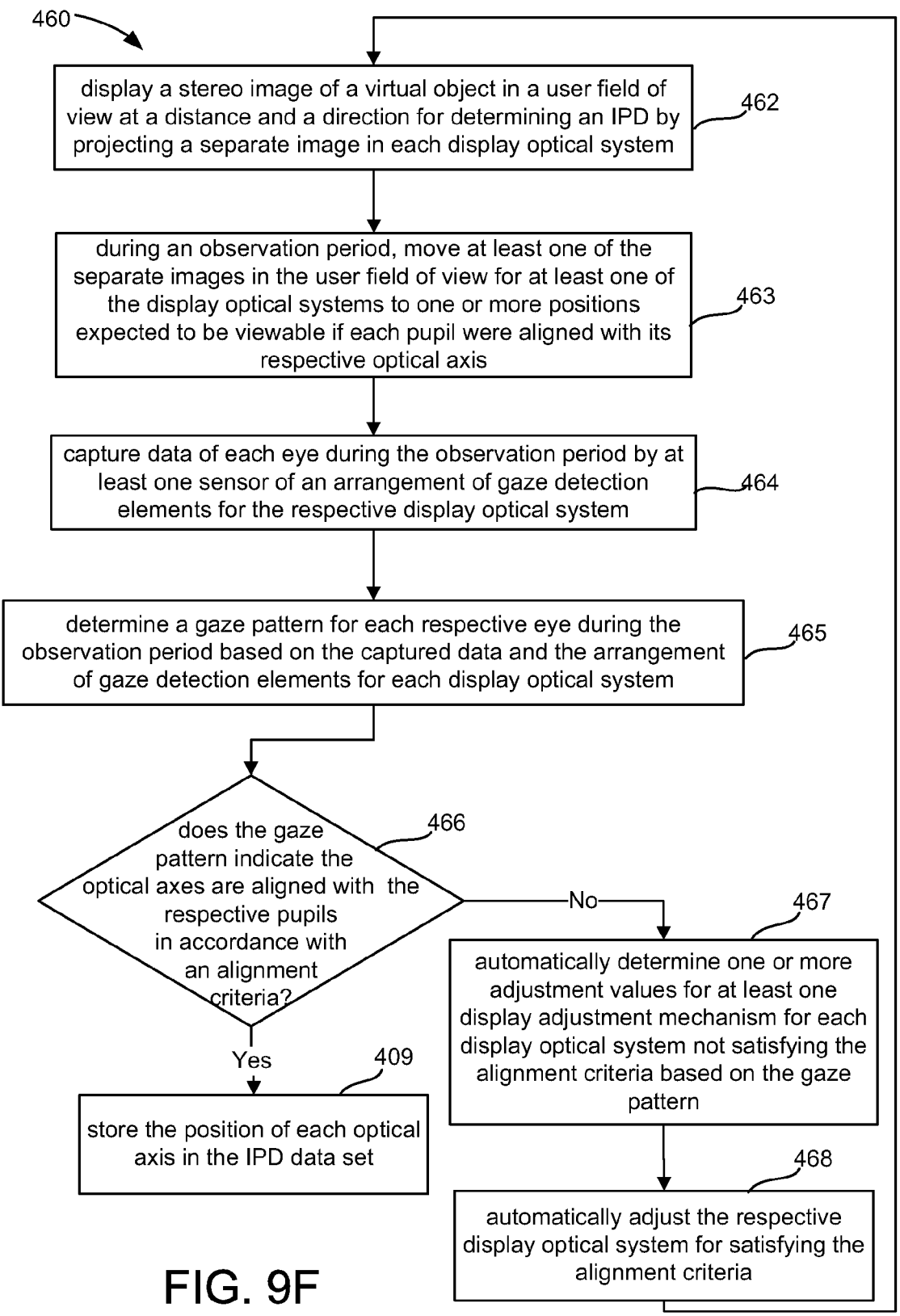
FIG. 9F is a flowchart of a method embodiment for automatically aligning a see-through, near-eye, mixed reality display with an IPD based on gaze data with respect to an image of a virtual object.

FIG. 9F is a flowchart of a method embodiment for automatically aligning a see-through, near-eye, mixed reality display with an IPD based on gaze data with respect to an image of a virtual object. In this example, the user's view of the virtual object may not be very clear to begin with as the IPD may be misaligned. However, the one or more processors have more control over virtual objects than real objects and thus more leeway in placing them in the user field of view for determining IPD. By moving the virtual stereo image in each display optical system together or separately, a gaze pattern indicates where in the field of view each user eye is not tracking the object. From where in the field of view the user is not tracking the object, the one or more processors can determine how to adjust each display optical system to better align with its respective pupil.

In step 462, the one or more processors cause the image generation unit, e.g. microdisplay 120, to display a stereo image of a virtual object in a user field of view at a distance and a direction for determining an IPD by projecting a separate image in each display optical system. The two separate images make up the stereo image. In step 463, during an observation period, the one or more processors cause the image generation unit 120 to move at least one of the separate images in the user field of view for at least one of the display optical systems to one or more positions expected to be viewable if each pupil were aligned with its respective optical axis. In step 464, the one or more processors cause the at least one sensor of an arrangement of gaze detection elements for the respective display optical system to capture data of each eye during the observation period in step 464.

The one or more processors determine a gaze pattern for each eye during the observation period based on the captured data and the arrangement of gaze detection elements for each display optical system in step 465. A gaze pattern is a collection of gaze vectors determined for each position of the virtual object image in the user field of view during the observation period. In other words, the gaze pattern reflects the gaze changes during the observation period. In step 466, the one or more processors determine whether the gaze pattern indicates the optical axes are aligned with the respective pupils in accordance with an alignment criteria.

As part of the determination of step 466, the one or more processors determine whether each gaze vector calculated during a period when the virtual object was at a position in the user field of view intersected the virtual object at the position. If the alignment criteria is satisfied, the one or more processors in step 409 store the position of each optical axis in the IPD data set. If the alignment criteria is not satisfied, the one or more processors in step 467 automatically determine one or more adjustment values for at least one display adjustment mechanism for each display optical system not satisfying the alignment criteria based on the gaze pattern, and in step 468 causes the display adjustment mechanism to automatically adjust the respective display optical system for satisfying the alignment criteria.

The one or more adjustment values may be determined based on a distance vector between each gaze vector which failed to intersect the virtual object and the position of the virtual object at the time period of expected intersection.

A method embodiment such as the described in FIGS. 9D and 9F may be used when glint data is used to determine gaze. In one embodiment, glint reflections can estimate gaze based on a few data points of the intensity values detected for the glints, rather than processing much, much larger sets of image data of eyes. The position of the illuminators 153 on the eyeglass frame 115 or other support structure of a near-eye display device may be fixed so that the position of glints detected by one or more sensors is fixed in the sensor detection area. The cornea and hence the iris and the pupil rotate with the eyeball about a fixed center. The iris, pupil and the sclera which is sometimes referred to as the white portion of the eyeball, move underneath the glint as the user's gaze changes. So a glint detected at a same sensor location may result in different intensity values due to different reflectivities associated with the different eye parts. As the pupil is a hole with tissue that absorbs most incoming light, the intensity value for it would be very low or near zero, while that for the iris would be a higher intensity value due to its higher reflectivity. An intensity value for the sclera may be highest as the sclera has the highest reflectivity.

In some examples, an illuminator may be positioned as in FIGS. 6A through 6D on either side of the display optical system 14 and hence on either side of the pupil of the user's eye. In other embodiments, additional illuminators may be positioned on the frame 115 or lens 118, for example, four illuminators may be positioned to generate a surrounding geometric shape, e.g. a box, of glints on the eyeball which would be approximately centered on the pupil when a user is looking straight ahead. The microdisplay assembly 173 can display a virtual image or send a message, e.g. a visual virtual image or an audio instruction to a user to cause the user to look straight ahead for initializing the glints on or near the pupil. In other embodiments, gaze detection based on glints is based on intensity values generated from illuminators with the glint positioning being independent of being centered on the pupil.

Figure 10A:
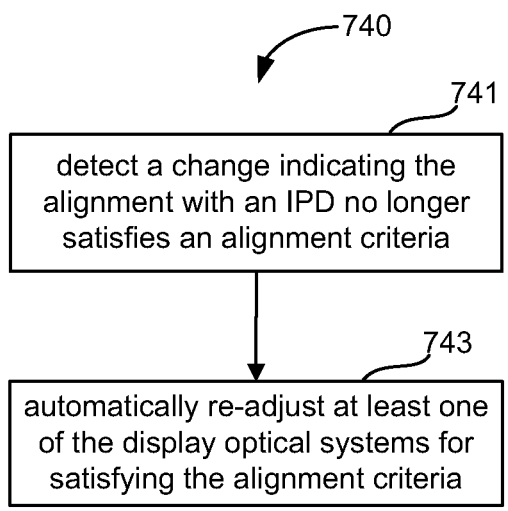
FIG. 10A is a flowchart illustrating a method embodiment for re-aligning a see-through, near-eye, mixed reality display device with an inter-pupillary distance (IPD).

FIG. 10A is a flowchart illustrating a method embodiment for re-aligning a see-through, near-eye, mixed reality display device with an inter-pupillary distance (IPD). In step 741, a change is detected by the processing unit 4, 5 indicating the alignment with the selected IPD no longer satisfies an alignment criteria which triggers one or more the processors in step 743 to automatically re-adjust at least one of the display optical systems for satisfying the alignment criteria. Again the alignment criteria may be a distance of a few millimeters, e.g. 3 mm. A gaze determination method, which is continually being done for tracking the focus of the user may detect the change.

Figure 10B:
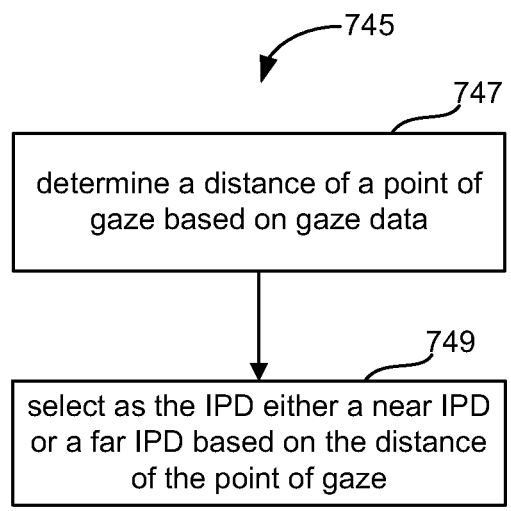
FIG. 10B is a flowchart illustrating a method embodiment for selecting an IPD from a near IPD or a far IPD.

FIG. 10B is a flowchart illustrating a method embodiment for selecting an IPD from a near IPD or a far IPD based on gaze data. The processing unit 4, 5 determines in step 752 a distance of a point of gaze based on gaze data, and in step 754 selects as the IPD either a near IPD or a far IPD based on the distance of the point of gaze. In one example, the user's point of gaze is initially determined to be seven feet or so in front of the user. The display device in this example uses two feet as the point of gaze distance for triggering changes between near and far IPD. The user's focus changes and the point of gaze determined by a gaze determination method indicates the point of gaze is within the two feet threshold for adjusting the IPD from the far or regular IPD initially selected to the near IPD. The processing unit 4, 5 monitors the point of gaze and checks the distance for detecting this change for re-adjusting between IPDs.

Other types of detected changes which may trigger re-adjustment of a display optical system is movement of the display optical system with respect to the eye. Head movement can cause the display device to shift on the user's face.

Figure 11:
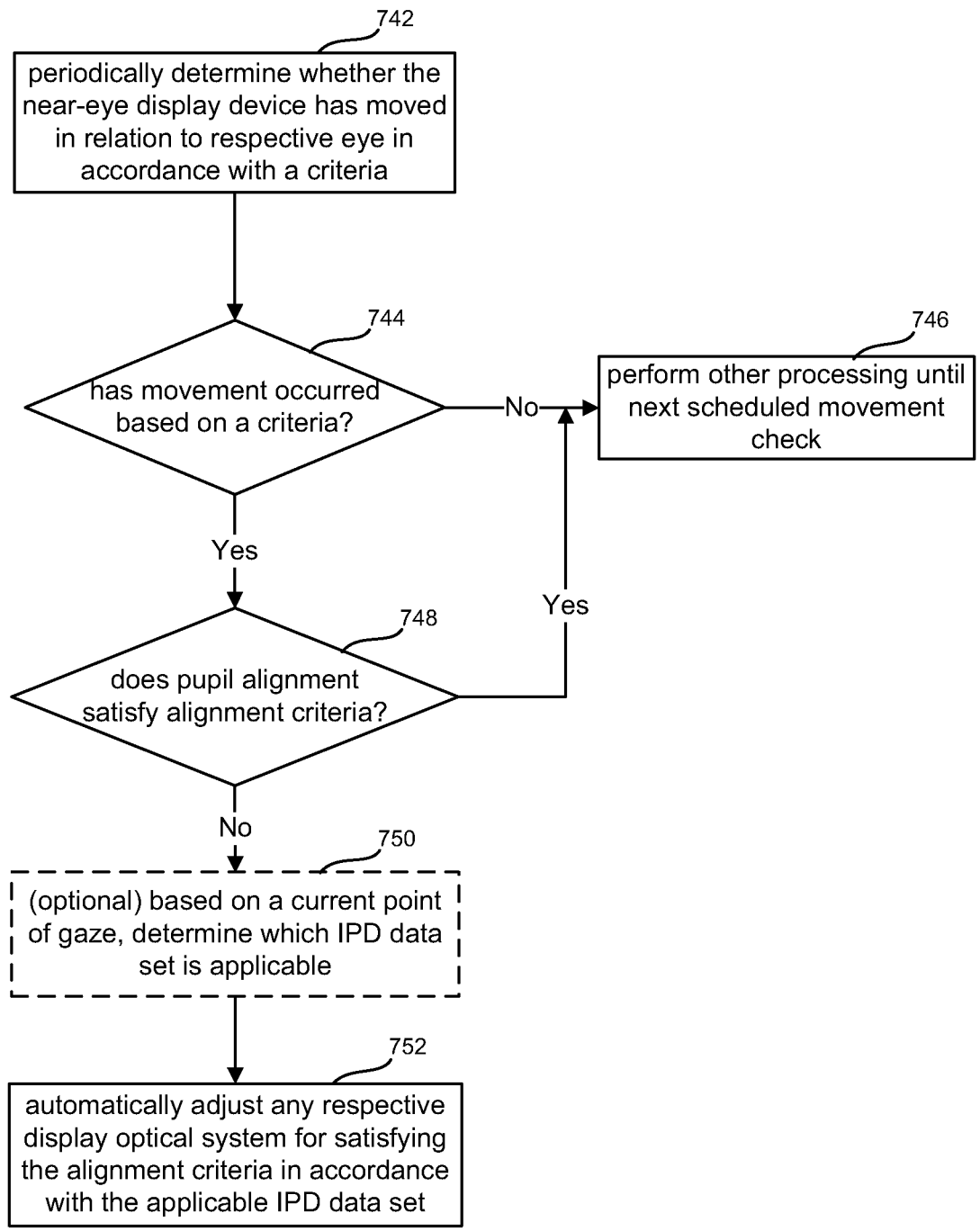
FIG. 11 is a flowchart illustrating a method embodiment for determining whether a change has been detected indicating the alignment with the selected IPD no longer satisfies an alignment criteria.

FIG. 11 is a flowchart illustrating a method embodiment for determining whether a change has been detected indicating the alignment with the selected IPD no longer satisfies an alignment criteria. In step 742, the processing unit 4, 5 periodically determines whether the near-eye display device has moved in relation to the respective eye in accordance with a criteria. In step 744, if the result indicates no movement has occurred based on the criteria, the processing unit 4,5 in step 746 performs other processing until the next scheduled movement check. If movement did occur based on the criteria, a determination is made in step 748 of whether the pupil alignment still satisfies alignment criteria. If yes, the processing unit 4,5 in step 746 performs other processing until the next scheduled movement check. If the pupil alignment no longer satisfies the alignment criteria, an optional step 750 may be performed in which the processing unit 4, 5 determines which IPD data set, near or far, is applicable based on the current point of gaze. In step 752, the processing unit 4,5 automatically adjusts any respective display optical system for satisfying the alignment criteria in accordance with the applicable IPD data set.

Based on the different geometries of gaze detection elements discussed above, movement can be detected during different gaze determination method embodiments. The processing unit 4, 5 can monitor the gaze results to determine if the re-adjustment for pupil alignment is to be done. Again, in an embodiment providing both near and far IPD alignment, the distance to the point of gaze may be monitored for triggering a switch between near and far IPD alignment.

Figure 12:
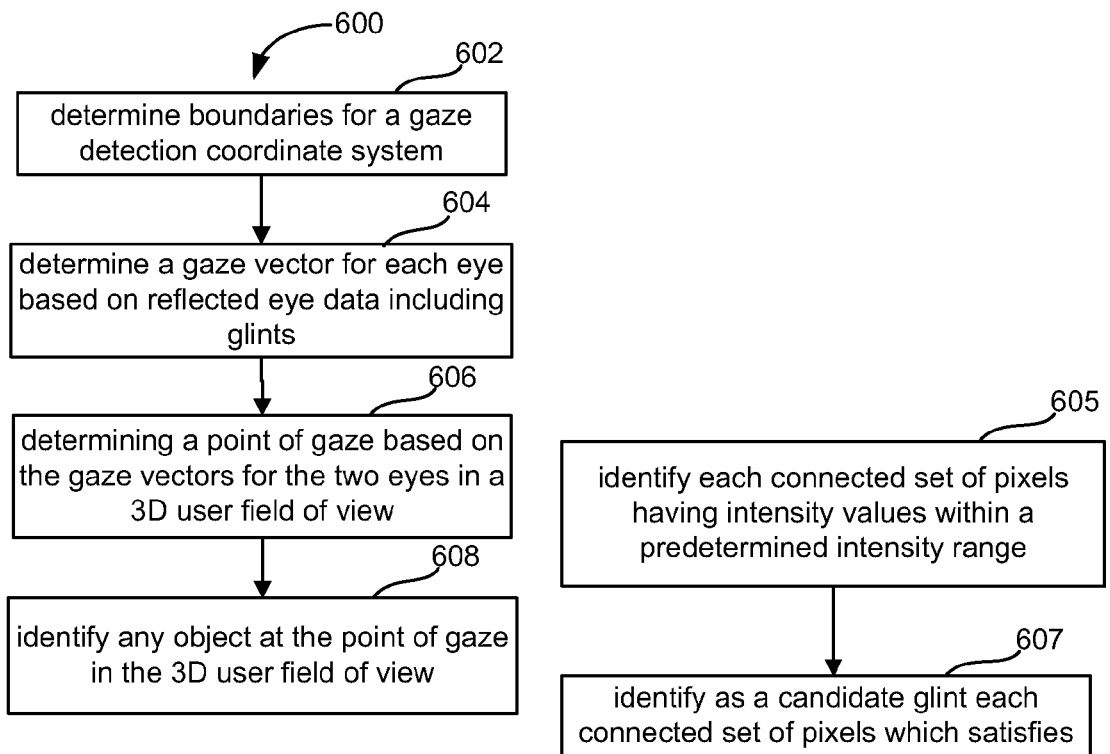
FIG. 12 is a flowchart of a method embodiment for determining gaze in a see-through, near-eye mixed reality display system.

FIG. 12 is a flowchart of a method embodiment for determining gaze in a see-through, near-eye mixed reality display system and provides an overall view of how a near-eye display device can leverage its geometry of optical components to determine gaze and a depth change between the eyeball and a display optical system. One or more processors of the mixed reality system such as processor 210 of the control circuitry, that in processing unit 4, the mobile device 5, or the hub computing system 12, alone or in combination, determine in step 602 boundaries for a gaze detection coordinate system. In step 604, a gaze vector for each eye is determined based on reflected eye data including glints, and in step 606 a point of gaze, e.g. what the user is looking at, is determined for the two eyes in a three-dimensional (3D) user field of view. As the positions and identity of objects in the user field of view are tracked, for example, by embodiments like in FIGS. 8A-8B, in step 608, any object at the point of gaze in the 3D user field of view is identified. In many embodiments, the three-dimensional user field of view includes displayed virtual objects and an actual direct view of real objects. The term object includes a person.

Figure 13:
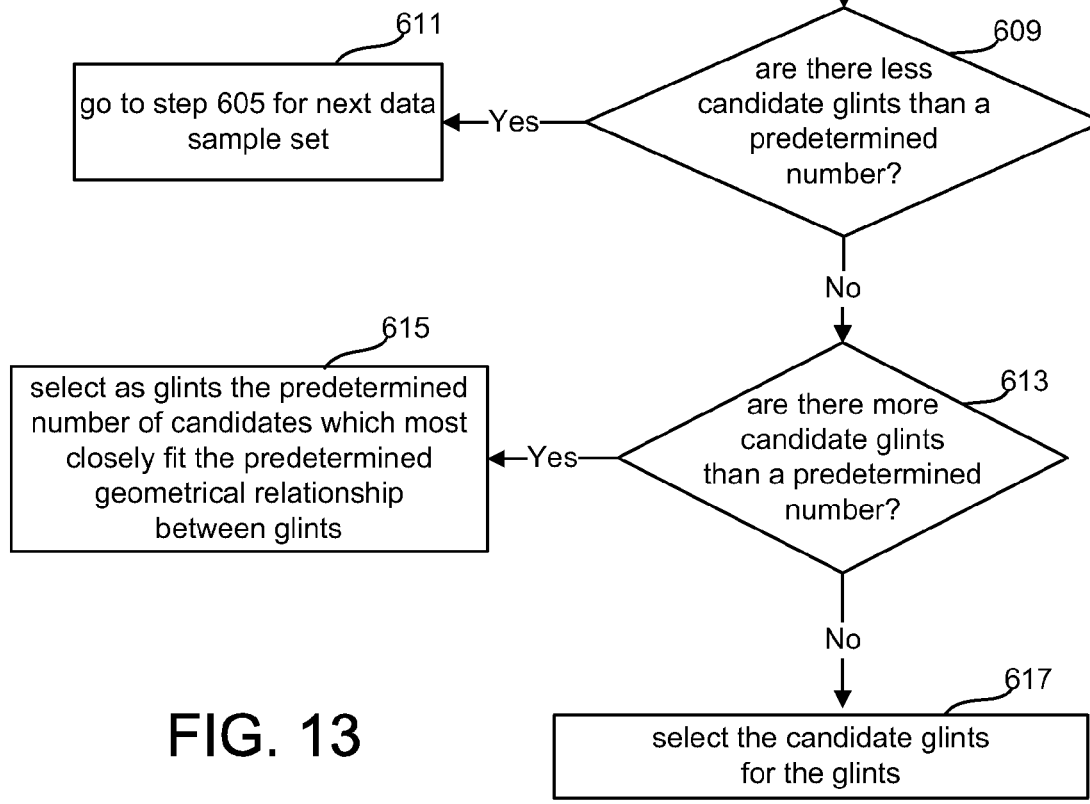
FIG. 13 is a flowchart of a method embodiment for identifying glints in image data.

The method embodiment in FIG. 12 and other method embodiments discussed below which use glint data for other ways of detecting gaze, may identify such glints from image data of the eye. When IR illuminators are used, typically an IR image sensor is used as well. The following method may also work with a discrete surface position sensitive detector (PSD), e.g. one with pixels. FIG. 13 is a flowchart of a method embodiment for identifying glints in image data. As noted above, a glint is a very small and often very bright reflection of light from a light source off of a specularly reflective surface such as the cornea of an eye. In the method embodiment below, each of the steps is performed for a data sample set. In some examples, that may include data from one image or image frame, and in others, the data sample set may be for a number of images or image frames. In step 605, the processor identifies each connected set of pixels having their intensity values within a predetermined intensity range, for example, the range of intensity values may begin at 220 and end at the brightest pixel value 255. In step 607, the candidate glints are pruned by identifying as a candidate glint each connected set of pixels which satisfies glint geometry criteria. An example of glint geometry criteria is size and shape for the glints. Some may be too large, too small, or have too irregular a shape. Furthermore, the illuminators are positioned for the resulting glints to have a spatial or geometric relationship to each other. For example, the illuminators 153 are arranged for the glints to form a rectangle. In the embodiment discussed in FIG. 14 in which a pupil center is determined from image data as well, a spatial relationship to the pupil may also be a criteria, e.g. a distance too far from the pupil may indicate a connected set is not a candidate glint.

In step 609, the one or more processors determine whether there are less candidate glints than a predetermined number. For example, for four illuminators, four glints are expected but the predetermined number may be two. In the example of the rectangle as the geometric relationship, two glints which form a horizontal line or a diagonal line of a predetermined length may have been selected as candidates. There may be an eyelid or eyelash obstruction for the other glints. If there are less than the predetermined number of glints, the data sample set is dropped for further processing, and processing returns in step 611 to step 605 of a next data sample set. If there are not less candidates than a predetermined number, then step 613 determines whether there are more candidate glints than a predetermined number. If there are more candidates, in step 615, the one or more processors select as glints the predetermined number of candidates which most closely fit the predetermined geometrical relationship between the glints. For example, for the rectangle, which candidates most closely form the rectangle of the predetermined size and shape. If there are not more candidates than the number, the number of candidates matches the predetermined number of glints, and the candidates are selected as the glints in step 617.

Due to the geometry of the placement of illuminators for generating the glints as discussed above, the glints appear in the same locations, barring movement of the frame 115 with respect to the eye. Furthermore, as the positioning of the illuminators with respect to each other on the support structure of the frame 115 or lens 118 is fixed, the spatial relationship of the glints to each other in the image is fixed as well. As for size, as the glints are very small, the number of pixels making up the glint area on the sensor and in the sensed image would be correspondingly small. For example, if the image sensor of the camera has a 1000 pixels, each glint may take up less than ten pixels. Glints may be monitored in each image frame taken for example at 30 or 60 frames a second and an area may be identified as a glint from a number of frame samples. There may not be glint data in every frame. Sampling accommodates or smoothes out obstructions of glint, and pupil data, in different image frames such as due to factors like an eyelid or eyelash covering the glint and/or pupil. An image frame is an example of an image format.

FIG. 14 is a flowchart of a method embodiment which may be used to implement step 602 of determining boundaries for a gaze detection coordinate system. One or more processors determines a position of a center 164 of a cornea of each eye with respect to the illuminators 153 and at least one light sensor, e.g. 134 or 152, based on glints in step 612. Based on image data provided by the at least one sensor, in step 614, the one or more processors determine a pupil center of each eye. In step 616, the position of the center of eyeball rotation, which may be treated as fixed, is determined relative to the cornea and pupil centers. For example, based on the pupil center, a ray can be extended back through the determined cornea center 164 to the fixed center 166 of eyeball rotation. Additionally, distance or length approximations are used for approximating the length on the optical axis between the pupil and the cornea, for example about 3 mm, and the length on the optical axis between the center of curvature of the cornea and the center of eyeball rotation, about 6 mm. These values have been determined from population studies of human eye parameters such as those compiled by Gullstrand. (See Hennessey, p. 88).

Optionally, the one or more processors in step 618 determine a position of the fixed center of eyeball rotation with respect to the illuminators and the at least one sensor for the respective eye. This position determined in step 618 provides a depth distance between a fixed point, or one that can be approximated as fixed for accuracy considerations of gaze detection, and the display optical system. In effect, a depth axis has been defined for the gaze detection coordinate system. Changes detected along the depth axis may be used to indicate that the near-eye display system has moved and trigger an alignment check of each optical axis with its respective pupil to see if the alignment criteria is still satisfied. If not, automatic readjustment is performed as per step 752. FIGS. 9A through 9D provide some examples of how the readjustment may be performed.

FIG. 15 illustrates a method embodiment for determining a position of the center of the cornea in the coordinate system with optical elements of the see-through, near-eye, mixed reality display. The one or more processors generate in step 622 a first plane including points including points including positions of a first illuminator for generating a first glint, a pupil center of the at least one image sensor, e.g. camera entrance pupil center, and the first glint. As in the embodiment of FIG. 3A, the pupil center of the camera may be positioned in relation to the detection area 139 which acts as an image plane and which directs the light it receives to an image sensor in another location. In other examples, like in FIGS. 3B and 3C, the detection area 139 may be the image sensor itself which is the image plane. This first plane will also include a position of the cornea center. Similarly, the one or more processors generate in step 624 a second plane including points including positions of a second illuminator for generating a second glint, the same pupil center of at least one sensor and the second glint. The two planes share the same camera pupil center as an origin and a distance vector to each illuminator is fixed with respect to the camera pupil center as the image sensor and illuminators are positioned on the near-eye display device at predetermined locations. These predetermined locations allow the various points in the planes to be related to each other in a third coordinate system including the two illuminators, the position of the camera pupil center, and the cornea center of curvature. The processor determines in step 626 the position of the cornea center of curvature based on the intersection of the first and second planes.

Figure 16:
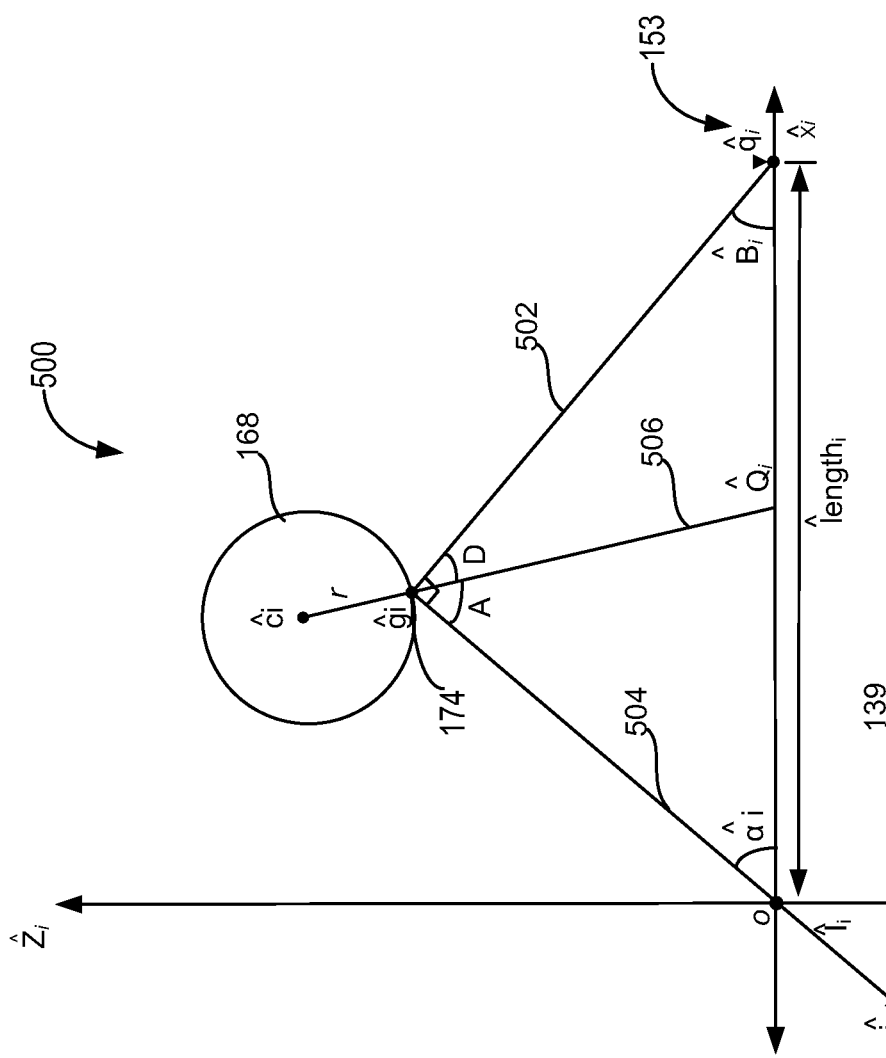
FIG. 16 provides an illustrative example of defining a plane using the geometry provided by an arrangement of optical elements to form the gaze detection coordinate system which may be used by the embodiment of FIG. 15 to find the cornea center.

FIG. 16 provides an illustrative example of the geometry of a gaze detection coordinate system 500 which may be used by the embodiment of FIG. 15 to find the cornea center. In this embodiment, the at least one sensor is a camera modeled as a pin-hole camera. The geometry depicted is a slightly modified version of FIG. 3 on page 89 of (Hennessey et al. "A Single Camera Eye-Gaze Tracking System with Free Head Motion," ETRA 2006, San Diego, Calif., ACM p. 88, pp. 87-94 (hereafter Hennessey), which is hereby incorporated by reference. A list of variables is provided as follows:

$\hat{q}_i$ is a position of an illuminator$_i$, the light of which produces glint $\hat{g}_i$, (e.g. 174)

$\hat{g}_i$ is the glint produced by illuminator$_i$ (153) on a cornea surface, $\hat{o}$ is a camera pupil center of the pin-hole camera model, $\hat{I}_i$ is the image of glint $\hat{g}_i$ on the image plane which is the detection area 139 of the camera sensor, length$_i$ is the scalar distance or length from point $\hat{o}$ to $\hat{q}_i$, $\hat{I}_i$ is the vector from the camera pupil center $\hat{o}$ to the image $\hat{I}_i$ on the image sensor of the glint $\hat{g}_i$, $\hat{Q}_i$ is the vector from the camera pupil center ô to the position $\hat{q}_i$ of illuminator$_i$, the $\hat{X}_i$ axis is defined $\hat{Q}_i$, along in this example and the $\hat{Z}_i$ axis of the coordinate system is such so that $\hat{I}_i$ which connects the image $\hat{i}_i$ of the glint $\hat{g}_i$ on image plane 139 (detection area) lies in a plane formed by the $\hat{X}_i$ and $\hat{Z}_i$ axes.

$\hat{\beta}$ is an angle formed in the $\hat{X}_i\hat{Z}_i$ plane between a line 502 representing the incident ray of light from the illuminator (153) position $\hat{q}_i$ to the glint $\hat{g}_i$ (174) on a cornea surface.

$\hat{\alpha}$ is the angle formed in the $\hat{X}_i\hat{Z}_i$ plane between a line 504 representing the reflected ray from the glint $\hat{g}_i$ to the camera pupil center of the camera, ô, which is also the origin of the coordinate system.

$\hat{c}$ is the position of the cornea center which also lies in the $\hat{X}_i\hat{Z}_i$ plane.

As the cornea is modeled as a sphere, r is the radius of the corneal sphere, and each glint $\hat{g}_i$ is a point on the first or external surface of the sphere, so each glint is separated from the cornea center by the radius r. In the above example, the glint $\hat{g}_i$ is modeled as a point on the exterior surface or first surface of the cornea. In such a model, the light of the illuminator is bouncing off the cornea in the same medium, air, so of the same index of refraction as the reflected light of glint directed back to the camera sensor.

As shown in FIG. 16, a line or ray 506 normal to the glint $\hat{g}_i$ on the surface of the cornea can be extended from the glint in the direction of the cornea and also extended to intersect with the $\hat{X}_i$ axis of the $\hat{X}_i\hat{Z}_i$ plane of the coordinate system. Also as shown in FIG. 16, the incident ray 502 and the reflected ray 504 make a right triangle with the line length$_i$ between the position of the illuminator $\hat{q}_i$ and the camera pupil center ô. Thus angle A and angle D is each represented by $$\frac{\pi - \hat{\alpha}_i - \hat{\beta}_i}{2} \text{ wherein } \hat{\alpha}_i =$$

$$\cos^{-1}\left(\frac{-\hat{I}_i \cdot \hat{Q}_i}{\|-\hat{I}_i\| \cdot \|\hat{Q}_i\|}\right) \text{ and } \hat{\beta}_i = \tan^{-1}\left(\frac{\hat{g}_{ix} \cdot \tan(\hat{\alpha}_i)}{\hat{I}_i - \hat{g}_{ix}}\right).$$

According to Hennessey, the center of the cornea $\hat{c}_i$ can be defined in the coordinate system 500 in terms of the unknown parameter $\hat{g}_{ix}$ resulting in 3 equations for 4 unknowns ($\hat{c}_{ix}$, $\hat{c}_{iy}$, $\hat{c}_{iz}$, $\hat{g}_{ix}$) as follows:

$$\begin{bmatrix} \hat{c}_{ix} \\ \hat{c}_{iy} \\ \hat{c}_{iz} \end{bmatrix} = \begin{bmatrix} \hat{g}_{ix} - r \cdot \sin\left(\frac{\hat{\alpha}_i - \hat{\beta}_i}{2}\right) \\ 0 \\ \hat{g}_{ix} \cdot \tan(\hat{\alpha}_i) + r \cdot \cos\left(\frac{\hat{\alpha}_i - \hat{\beta}_i}{2}\right) \end{bmatrix}$$

Another two-dimensional plane including the cornea center, ĉ, another glint $\hat{g}_i$, the camera pupil center ô of the camera and a position $\hat{q}_i$ of another illuminator is also formed. The camera pupil center ô of the camera and the cornea center are the same in each plane although the camera pupil center ô position is known. This will result in 6 equations with 8 unknowns. In Hennessey, the gaze detection coordinate system is treated as an auxiliary coordinate system for which a rotation matrix $\hat{R}_i$ can transform points between the auxiliary coordinate systems for each plane and a single world coordinate system such as the third coordinate system which relates the position of the detection area 139 to the illuminators 153. A constraint exists in which the cornea center defined for each glint is the same in the world coordinate system, e.g. $\hat{c}_1 = \hat{c}_2$ and 3 equations result for the different axis components, e.g., $\hat{c}_{1x} = \hat{c}_{2x}$, $\hat{c}_{1y} = \hat{c}_{2y}$, and $\hat{c}_{1z} = \hat{c}_{2z}$, thus providing 9 equations with 8 unknowns. Hennessey (p. 90) states to solve numerically for ĉ using a gradient descent algorithm. Thus, the position center 164 of the cornea 168 is defined with respect to the positions of the illuminators and the image plane or detection area 139.

FIG. 17 illustrates a method embodiment for determining a pupil center from image data generated by a sensor. In step 642, the one or more processors identify a black pupil area in a number of image data samples of the respective eye and in step 644 averages the black pupil areas in the number of image data samples to adjust for headshake. An assumption may be made that a pupil is a circle and when viewed from an angle is an ellipse. One axis of the ellipse, the major axis, remains constant as it represents the diameter of the pupil which does not change, provided the lighting does not change, as pupil size changes with lighting changes.

The pupil appears as a circle in an image format such as an image frame of a camera having its detection area centered on the optical axis of the display when the pupil is looking straight ahead through the display. As the pupil changes its gaze and moves from the center of the image frame, the pupil appears as an ellipse, as a circle viewed from an angle appears as an ellipse. The width of the minor axis of the ellipse changes with gaze changes. A narrow ellipse to the left of the center of the image frame indicates the user is looking to the far right. A wider ellipse a distance less to the right of the center of the image frame indicates the user is looking left but not far left.

The center of the pupil is the center of the ellipse. The ellipse is fitted from detected edge points in the image. Because such edge points are noisy and not all of them are on the ellipse, the ellipse fitting process is repeated many times over randomly selected subsets of all edge points. The subset that is most consistent with all the edge points is used to obtain the final ellipse. The processor in step 646 performs an ellipse fitting algorithm on the average black pupil area for determining an ellipse representing the pupil, and in step 648 determines the center of the pupil by determining the center of the ellipse representing the pupil.

With the center of rotation, the cornea center and the pupil center identified, one can extend a ray from the center of rotation through the cornea and pupil centers to obtain an optical axis for the eye. However, as noted previously, a gaze vector in a human is the visual axis or line of sight from the fovea through the pupil center. Photoreceptors in the fovea region of the human retina are more densely packed than in the rest of the retina. This area provides the highest visual acuity or clearness of vision, and also provides stereoscopic vision of nearby objects. After determining the optical axis, a default gaze offset angle may be applied so that the optical axis approximates the visual axis and is selected as the gaze vector.

FIG. 18 illustrates a method embodiment for determining a gaze vector based on the determined centers for the pupil, the cornea and the center of rotation of the eyeball and which embodiment may be used to implement step 604. In step 652, the one or more processors model an optical axis 178 for the eye as a ray extending from the fixed center of rotation of the eyeball through the determined cornea and pupil centers and in step 654 applies a correction to the modeled optical axis for estimating a visual axis. In step 656, the one or more processors extend the estimated visual axis from the pupil through the display optical system of the see-through, near-eye display into the user field of view.

In one embodiment, with the fixed positioning of the illuminators as a basis, the effect of different areas of the eye on reflectivity and hence on the amount or intensity of light reflected is used as a basis for gaze detection. Intensity data from either IR or visible light sensors may be used to determine gaze, so the reflectivity data may be based on IR based reflectivity or visible light reflectivity. For illustration, the sclera is more reflective than other areas of the eye like the pupil and the iris. If a user looks to the user's far left, an illuminator 153 located on the frame 115 at the user's far right causes a glint reflection on the right sclera of the user's right eye. PSD 134*r* or as in FIG. 6B, photodetector 152 on the inner right frame near bridge 104 receives more reflected light represented in a data reading while the light from reflection at the other photodector 152 or position on the PSD when the illuminator 153 nearest the bridge is turned on receives a lower amount of reflected light in a range associated with the black pupil. The reflectivity of the iris may also be captured by camera 134 and stored for the user by the processor 210, the processing unit 4 or a mobile device 5 embodying the processing unit 4.

The accuracy may not be as much as those based on images of the full eye, but may suffice for many applications. Additionally, such a gaze detection may be useful as an auxiliary or backup gaze detection technique. For example, during computationally intensive periods of generating complex virtual images, such a glint based technique relieves some processor overhead. Furthermore, such a glint-based technique can be executed many more times in a time period than an image based technique which processes more data or a computationally intensive but more accurate technique which may be run at a slower rate to recalibrate accuracy of gaze detection periodically. An example of a gaze detection technique which is both image based and more computationally intensive is one for determining a gaze vector with respect to inner parts of the eye based on glint data and pupil image data like the embodiments described in FIGS. 12 to 18, which may be run at a slower rate to recalibrate accuracy of gaze detection periodically. For example, an embodiment of the more computationally intensive technique based in part on image data may be run at ten (10) times a second while the glint based gaze detection technique may be run at a faster rate of one hundred (100) times per second or even five (500) hundred in some instances.

FIG. 19 is a flowchart illustrating a method embodiment for determining gaze based on glint data. In step 673, data is captured representing each glint intensity value. Based on specular reflectivities of different eye parts, and positions of illuminators, an eyeball part is identified in step 674 based on the intensity value detected for each glint position in a geometrical relationship of the glints. In step 675, a gaze angle is estimated based on the eyeball part associated with each of the glint positions. As described in previous examples, an eyeball part may be an iris, a pupil or a sclera of the eyeball. The positions of the illuminators form a geometry for the glints, e.g. a box, a circle, a rectangle, etc. which frame or surround the pupil, at least on two sides. A gaze vector is determined in step 676 based on the gaze angle, and a point of gaze in the 3D user field of view is determined in step 677 based on the intersection of the gaze vectors determined for both eyes.

As noted above, different methods with different accuracies may be employed at different periodic rates to trade accuracy for speed. A method embodiment based on glint intensity values such as that described in FIG. 19 is an example of a technique with a low computational intensity which may be employed.

Other tests for movement may be performed based on a facial feature with a fixed characteristic in image data. In one embodiment, an eye camera may capture about 5 to 10 mm of area around the visible eyeball portion of the cornea bulge, eye white, iris and pupil so as to capture part of an eyelid and eyelashes. A positionally fixed facial feature like a mole or freckle on skin such as an eyelid or on the bottom rim of the skin encasing the lower eyeball may also be present in the image data of the eye. In image samples, the position of the mole or freckle may be monitored for a change in position. If the facial feature has moved up, down, right or left, a vertical or horizontal shift can be detected. If the facial feature appears larger or smaller, a depth change in the spatial relationship between eye and display device 2 can be determined. There may be a criteria range in the change of position to trigger recalibration of the training images due to things like camera resolution, etc.

In another example, although lighting is a factor which changes the size of the pupil and the ratio of pupil area to visible iris area within the circumference or perimeter of the iris, the size of the perimeter or circumference of the iris does not change with gaze change or lighting change; hence, the perimeter or circumference is a fixed characteristic of the iris as a facial feature. Through ellipse fitting of the iris, processor 210 or a processor of the processing unit 4,5 of the display device 2 can determine whether the iris has become larger or smaller in image data in accordance with criteria. If larger, the display device 2 with its illuminators 153 and at least one sensor 134 has moved closer in depth to the user's eye; if smaller, the display device 2 has moved farther away. A change in a fixed characteristic can trigger an IPD alignment check.

Besides depth changes, vertical and horizontal changes in pupil alignment can also be determined by a periodic check displaying a virtual object at a predetermined distance for the user to see when looking straight ahead, and seeing if the pupil is centered on the optical axis as per being centered in image data or in a predetermined glint position. Vertical and horizontal changes can also trigger readjustment. As shown in the examples above, the display adjustment mechanism in some embodiments provides for movement in any of three dimensions.

FIG. 20 is a block diagram of an exemplary mobile device which may operate in embodiments of the technology. Exemplary electronic circuitry of a typical mobile phone is depicted. The phone 900 includes one or more microprocessors 912, and memory 1010 (e.g., non-volatile memory such as ROM and volatile memory such as RAM) which stores processor-readable code which is executed by one or more processors of the control processor 912 to implement the functionality described herein.

Mobile device 900 may include, for example, processors 912, memory 1010 including applications and non-volatile storage. The processor 912 can implement communications, as well as any number of applications, including the interaction applications discussed herein. Memory 1010 can be any variety of memory storage media types, including non-volatile and volatile memory. A device operating system handles the different operations of the mobile device 900 and may contain user interfaces for operations, such as placing and receiving phone calls, text messaging, checking voicemail, and the like. The applications 1030 can be any assortment of programs, such as a camera application for photos and/or videos, an address book, a calendar application, a media player, an internet browser, games, other multimedia applications, an alarm application, other third party applications, the interaction application discussed herein, and the like. The non-volatile storage component 1040 in memory 1010 contains data such as web caches, music, photos, contact data, scheduling data, and other files.

The processor 912 also communicates with RF transmit/receive circuitry 906 which in turn is coupled to an antenna 902, with an infrared transmitted/receiver 908, with any additional communication channels 1060 like Wi-Fi or Bluetooth, and with a movement/orientation sensor 914 such as an accelerometer. Accelerometers have been incorporated into mobile devices to enable such applications as intelligent user interfaces that let users input commands through gestures, indoor GPS functionality which calculates the movement and direction of the device after contact is broken with a GPS satellite, and to detect the orientation of the device and automatically change the display from portrait to landscape when the phone is rotated. An accelerometer can be provided, e.g., by a microelectromechanical system (MEMS) which is a tiny mechanical device (of micrometer dimensions) built onto a semiconductor chip. Acceleration direction, as well as orientation, vibration and shock can be sensed. The processor 912 further communicates with a ringer/vibrator 916, a user interface keypad/screen, biometric sensor system 918, a speaker 1020, a microphone 922, a camera 924, a light sensor 926 and a temperature sensor 928.

The processor 912 controls transmission and reception of wireless signals. During a transmission mode, the processor 912 provides a voice signal from microphone 922, or other data signal, to the RF transmit/receive circuitry 906. The transmit/receive circuitry 906 transmits the signal to a remote station (e.g., a fixed station, operator, other cellular phones, etc.) for communication through the antenna 902. The ringer/vibrator 916 is used to signal an incoming call, text message, calendar reminder, alarm clock reminder, or other notification to the user. During a receiving mode, the transmit/receive circuitry 906 receives a voice or other data signal from a remote station through the antenna 902. A received voice signal is provided to the speaker 1020 while other received data signals are also processed appropriately.

Additionally, a physical connector 988 can be used to connect the mobile device 900 to an external power source, such as an AC adapter or powered docking station. The physical connector 988 can also be used as a data connection to a computing device. The data connection allows for operations such as synchronizing mobile device data with the computing data on another device.

A GPS transceiver 965 utilizing satellite-based radio navigation to relay the position of the user applications is enabled for such service.

The example computer systems illustrated in the figures include examples of computer readable storage media. Computer readable storage media are also processor readable storage media. Such media may include volatile and nonvolatile, removable and non-removable media implemented in any method or technology for storage of information such as computer readable instructions, data structures, program modules or other data. Computer storage media includes, but is not limited to, RAM, ROM, EEPROM, cache, flash memory or other memory technology, CD-ROM, digital versatile disks (DVD) or other optical disk storage, memory sticks or cards, magnetic cassettes, magnetic tape, a media drive, a hard disk, magnetic disk storage or other magnetic storage devices, or any other medium which can be used to store the desired information and which can accessed by a computer.

Figure 21:
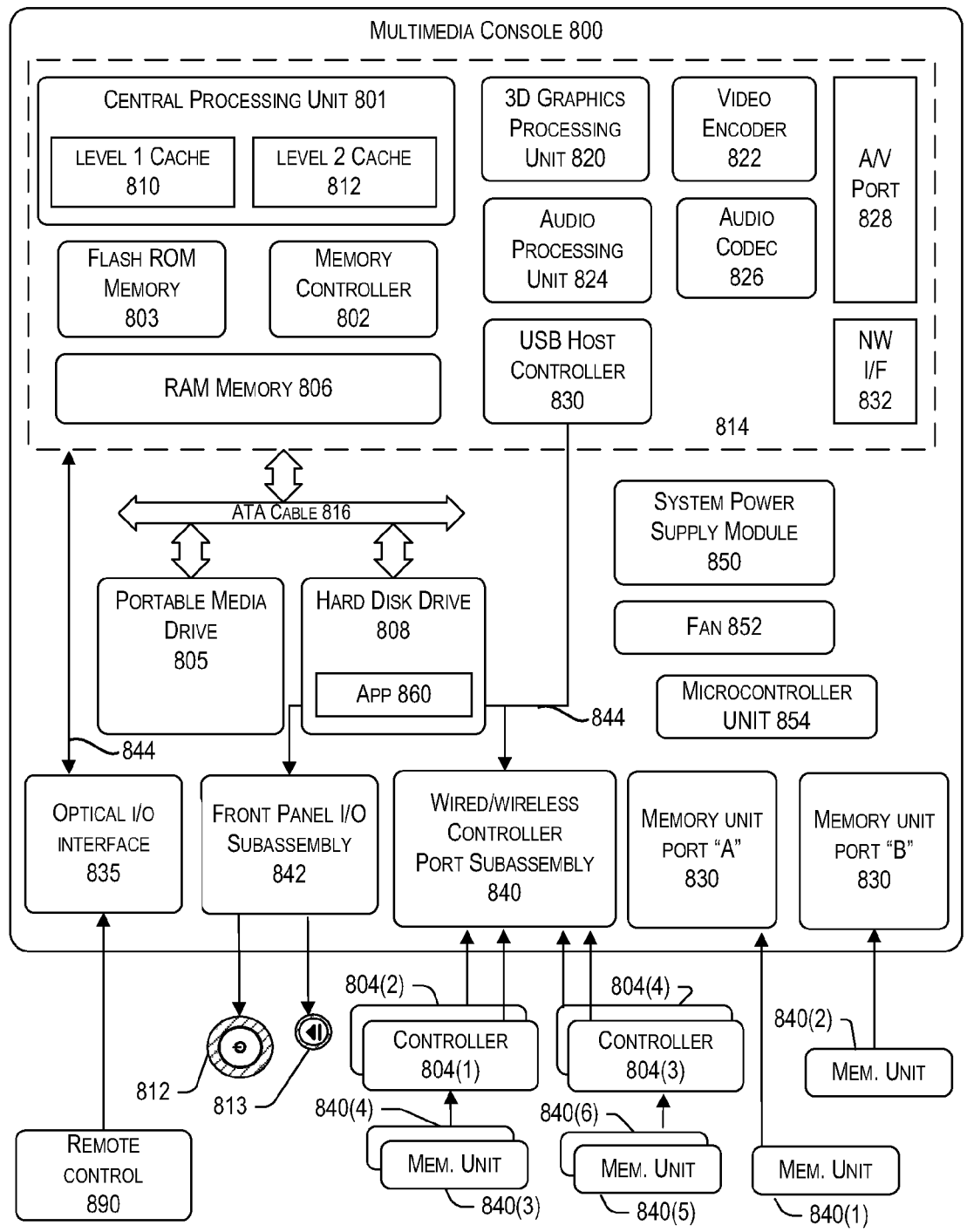
FIG. 21 is a block diagram of one embodiment of a computing system that can be used to implement a hub computing system.

FIG. 21 is a block diagram of one embodiment of a computing system that can be used to implement a hub computing system like that of FIGS. 1A and 1B. In this embodiment, the computing system is a multimedia console 800, such as a gaming console. As shown in FIG. 18, the multimedia console 800 has a central processing unit (CPU) 801, and a memory controller 802 that facilitates processor access to various types of memory, including a flash Read Only Memory (ROM) 803, a Random Access Memory (RAM) 806, a hard disk drive 808, and portable media drive 806. In one implementation, CPU 801 includes a level 1 cache 810 and a level 2 cache 812, to temporarily store data and hence reduce the number of memory access cycles made to the hard drive 808, thereby improving processing speed and throughput.

CPU 801, memory controller 802, and various memory devices are interconnected via one or more buses (not shown). The details of the bus that is used in this implementation are not particularly relevant to understanding the subject matter of interest being discussed herein. However, it will be understood that such a bus might include one or more of serial and parallel buses, a memory bus, a peripheral bus, and a processor or local bus, using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus.

In one implementation, CPU 801, memory controller 802, ROM 803, and RAM 806 are integrated onto a common module 814. In this implementation, ROM 803 is configured as a flash ROM that is connected to memory controller 802 via a PCI bus and a ROM bus (neither of which are shown). RAM 806 is configured as multiple Double Data Rate Synchronous Dynamic RAM (DDR SDRAM) modules that are independently controlled by memory controller 802 via separate buses (not shown). Hard disk drive 808 and portable media drive 805 are shown connected to the memory controller 802 via the PCI bus and an AT Attachment (ATA) bus 816. However, in other implementations, dedicated data bus structures of different types can also be applied in the alternative.

A graphics processing unit 820 and a video encoder 822 form a video processing pipeline for high speed and high resolution (e.g., High Definition) graphics processing. Data are carried from graphics processing unit (GPU) 820 to video encoder 822 via a digital video bus (not shown). Lightweight messages generated by the system applications (e.g., pop ups) are displayed by using a GPU 820 interrupt to schedule code to render popup into an overlay. The amount of memory used for an overlay depends on the overlay area size and the overlay preferably scales with screen resolution. Where a full user interface is used by the concurrent system application, it is preferable to use a resolution independent of application resolution. A scaler may be used to set this resolution such that the need to change frequency and cause a TV resync is eliminated.

An audio processing unit 824 and an audio codec (coder/decoder) 826 form a corresponding audio processing pipeline for multi-channel audio processing of various digital audio formats. Audio data are carried between audio processing unit 824 and audio codec 826 via a communication link (not shown). The video and audio processing pipelines output data to an A/V (audio/video) port 828 for transmission to a television or other display. In the illustrated implementation, video and audio processing components 820-828 are mounted on module 214.

FIG. 21 shows module 814 including a USB host controller 830 and a network interface 832. USB host controller 830 is shown in communication with CPU 801 and memory controller 802 via a bus (e.g., PCI bus) and serves as host for peripheral controllers 804(1)-804(4). Network interface 832 provides access to a network (e.g., Internet, home network, etc.) and may be any of a wide variety of various wire or wireless interface components including an Ethernet card, a modem, a wireless access card, a Bluetooth module, a cable modem, and the like.

In the implementation depicted in FIG. 21 console 800 includes a controller support subassembly 840 for supporting four controllers 804(1)-804(4). The controller support subassembly 840 includes any hardware and software components needed to support wired and wireless operation with an external control device, such as for example, a media and game controller. A front panel I/O subassembly 842 supports the multiple functionalities of power button 812, the eject button 813, as well as any LEDs (light emitting diodes) or other indicators exposed on the outer surface of console 802. Subassemblies 840 and 842 are in communication with module 814 via one or more cable assemblies 844. In other implementations, console 800 can include additional controller subassemblies. The illustrated implementation also shows an optical I/O interface 835 that is configured to send and receive signals that can be communicated to module 814.

MUs 840(1) and 840(2) are illustrated as being connectable to MU ports "A" 830(1) and "B" 830(2) respectively. Additional MUs (e.g., MUs 840(3)-840(6)) are illustrated as being connectable to controllers 804(1) and 804(3), i.e., two MUs for each controller. Controllers 804(2) and 804(4) can also be configured to receive MUs (not shown). Each MU 840 offers additional storage on which games, game parameters, and other data may be stored. In some implementations, the other data can include any of a digital game component, an executable gaming application, an instruction set for expanding a gaming application, and a media file. When inserted into console 800 or a controller, MU 840 can be accessed by memory controller 802. A system power supply module 850 provides power to the components of gaming system 800. A fan 852 cools the circuitry within console 800. A microcontroller unit 854 is also provided.

An application 860 comprising machine instructions is stored on hard disk drive 808. When console 800 is powered on, various portions of application 860 are loaded into RAM 806, and/or caches 810 and 812, for execution on CPU 801, wherein application 860 is one such example. Various applications can be stored on hard disk drive 808 for execution on CPU 801.

Gaming and media system 800 may be operated as a standalone system by simply connecting the system to monitor 16 (FIG. 1A), a television, a video projector, or other display device. In this standalone mode, gaming and media system 800 enables one or more players to play games, or enjoy digital media, e.g., by watching movies, or listening to music. However, with the integration of broadband connectivity made available through network interface 832, gaming and media system 800 may further be operated as a participant in a larger network gaming community.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for automatically aligning a near-eye, mixed reality display device with an inter-pupillary distance (IPD) for a wearer, comprising:
    automatically determining whether the near-eye, mixed reality display device, including a respective display optical system for each eye of the wearer which is positioned to be seen through by the respective eye, is aligned with a wearer IPD in accordance with an alignment criteria based on determining whether each optical axis of the respective display optical system positioned in the display device satisfies the alignment criteria for alignment with a respective pupil of the wearer; and
    responsive to the display device not being aligned with the wearer IPD in accordance with the alignment criteria, automatically adjusting a position of one or both of the display optical systems within the display device for bringing the display device into alignment with the wearer IPD, wherein the automatically adjusting comprises
        determining at least one adjustment value for a respective display adjustment mechanism based on a mapping criteria of the at least one sensor for each display optical system not satisfying the alignment criteria; and
        moving the respective display optical system based on the at least one adjustment value.

2. The method of claim 1 further comprising:
    responsive to the display device being aligned with the user IPD in accordance with the alignment criteria, storing an IPD data set for the user comprising a position of each optical axis of each display optical system of the display device.

3. The method of claim 1 wherein automatically determining whether the near-eye, mixed reality display device, including a respective display optical system for each eye which is positioned to be seen through by the respective eye, is aligned with the wearer IPD in accordance with the alignment criteria based on determining whether each optical axis of a respective display optical system positioned in the display device satisfies alignment criteria for alignment with a respective pupil of the user further comprises:
    identifying an object in the user field of view at a distance and a direction for determining an IPD;
    performing processing for drawing the wearer's focus to the object;
    capturing data of each eye during an observation period for the object by at least one sensor in an arrangement of gaze detection elements for the respective display optical system; and
    determining whether each pupil is aligned with its respective optical axis in accordance with alignment criteria based on the captured data and the arrangement of gaze detection elements.

4. The method of claim 1 wherein automatically determining whether the near-eye, mixed reality display device, including a respective display optical system for each eye which is positioned to be seen through by the respective eye, is aligned with the wearer IPD in accordance with the alignment criteria based on determining whether each optical axis of a respective display optical system positioned in the display device satisfies alignment criteria for alignment with a respective pupil of the user further comprises:
    identifying an object in the wearer field of view at a distance and a direction for determining an IPD;
    performing processing for drawing the wearer's focus to the object;

determining a reference gaze vector for each eye to the real object which passes through the optical axis of the respective display optical system for each eye based on an arrangement of gaze detection elements for the display optical system;

capturing data of each eye by at least one sensor of the arrangement during an observation period for the real object;

determining a current gaze vector for each eye based on the captured data and the arrangement; and determining whether each pupil is aligned with its respective optical axis in accordance with an alignment criteria be determining whether the current gaze vector for each eye matches the reference gaze vector for each eye.

5. The method of claim 1 wherein automatically determining whether the near-eye, mixed reality display device, including a respective display optical system for each eye which is positioned to be seen through by the respective eye, is aligned with the wearer IPD in accordance with the alignment criteria based on determining whether each optical axis of a respective display optical system positioned in the display device satisfies alignment criteria for alignment with a respective pupil of the wearer further comprises:

identifying a real object in the wearer field of view at a distance and a direction for determining an IPD;

performing processing for drawing the wearer focus to the real object;

capturing image data of each eye in an image format during an observation period for the real object by at least one sensor aligned with the optical axis of the respective display optical system of the display device, each display optical system being positioned to be seen through by a respective eye;

determining a respective pupil position from the optical axis from the image data; and determining whether each pupil aligned is aligned with its respective optical axis based on the pupil position in the image format in accordance with alignment criteria.

6. The method of claim 1 wherein determining at least one adjustment value for a respective display adjustment mechanism based on a mapping criteria of the at least one sensor for each display optical system not satisfying the alignment criteria further comprises:

based on the mapping criteria for the at least one sensor, determining a horizontal pupil position difference vector;

based on the mapping criteria for the at least one sensor, determining a vertical pupil position difference vector;

correlating the horizontal pupil position difference vector to a horizontal adjustment value; and correlating the vertical pupil position difference vector to a vertical adjustment value.

7. The method of claim 6 further comprising:

determining whether any of the horizontal or vertical adjustment values are out of range; and responsive to any horizontal or vertical adjustment value being out of range, determining a depth adjustment value for bringing any out of range adjustment value closer to being within range.

8. A system for automatically aligning a near-eye, mixed reality display with an inter-pupillary distance (IPD) of a user comprising:

a near-eye, mixed reality display device having a support structure including independently movable support structures, and having attached to a respective independently movable support structure a respective display optical system for each eye positioned to be seen through by the respective eye, each display optical system having an optical axis;

a display adjustment mechanism attached to at least one independently movable support structure for automatically adjusting a position of the respective display optical system;

a respective arrangement of gaze detection elements positioned with respect to each display optical system on the respective independently movable support structure for forming a spatial relationship between the gaze detection elements and the respective eye;

each respective arrangement including at least one respective sensor having a detection area for capturing data of the respective eye of the respective display optical system;

a memory for storing software and data including the captured data of each eye; and one or more processors having access to the memory and being communicatively coupled to the display adjustment mechanism for automatically re-positioning at least one display optical system within the display device for alignment of the optical axes of the display optical systems with the inter-pupillary distance based on the captured data and the arrangement of gaze detection elements.

9. The system of claim 8 further comprising an environment facing camera positioned on the display device to have a front facing field of view and being communicatively coupled to the one or more processors for providing image data from which the one or more processors determine a user field of view including at least a real object.

10. The system of claim 8 wherein the at least one respective sensor is an infra-red (IR) sensor; and the arrangement of gaze detection elements includes IR illuminators for generating glints, the IR illuminators being at fixed positions on the respective independently movable support structure with respect to a detection area of the IR sensor;

the IR sensor capturing data of glints on the eye associated with the respective display optical system; and the processor determining a gaze vector for the eye based on the data of glints and determining whether a pupil is aligned with the optical axis of the respective display optical system based on the gaze vector.

11. The system of claim 8 wherein the at least one respective sensor is an infra-red (IR) camera; and the arrangement of gaze detection elements includes IR illuminators for generating glints, the IR illuminators being at fixed positions on the respective independently movable support structure with respect to a detection area of the IR camera;

the IR camera capturing image data of the respective eye of the respective display optical system including any glints reflecting off the eye;

the processor determining a gaze vector from an inner part of the eye to an object in a user field of view based on determining a center of a cornea based on the image data of the glints and on determining a center of a pupil based on the image data of the eye; and the processor determining whether a pupil is aligned with the optical axis of the respective display optical system based on the gaze vector.

12. The system of claim 8 wherein the at least one respective sensor is an infra-red (IR) camera having a detection area aligned with an optical axis of the respective display optical system and capturing image data of the respective eye of the respective display optical system; and the processor determines whether a pupil of the respective eye is aligned with the optical axis of the respective display optical system based on a pupil position in the image data.

13. The system of claim 10 wherein the detection area of the IR camera is centered on the optical axis of the respective display optical system.

14. A method for automatically aligning a near-eye, mixed reality display device with an inter-pupillary distance (IPD) of a wearer, comprising:
automatically determining whether the near-eye, mixed reality display device, including a respective display optical system for each eye of the wearer which is positioned to be seen through by the respective eye, is aligned with a wearer IPD in accordance with an alignment criteria based on determining whether each optical axis of the respective display optical system positioned in the display device satisfies the alignment criteria for alignment with a respective pupil of the wearer; and
responsive to the display device not being aligned with the wearer IPD in accordance with the alignment criteria, automatically adjusting a position of one or both of the display optical systems, each display optical system supported by an independently movable support structure, within the display device for bringing the display device into alignment with the wearer IPD;
detecting a change indicating an alignment with the wearer IPD no longer satisfies the alignment criteria; and
automatically re-adjusting the one or both of the display optical systems positioned to be seen through by a respective eye for satisfying the alignment criteria.

15. The method of claim 14 wherein automatically determining whether the near-eye, mixed reality display device, including a respective display optical system for each eye which is positioned to be seen through by the respective eye, is aligned with the wearer IPD in accordance with an alignment criteria based on determining whether each optical axis of a respective display optical system positioned in the display device satisfies alignment criteria for alignment with a respective pupil of the wearer further comprises:
displaying a stereo image of a virtual object in the wearer field of view at a distance and a direction for determining an IPD by projecting a separate image in each display optical system of the display positioned to be seen through by a respective eye;
during an observation period, moving at least one of the separate images in the wearer field of view for at least one of the display optical systems to one or more positions expected to be viewable if each pupil were aligned with its respective optical axis;
capturing data of each eye during the observation period by at least one sensor of an arrangement of gaze detection elements for the respective display optical system;
determining a gaze pattern for each respective eye during the observation period based on the captured data and the arrangement of gaze detection elements for each display optical system; and
determining whether the gaze pattern indicates each optical axis is aligned with its respective pupil in accordance with an alignment criteria.

16. The method of claim 15 wherein responsive to the display device not being aligned with the wearer IPD in accordance with the alignment criteria, automatically adjusting a position of the one or both of the display optical systems within the display device for bringing the display device into alignment with the wearer IPD further comprises:
automatically determine one or more adjustment values for at least one display adjustment mechanism for each display optical system not satisfying the alignment criteria based on the gaze pattern based on a distance vector between each gaze vector of the gaze pattern which failed to intersect the virtual object of the stereo image and the position of the virtual object at the time period of expected intersection.

17. The method of claim 14 wherein detecting a change indicating an alignment with the wearer IPD no longer satisfies the alignment criteria further comprises:
determining a distance of a point of gaze based on gaze data; and
selecting as the current IPD a near IPD value or a far IPD value based on the distance of the point of gaze.

18. The method of claim 14 wherein detecting a change indicating the alignment with the wearer IPD no longer satisfies the alignment criteria further comprises determining whether the distance of the point of gaze has fallen within a distance boundary for the near IPD; and
automatically re-adjusting the one or both of the display optical systems for satisfying the alignment criteria further comprises re-adjusting the the one or both display optical systems for satisfying the alignment criteria for the near IPD.

19. The method of claim 14 wherein detecting a change indicating the alignment with the wearer IPD no longer satisfies the alignment criteria further comprises:
determining a change in a depth dimension between the the one or both display optical systems and the respective eye based on a vector from a fixed center of eyeball rotation of each eye to the position of at least one gaze detection element of the the one or both display optical systems.

* * * * *